(12) United States Patent
Schultz

(10) Patent No.: US 11,129,857 B2
(45) Date of Patent: Sep. 28, 2021

(54) ANTIVENOM COMPOSITIONS AND USES THEREOF

(71) Applicant: SnakePharm Enterprises, LLC, Playa Vista, CA (US)

(72) Inventor: Donald Schultz, Playa Vista, CA (US)

(73) Assignee: SNAKEPHARM ENTERPRISES, LLC, Playa Vista, CA (US)

( * ) Notice: Subject to any disclaimer, the term of this patent is extended or adjusted under 35 U.S.C. 154(b) by 147 days.

(21) Appl. No.: 15/604,524

(22) Filed: May 24, 2017

(65) Prior Publication Data

US 2017/0340679 A1 Nov. 30, 2017

Related U.S. Application Data

(60) Provisional application No. 62/340,983, filed on May 24, 2016.

(51) Int. Cl.
*A61K 35/583* (2015.01)

(52) U.S. Cl.
CPC .................. *A61K 35/583* (2013.01)

(58) Field of Classification Search
None
See application file for complete search history.

(56) References Cited

U.S. PATENT DOCUMENTS

| | | |
|---|---|---|
| 3,336,204 A | 8/1967 | Philpot, Jr. |
| 3,504,083 A | 3/1970 | Philpot, Jr. |
| 4,012,502 A | 3/1977 | Philpot, Jr. |
| 4,150,118 A | 4/1979 | Philpot, Jr. |
| 7,422,890 B2 | 9/2008 | Gopalakrishnakone et al. |

FOREIGN PATENT DOCUMENTS

WO WO-2007/085879 A1 8/2007

OTHER PUBLICATIONS

Thwin (Toxicon (1998), vol. 36, No. 11, pp. 1471-1482).*
Dart et al., "Validation of a Severity Score for the Assessment of Crotalid Snakebite," Annals of Emergency Medicine, Mar. 1996, vol. 27, No. 3, pp. 321-326.
Holton et al., "Development of a Behaviour-Based Scale to Measure Acute Pain in Dogs," Veterinary Record, 2001, vol. 148, pp. 525-531.
Lee et al., "Antibodies against Venom of the Snake Deinagkistrodon acutus," Applied and Environmental Microbiology, Jan. 2016, vol. 82, No. 1, pp. 71-80.
Morais-Zani et al., "Isolation of Bothrops jararaca Snake Antithrombin from he Supernatant of Fibrinogen Purification," Journal of Bimolecular Techniques, 2009, vol. 20, pp. 249-252.
Reid et al., "Development of the short-form Glasgow Composite Measure Pain Scale (CMPS-SF) and derivation of an analgesic intervention score," Animal Welfare, 2007, 16(S), pp. 97-104.
Weinstein et al., "Variability of Venom-NeutralizingProperties of Serum from Snakes of the Colubrid Genus Lampropeltis," Journal of Herpetology, vol. 26, No. 4, Dec. 1992, pp. 452-461.
International Search Report and Written Opinion from PCT/US2017/034336, dated Aug. 16, 2017, 10 pages.

* cited by examiner

*Primary Examiner* — Susan Hoffman
(74) *Attorney, Agent, or Firm* — Nathan S. Smith; Richard W. Martin; Morgan, Lewis & Bockius LLP

(57) ABSTRACT

Disclosed herein are compositions and methods for treating a victim of a venomous snakebite. Antivenom compositions are prepared from snake plasma or from snake eggs. The antivenom compositions are able to neutralize a snake venom from an autologous snake. The antivenom compositions can be administered to a snakebite victim to treat or prevent the pathological effects of a venomous snakebite.

11 Claims, 62 Drawing Sheets

| First Snake Species | | Second Snake Species | |
|---|---|---|---|
| Genus | Common Name | Genus | Common Name |
| *Aspidites* | Woma | *Boa* | Sonoran Boa Constrictor |
| *Aspidites* | Woma | *Boa* | Boa Constrictor |
| *Aspidites* | Woma | *Boa* | Tarahumara Boa Constrictor |
| *Aspidites* | Woma | *Boiga* | Dog Toothed Cat Snake |
| *Aspidites* | Woma | *Boiruna* | Mussurana (Boiruna maculata) |
| *Aspidites* | Woma | *Corallus* | Amazon Tree Boa |
| *Aspidites* | Woma | *Drymarchon* | Unicolor Cribo |
| *Aspidites* | Woma | *Drymarchon* | Black Tailed Cribo |
| *Aspidites* | Woma | *Drymarchon* | Yellow Tailed Cribo |
| *Aspidites* | Woma | *Elaphe* | King Rat Snake |
| *Aspidites* | Woma | *Elaphe* | Chinese Beauty Snake |
| *Aspidites* | Woma | *Gonionotophis* | Cape File Snake |
| *Aspidites* | Woma | *Gonionotophis* | West African File Snake |
| *Aspidites* | Woma | *Heloderma* | Beaded Lizard |
| *Aspidites* | Woma | *Hydrodynastes* | False Water Cobra |
| *Aspidites* | Woma | *Lampropeltis* | Honduran Milk Snake |
| *Aspidites* | Woma | *Lampropeltis* | Speckled Kingsnake |
| *Aspidites* | Woma | *Lampropeltis* | Atlantic Milk Snake |
| *Aspidites* | Woma | *Lampropeltis* | Desert Kingsnake |
| *Aspidites* | Woma | *Lampropeltis* | Eastern Kingsnake |
| *Aspidites* | Woma | *Lampropeltis* | California Kingsnake |
| *Aspidites* | Woma | *Lampropeltis* | Andean Milk Snake |
| *Aspidites* | Woma | *Lampropeltis* | Florida Kingsnake |
| *Aspidites* | Woma | *Lampropeltis* | Sinaloan Milk Snake |
| *Aspidites* | Woma | *Lampropeltis* | Black Milk Snake |
| *Aspidites* | Woma | *Morelia* | Coastal Carpet Python |
| *Aspidites* | Woma | *Morelia* | Jaguar Carpet Python |
| *Aspidites* | Woma | *Morelia* | Darwin Carpet Python |
| *Aspidites* | Woma | *Morelia* | Irian Jaya Carpet Python |
| *Aspidites* | Woma | *Morelia* | Carpet Python |
| *Aspidites* | Woma | *Orthriophis* | Mussurana (Clelia clelia) |
| *Aspidites* | Woma | *Orthriophis* | Yunnan Beauty Snake |
| *Aspidites* | Woma | *Pantherophis* | Corn Snake |
| *Aspidites* | Woma | *Philodryas* | Baron's Racer |
| *Aspidites* | Woma | *Pituophis* | Sonoran Gopher Snake |
| *Aspidites* | Woma | *Pituophis* | Cape Gopher Snake |
| *Aspidites* | Woma | *Pituophis* | Bull Snake |
| *Aspidites* | Woma | *Python* | Angolan Python |
| *Aspidites* | Woma | *Python* | Jampea Reticulated Python |
| *Aspidites* | Woma | *Python* | Reticulated Python |

*Fig. 1*

| First Snake Species | | Second Snake Species | |
|---|---|---|---|
| Genus | Common Name | Genus | Common Name |
| *Aspidites* | Woma | *Python* | Blood Python |
| *Aspidites* | Woma | *Python* | Ball Python |
| *Aspidites* | Woma | *Rhamphiophis* | Red Beaked Snakes |
| *Aspidites* | Woma | *Spilotes* | Tiger Rat Snake |
| *Aspidites* | Woma | *Toxicodryas* | Blandings Tree Snake |
| *Aspidites* | Woma | *Lampropeltis x Elaphe* HYBRID | California Cornsnake Hybrid |
| *Aspidites* | Woma | *Aspidites x Python* HYBRID | Woma x Ball Python Hyrbid |
| *Aspidites* | Woma | *Xenopeltis* | Sunbeam |
| *Boa* | Sonoran Boa Constrictor | *Aspidites* | Woma |
| *Boa* | Sonoran Boa Constrictor | *Boa* | Boa Constrictor |
| *Boa* | Sonoran Boa Constrictor | *Boa* | Tarahumara Boa Constrictor |
| *Boa* | Sonoran Boa Constrictor | *Boiga* | Dog Toothed Cat Snake |
| *Boa* | Sonoran Boa Constrictor | *Boiruna* | Mussurana (Boiruna maculata) |
| *Boa* | Sonoran Boa Constrictor | *Corallus* | Amazon Tree Boa |
| *Boa* | Sonoran Boa Constrictor | *Drymarchon* | Unicolor Cribo |
| *Boa* | Sonoran Boa Constrictor | *Drymarchon* | Black Tailed Cribo |
| *Boa* | Sonoran Boa Constrictor | *Drymarchon* | Yellow Tailed Cribo |
| *Boa* | Sonoran Boa Constrictor | *Elaphe* | King Rat Snake |
| *Boa* | Sonoran Boa Constrictor | *Elaphe* | Chinese Beauty Snake |
| *Boa* | Sonoran Boa Constrictor | *Gonionotophis* | Cape File Snake |
| *Boa* | Sonoran Boa Constrictor | *Gonionotophis* | West African File Snake |
| *Boa* | Sonoran Boa Constrictor | *Heloderma* | Beaded Lizard |
| *Boa* | Sonoran Boa Constrictor | *Hydrodynastes* | False Water Cobra |
| *Boa* | Sonoran Boa Constrictor | *Lampropeltis* | Honduran Milk Snake |
| *Boa* | Sonoran Boa Constrictor | *Lampropeltis* | Speckled Kingsnake |
| *Boa* | Sonoran Boa Constrictor | *Lampropeltis* | Atlantic Milk Snake |
| *Boa* | Sonoran Boa Constrictor | *Lampropeltis* | Desert Kingsnake |
| *Boa* | Sonoran Boa Constrictor | *Lampropeltis* | Eastern Kingsnake |
| *Boa* | Sonoran Boa Constrictor | *Lampropeltis* | California Kingsnake |
| *Boa* | Sonoran Boa Constrictor | *Lampropeltis* | Andean Milk Snake |
| *Boa* | Sonoran Boa Constrictor | *Lampropeltis* | Florida Kingsnake |
| *Boa* | Sonoran Boa Constrictor | *Lampropeltis* | Sinaloan Milk Snake |
| *Boa* | Sonoran Boa Constrictor | *Lampropeltis* | Black Milk Snake |
| *Boa* | Sonoran Boa Constrictor | *Morelia* | Coastal Carpet Python |
| *Boa* | Sonoran Boa Constrictor | *Morelia* | Jaguar Carpet Python |
| *Boa* | Sonoran Boa Constrictor | *Morelia* | Darwin Carpet Python |
| *Boa* | Sonoran Boa Constrictor | *Morelia* | Irian Jaya Carpet Python |
| *Boa* | Sonoran Boa Constrictor | *Morelia* | Carpet Python |

*Fig. 1 (cont.)*

| First Snake Species | | Second Snake Species | |
|---|---|---|---|
| Genus | Common Name | Genus | Common Name |
| Boa | Sonoran Boa Constrictor | Orthriophis | Mussurana (Clelia clelia) |
| Boa | Sonoran Boa Constrictor | Orthriophis | Yunnan Beauty Snake |
| Boa | Sonoran Boa Constrictor | Pantherophis | Corn Snake |
| Boa | Sonoran Boa Constrictor | Philodryas | Baron's Racer |
| Boa | Sonoran Boa Constrictor | Pituophis | Sonoran Gopher Snake |
| Boa | Sonoran Boa Constrictor | Pituophis | Cape Gopher Snake |
| Boa | Sonoran Boa Constrictor | Pituophis | Bull Snake |
| Boa | Sonoran Boa Constrictor | Python | Angolan Python |
| Boa | Sonoran Boa Constrictor | Python | Jampea Reticulated Python |
| Boa | Sonoran Boa Constrictor | Python | Reticulated Python |
| Boa | Sonoran Boa Constrictor | Python | Blood Python |
| Boa | Sonoran Boa Constrictor | Python | Ball Python |
| Boa | Sonoran Boa Constrictor | Rhamphiophis | Red Beaked Snakes |
| Boa | Sonoran Boa Constrictor | Spilotes | Tiger Rat Snake |
| Boa | Sonoran Boa Constrictor | Toxicodryas | Blandings Tree Snake |
| Boa | Sonoran Boa Constrictor | Lampropeltis x Elaphe HYBRID | California Cornsnake Hybrid |
| Boa | Sonoran Boa Constrictor | Aspidites x Python HYBRID | Woma x Ball Python Hyrbid |
| Boa | Sonoran Boa Constrictor | Xenopeltis | Sunbeam |
| Boa | Tarahumara Boa Constrictor | Boa | Sonoran Boa Constrictor |
| Boa | Tarahumara Boa Constrictor | Boa | Boa Constrictor |
| Boa | Tarahumara Boa Constrictor | Boiga | Dog Toothed Cat Snake |
| Boa | Tarahumara Boa Constrictor | Boiruna | Mussurana (Boiruna maculata) |
| Boa | Tarahumara Boa Constrictor | Corallus | Amazon Tree Boa |
| Boa | Tarahumara Boa Constrictor | Drymarchon | Unicolor Cribo |
| Boa | Tarahumara Boa Constrictor | Drymarchon | Black Tailed Cribo |
| Boa | Tarahumara Boa Constrictor | Drymarchon | Yellow Tailed Cribo |
| Boa | Tarahumara Boa Constrictor | Elaphe | King Rat Snake |
| Boa | Tarahumara Boa Constrictor | Elaphe | Chinese Beauty Snake |
| Boa | Tarahumara Boa Constrictor | Gonionotophis | Cape File Snake |
| Boa | Tarahumara Boa Constrictor | Gonionotophis | West African File Snake |
| Boa | Tarahumara Boa Constrictor | Heloderma | Beaded Lizard |
| Boa | Tarahumara Boa Constrictor | Hydrodynastes | False Water Cobra |
| Boa | Tarahumara Boa Constrictor | Lampropeltis | Honduran Milk Snake |
| Boa | Tarahumara Boa Constrictor | Lampropeltis | Speckled Kingsnake |
| Boa | Tarahumara Boa Constrictor | Lampropeltis | Atlantic Milk Snake |
| Boa | Tarahumara Boa Constrictor | Lampropeltis | Desert Kingsnake |
| Boa | Tarahumara Boa Constrictor | Lampropeltis | Eastern Kingsnake |
| Boa | Tarahumara Boa Constrictor | Lampropeltis | California Kingsnake |

*Fig. 1 (cont.)*

| First Snake Species | | Second Snake Species | |
| --- | --- | --- | --- |
| Genus | Common Name | Genus | Common Name |
| Boa | Tarahumara Boa Constrictor | Lampropeltis | Andean Milk Snake |
| Boa | Tarahumara Boa Constrictor | Lampropeltis | Florida Kingsnake |
| Boa | Tarahumara Boa Constrictor | Lampropeltis | Sinaloan Milk Snake |
| Boa | Tarahumara Boa Constrictor | Lampropeltis | Black Milk Snake |
| Boa | Tarahumara Boa Constrictor | Morelia | Coastal Carpet Python |
| Boa | Tarahumara Boa Constrictor | Morelia | Jaguar Carpet Python |
| Boa | Tarahumara Boa Constrictor | Morelia | Darwin Carpet Python |
| Boa | Tarahumara Boa Constrictor | Morelia | Irian Jaya Carpet Python |
| Boa | Tarahumara Boa Constrictor | Morelia | Carpet Python |
| Boa | Tarahumara Boa Constrictor | Orthriophis | Mussurana (Clelia clelia) |
| Boa | Tarahumara Boa Constrictor | Orthriophis | Yunnan Beauty Snake |
| Boa | Tarahumara Boa Constrictor | Pantherophis | Corn Snake |
| Boa | Tarahumara Boa Constrictor | Philodryas | Baron's Racer |
| Boa | Tarahumara Boa Constrictor | Pituophis | Sonoran Gopher Snake |
| Boa | Tarahumara Boa Constrictor | Pituophis | Cape Gopher Snake |
| Boa | Tarahumara Boa Constrictor | Pituophis | Bull Snake |
| Boa | Tarahumara Boa Constrictor | Python | Angolan Python |
| Boa | Tarahumara Boa Constrictor | Python | Jampea Reticulated Python |
| Boa | Tarahumara Boa Constrictor | Python | Reticulated Python |
| Boa | Tarahumara Boa Constrictor | Python | Blood Python |
| Boa | Tarahumara Boa Constrictor | Python | Ball Python |
| Boa | Tarahumara Boa Constrictor | Rhamphiophis | Red Beaked Snakes |
| Boa | Tarahumara Boa Constrictor | Spilotes | Tiger Rat Snake |
| Boa | Tarahumara Boa Constrictor | Toxicodryas | Blandings Tree Snake |
| Boa | Tarahumara Boa Constrictor | Lampropeltis x Elaphe HYBRID | California Cornsnake Hybrid |
| Boa | Tarahumara Boa Constrictor | Aspidites x Python HYBRID | Woma x Ball Python Hyrbid |
| Boa | Tarahumara Boa Constrictor | Xenopeltis | Sunbeam |
| Boiga | Dog Toothed Cat Snake | Boa | Sonoran Boa Constrictor |
| Boiga | Dog Toothed Cat Snake | Boa | Boa Constrictor |
| Boiga | Dog Toothed Cat Snake | Boa | Tarahumara Boa Constrictor |
| Boiga | Dog Toothed Cat Snake | Boiruna | Mussurana (Boiruna maculata) |
| Boiga | Dog Toothed Cat Snake | Corallus | Amazon Tree Boa |
| Boiga | Dog Toothed Cat Snake | Drymarchon | Unicolor Cribo |
| Boiga | Dog Toothed Cat Snake | Drymarchon | Black Tailed Cribo |
| Boiga | Dog Toothed Cat Snake | Drymarchon | Yellow Tailed Cribo |
| Boiga | Dog Toothed Cat Snake | Elaphe | King Rat Snake |
| Boiga | Dog Toothed Cat Snake | Elaphe | Chinese Beauty Snake |
| Boiga | Dog Toothed Cat Snake | Gonionotophis | Cape File Snake |

*Fig. 1 (cont.)*

| First Snake Species | | Second Snake Species | |
|---|---|---|---|
| Genus | Common Name | Genus | Common Name |
| *Boiga* | Dog Toothed Cat Snake | *Gonionotophis* | West African File Snake |
| *Boiga* | Dog Toothed Cat Snake | *Heloderma* | Beaded Lizard |
| *Boiga* | Dog Toothed Cat Snake | *Hydrodynastes* | False Water Cobra |
| *Boiga* | Dog Toothed Cat Snake | *Lampropeltis* | Honduran Milk Snake |
| *Boiga* | Dog Toothed Cat Snake | *Lampropeltis* | Speckled Kingsnake |
| *Boiga* | Dog Toothed Cat Snake | *Lampropeltis* | Atlantic Milk Snake |
| *Boiga* | Dog Toothed Cat Snake | *Lampropeltis* | Desert Kingsnake |
| *Boiga* | Dog Toothed Cat Snake | *Lampropeltis* | Eastern Kingsnake |
| *Boiga* | Dog Toothed Cat Snake | *Lampropeltis* | California Kingsnake |
| *Boiga* | Dog Toothed Cat Snake | *Lampropeltis* | Andean Milk Snake |
| *Boiga* | Dog Toothed Cat Snake | *Lampropeltis* | Florida Kingsnake |
| *Boiga* | Dog Toothed Cat Snake | *Lampropeltis* | Sinaloan Milk Snake |
| *Boiga* | Dog Toothed Cat Snake | *Lampropeltis* | Black Milk Snake |
| *Boiga* | Dog Toothed Cat Snake | *Morelia* | Coastal Carpet Python |
| *Boiga* | Dog Toothed Cat Snake | *Morelia* | Jaguar Carpet Python |
| *Boiga* | Dog Toothed Cat Snake | *Morelia* | Darwin Carpet Python |
| *Boiga* | Dog Toothed Cat Snake | *Morelia* | Irian Jaya Carpet Python |
| *Boiga* | Dog Toothed Cat Snake | *Morelia* | Carpet Python |
| *Boiga* | Dog Toothed Cat Snake | *Orthriophis* | Mussurana (Clelia clelia) |
| *Boiga* | Dog Toothed Cat Snake | *Orthriophis* | Yunnan Beauty Snake |
| *Boiga* | Dog Toothed Cat Snake | *Pantherophis* | Corn Snake |
| *Boiga* | Dog Toothed Cat Snake | *Philodryas* | Baron's Racer |
| *Boiga* | Dog Toothed Cat Snake | *Pituophis* | Sonoran Gopher Snake |
| *Boiga* | Dog Toothed Cat Snake | *Pituophis* | Cape Gopher Snake |
| *Boiga* | Dog Toothed Cat Snake | *Pituophis* | Bull Snake |
| *Boiga* | Dog Toothed Cat Snake | *Python* | Angolan Python |
| *Boiga* | Dog Toothed Cat Snake | *Python* | Jampea Reticulated Python |
| *Boiga* | Dog Toothed Cat Snake | *Python* | Reticulated Python |
| *Boiga* | Dog Toothed Cat Snake | *Python* | Blood Python |
| *Boiga* | Dog Toothed Cat Snake | *Python* | Ball Python |
| *Boiga* | Dog Toothed Cat Snake | *Rhamphiophis* | Red Beaked Snakes |
| *Boiga* | Dog Toothed Cat Snake | *Spilotes* | Tiger Rat Snake |
| *Boiga* | Dog Toothed Cat Snake | *Toxicodryas* | Blandings Tree Snake |
| *Boiga* | Dog Toothed Cat Snake | *Lampropeltis* x *Elaphe* HYBRID | California Cornsnake Hybrid |
| *Boiga* | Dog Toothed Cat Snake | *Aspidites* x *Python* HYBRID | Woma x Ball Python Hyrbid |
| *Boiga* | Dog Toothed Cat Snake | *Xenopeltis* | Sunbeam |
| *Boiruna* | Mussurana (Boiruna maculata) | *Boa* | Sonoran Boa Constrictor |
| *Boiruna* | Mussurana (Boiruna maculata) | *Boa* | Boa Constrictor |

*Fig. 1 (cont.)*

| First Snake Species | | Second Snake Species | |
|---|---|---|---|
| Genus | Common Name | Genus | Common Name |
| *Boiruna* | Mussurana (Boiruna maculata) | *Boa* | Tarahumara Boa Constrictor |
| *Boiruna* | Mussurana (Boiruna maculata) | *Boiga* | Dog Toothed Cat Snake |
| *Boiruna* | Mussurana (Boiruna maculata) | *Corallus* | Amazon Tree Boa |
| *Boiruna* | Mussurana (Boiruna maculata) | *Drymarchon* | Unicolor Cribo |
| *Boiruna* | Mussurana (Boiruna maculata) | *Drymarchon* | Black Tailed Cribo |
| *Boiruna* | Mussurana (Boiruna maculata) | *Drymarchon* | Yellow Tailed Cribo |
| *Boiruna* | Mussurana (Boiruna maculata) | *Elaphe* | King Rat Snake |
| *Boiruna* | Mussurana (Boiruna maculata) | *Elaphe* | Chinese Beauty Snake |
| *Boiruna* | Mussurana (Boiruna maculata) | *Gonionotophis* | Cape File Snake |
| *Boiruna* | Mussurana (Boiruna maculata) | *Gonionotophis* | West African File Snake |
| *Boiruna* | Mussurana (Boiruna maculata) | *Heloderma* | Beaded Lizard |
| *Boiruna* | Mussurana (Boiruna maculata) | *Hydrodynastes* | False Water Cobra |
| *Boiruna* | Mussurana (Boiruna maculata) | *Lampropeltis* | Honduran Milk Snake |
| *Boiruna* | Mussurana (Boiruna maculata) | *Lampropeltis* | Speckled Kingsnake |
| *Boiruna* | Mussurana (Boiruna maculata) | *Lampropeltis* | Atlantic Milk Snake |
| *Boiruna* | Mussurana (Boiruna maculata) | *Lampropeltis* | Desert Kingsnake |
| *Boiruna* | Mussurana (Boiruna maculata) | *Lampropeltis* | Eastern Kingsnake |
| *Boiruna* | Mussurana (Boiruna maculata) | *Lampropeltis* | California Kingsnake |
| *Boiruna* | Mussurana (Boiruna maculata) | *Lampropeltis* | Andean Milk Snake |
| *Boiruna* | Mussurana (Boiruna maculata) | *Lampropeltis* | Florida Kingsnake |
| *Boiruna* | Mussurana (Boiruna maculata) | *Lampropeltis* | Sinaloan Milk Snake |
| *Boiruna* | Mussurana (Boiruna maculata) | *Lampropeltis* | Black Milk Snake |
| *Boiruna* | Mussurana (Boiruna maculata) | *Morelia* | Coastal Carpet Python |
| *Boiruna* | Mussurana (Boiruna maculata) | *Morelia* | Jaguar Carpet Python |
| *Boiruna* | Mussurana (Boiruna maculata) | *Morelia* | Darwin Carpet Python |
| *Boiruna* | Mussurana (Boiruna maculata) | *Morelia* | Irian Jaya Carpet Python |
| *Boiruna* | Mussurana (Boiruna maculata) | *Morelia* | Carpet Python |
| *Boiruna* | Mussurana (Boiruna maculata) | *Orthriophis* | Mussurana (Clelia clelia) |
| *Boiruna* | Mussurana (Boiruna maculata) | *Orthriophis* | Yunnan Beauty Snake |
| *Boiruna* | Mussurana (Boiruna maculata) | *Pantherophis* | Corn Snake |
| *Boiruna* | Mussurana (Boiruna maculata) | *Philodryas* | Baron's Racer |
| *Boiruna* | Mussurana (Boiruna maculata) | *Pituophis* | Sonoran Gopher Snake |
| *Boiruna* | Mussurana (Boiruna maculata) | *Pituophis* | Cape Gopher Snake |
| *Boiruna* | Mussurana (Boiruna maculata) | *Pituophis* | Bull Snake |
| *Boiruna* | Mussurana (Boiruna maculata) | *Python* | Angolan Python |
| *Boiruna* | Mussurana (Boiruna maculata) | *Python* | Jampea Reticulated Python |
| *Boiruna* | Mussurana (Boiruna maculata) | *Python* | Reticulated Python |
| *Boiruna* | Mussurana (Boiruna maculata) | *Python* | Blood Python |
| *Boiruna* | Mussurana (Boiruna maculata) | *Python* | Ball Python |
| *Boiruna* | Mussurana (Boiruna maculata) | *Rhamphiophis* | Red Beaked Snakes |

Fig. 1 (cont.)

| First Snake Species | | Second Snake Species | |
|---|---|---|---|
| Genus | Common Name | Genus | Common Name |
| *Boiruna* | Mussurana (Boiruna maculata) | *Spilotes* | Tiger Rat Snake |
| *Boiruna* | Mussurana (Boiruna maculata) | *Toxicodryas* | Blandings Tree Snake |
| *Boiruna* | Mussurana (Boiruna maculata) | *Lampropeltis x Elaphe* HYBRID | California Cornsnake Hybrid |
| *Boiruna* | Mussurana (Boiruna maculata) | *Aspidites x Python* HYBRID | Woma x Ball Python Hyrbid |
| *Boiruna* | Mussurana (Boiruna maculata) | *Xenopeltis* | Sunbeam |
| *Corallus* | Amazon Tree Boa | *Aspidites* | Woma |
| *Corallus* | Amazon Tree Boa | *Boa* | Sonoran Boa Constrictor |
| *Corallus* | Amazon Tree Boa | *Boa* | Boa Constrictor |
| *Corallus* | Amazon Tree Boa | *Boa* | Tarahumara Boa Constrictor |
| *Corallus* | Amazon Tree Boa | *Boiga* | Dog Toothed Cat Snake |
| *Corallus* | Amazon Tree Boa | *Boiruna* | Mussurana (Boiruna maculata) |
| *Corallus* | Amazon Tree Boa | *Drymarchon* | Unicolor Cribo |
| *Corallus* | Amazon Tree Boa | *Drymarchon* | Black Tailed Cribo |
| *Corallus* | Amazon Tree Boa | *Drymarchon* | Yellow Tailed Cribo |
| *Corallus* | Amazon Tree Boa | *Elaphe* | King Rat Snake |
| *Corallus* | Amazon Tree Boa | *Elaphe* | Chinese Beauty Snake |
| *Corallus* | Amazon Tree Boa | *Gonionotophis* | Cape File Snake |
| *Corallus* | Amazon Tree Boa | *Gonionotophis* | West African File Snake |
| *Corallus* | Amazon Tree Boa | *Heloderma* | Beaded Lizard |
| *Corallus* | Amazon Tree Boa | *Hydrodynastes* | False Water Cobra |
| *Corallus* | Amazon Tree Boa | *Lampropeltis* | Honduran Milk Snake |
| *Corallus* | Amazon Tree Boa | *Lampropeltis* | Speckled Kingsnake |
| *Corallus* | Amazon Tree Boa | *Lampropeltis* | Atlantic Milk Snake |
| *Corallus* | Amazon Tree Boa | *Lampropeltis* | Desert Kingsnake |
| *Corallus* | Amazon Tree Boa | *Lampropeltis* | Eastern Kingsnake |
| *Corallus* | Amazon Tree Boa | *Lampropeltis* | California Kingsnake |
| *Corallus* | Amazon Tree Boa | *Lampropeltis* | Andean Milk Snake |
| *Corallus* | Amazon Tree Boa | *Lampropeltis* | Florida Kingsnake |
| *Corallus* | Amazon Tree Boa | *Lampropeltis* | Sinaloan Milk Snake |
| *Corallus* | Amazon Tree Boa | *Lampropeltis* | Black Milk Snake |
| *Corallus* | Amazon Tree Boa | *Morelia* | Coastal Carpet Python |
| *Corallus* | Amazon Tree Boa | *Morelia* | Jaguar Carpet Python |
| *Corallus* | Amazon Tree Boa | *Morelia* | Darwin Carpet Python |
| *Corallus* | Amazon Tree Boa | *Morelia* | Irian Jaya Carpet Python |
| *Corallus* | Amazon Tree Boa | *Morelia* | Carpet Python |
| *Corallus* | Amazon Tree Boa | *Orthriophis* | Mussurana (Clelia clelia) |
| *Corallus* | Amazon Tree Boa | *Orthriophis* | Yunnan Beauty Snake |
| *Corallus* | Amazon Tree Boa | *Pantherophis* | Corn Snake |

*Fig. 1 (cont.)*

| First Snake Species | | Second Snake Species | |
|---|---|---|---|
| Genus | Common Name | Genus | Common Name |
| *Corallus* | Amazon Tree Boa | *Philodryas* | Baron's Racer |
| *Corallus* | Amazon Tree Boa | *Pituophis* | Sonoran Gopher Snake |
| *Corallus* | Amazon Tree Boa | *Pituophis* | Cape Gopher Snake |
| *Corallus* | Amazon Tree Boa | *Pituophis* | Bull Snake |
| *Corallus* | Amazon Tree Boa | *Python* | Angolan Python |
| *Corallus* | Amazon Tree Boa | *Python* | Jampea Reticulated Python |
| *Corallus* | Amazon Tree Boa | *Python* | Reticulated Python |
| *Corallus* | Amazon Tree Boa | *Python* | Blood Python |
| *Corallus* | Amazon Tree Boa | *Python* | Ball Python |
| *Corallus* | Amazon Tree Boa | *Rhamphiophis* | Red Beaked Snakes |
| *Corallus* | Amazon Tree Boa | *Spilotes* | Tiger Rat Snake |
| *Corallus* | Amazon Tree Boa | *Toxicodryas* | Blandings Tree Snake |
| *Corallus* | Amazon Tree Boa | *Lampropeltis x Elaphe* HYBRID | California Cornsnake Hybrid |
| *Corallus* | Amazon Tree Boa | *Aspidites x Python* HYBRID | Woma x Ball Python Hyrbid |
| *Corallus* | Amazon Tree Boa | *Xenopeltis* | Sunbeam |
| *Drymarchon* | Unicolor Cribo | *Aspidites* | Woma |
| *Drymarchon* | Unicolor Cribo | *Boa* | Sonoran Boa Constrictor |
| *Drymarchon* | Unicolor Cribo | *Boa* | Boa Constrictor |
| *Drymarchon* | Unicolor Cribo | *Boa* | Tarahumara Boa Constrictor |
| *Drymarchon* | Unicolor Cribo | *Boiga* | Dog Toothed Cat Snake |
| *Drymarchon* | Unicolor Cribo | *Boiruna* | Mussurana (Boiruna maculata) |
| *Drymarchon* | Unicolor Cribo | *Corallus* | Amazon Tree Boa |
| *Drymarchon* | Unicolor Cribo | *Drymarchon* | Black Tailed Cribo |
| *Drymarchon* | Unicolor Cribo | *Drymarchon* | Yellow Tailed Cribo |
| *Drymarchon* | Unicolor Cribo | *Elaphe* | King Rat Snake |
| *Drymarchon* | Unicolor Cribo | *Elaphe* | Chinese Beauty Snake |
| *Drymarchon* | Unicolor Cribo | *Gonionotophis* | Cape File Snake |
| *Drymarchon* | Unicolor Cribo | *Gonionotophis* | West African File Snake |
| *Drymarchon* | Unicolor Cribo | *Heloderma* | Beaded Lizard |
| *Drymarchon* | Unicolor Cribo | *Hydrodynastes* | False Water Cobra |
| *Drymarchon* | Unicolor Cribo | *Lampropeltis* | Honduran Milk Snake |
| *Drymarchon* | Unicolor Cribo | *Lampropeltis* | Speckled Kingsnake |
| *Drymarchon* | Unicolor Cribo | *Lampropeltis* | Atlantic Milk Snake |
| *Drymarchon* | Unicolor Cribo | *Lampropeltis* | Desert Kingsnake |
| *Drymarchon* | Unicolor Cribo | *Lampropeltis* | Eastern Kingsnake |
| *Drymarchon* | Unicolor Cribo | *Lampropeltis* | California Kingsnake |
| *Drymarchon* | Unicolor Cribo | *Lampropeltis* | Andean Milk Snake |
| *Drymarchon* | Unicolor Cribo | *Lampropeltis* | Florida Kingsnake |

*Fig. 1 (cont.)*

| First Snake Species | | Second Snake Species | |
|---|---|---|---|
| Genus | Common Name | Genus | Common Name |
| *Drymarchon* | Unicolor Cribo | *Lampropeltis* | Sinaloan Milk Snake |
| *Drymarchon* | Unicolor Cribo | *Lampropeltis* | Black Milk Snake |
| *Drymarchon* | Unicolor Cribo | *Morelia* | Coastal Carpet Python |
| *Drymarchon* | Unicolor Cribo | *Morelia* | Jaguar Carpet Python |
| *Drymarchon* | Unicolor Cribo | *Morelia* | Darwin Carpet Python |
| *Drymarchon* | Unicolor Cribo | *Morelia* | Irian Jaya Carpet Python |
| *Drymarchon* | Unicolor Cribo | *Morelia* | Carpet Python |
| *Drymarchon* | Unicolor Cribo | *Orthriophis* | Mussurana (Cielia clelia) |
| *Drymarchon* | Unicolor Cribo | *Orthriophis* | Yunnan Beauty Snake |
| *Drymarchon* | Unicolor Cribo | *Pantherophis* | Corn Snake |
| *Drymarchon* | Unicolor Cribo | *Philodryas* | Baron's Racer |
| *Drymarchon* | Unicolor Cribo | *Pituophis* | Sonoran Gopher Snake |
| *Drymarchon* | Unicolor Cribo | *Pituophis* | Cape Gopher Snake |
| *Drymarchon* | Unicolor Cribo | *Pituophis* | Bull Snake |
| *Drymarchon* | Unicolor Cribo | *Python* | Angolan Python |
| *Drymarchon* | Unicolor Cribo | *Python* | Jampea Reticulated Python |
| *Drymarchon* | Unicolor Cribo | *Python* | Reticulated Python |
| *Drymarchon* | Unicolor Cribo | *Python* | Blood Python |
| *Drymarchon* | Unicolor Cribo | *Python* | Ball Python |
| *Drymarchon* | Unicolor Cribo | *Rhamphiophis* | Red Beaked Snakes |
| *Drymarchon* | Unicolor Cribo | *Spilotes* | Tiger Rat Snake |
| *Drymarchon* | Unicolor Cribo | *Toxicodryas* | Blandings Tree Snake |
| *Drymarchon* | Unicolor Cribo | *Lampropeltis x Elaphe* HYBRID | California Cornsnake Hybrid |
| *Drymarchon* | Unicolor Cribo | *Aspidites x Python* HYBRID | Woma x Ball Python Hyrbid |
| *Drymarchon* | Unicolor Cribo | *Xenopeltis* | Sunbeam |
| *Drymarchon* | Black Tailed Cribo | *Aspidites* | Woma |
| *Drymarchon* | Black Tailed Cribo | *Boa* | Sonoran Boa Constrictor |
| *Drymarchon* | Black Tailed Cribo | *Boa* | Boa Constrictor |
| *Drymarchon* | Black Tailed Cribo | *Boa* | Tarahumara Boa Constrictor |
| *Drymarchon* | Black Tailed Cribo | *Boiga* | Dog Toothed Cat Snake |
| *Drymarchon* | Black Tailed Cribo | *Boiruna* | Mussurana (Boiruna maculata) |
| *Drymarchon* | Black Tailed Cribo | *Corallus* | Amazon Tree Boa |
| *Drymarchon* | Black Tailed Cribo | *Drymarchon* | Unicolor Cribo |
| *Drymarchon* | Black Tailed Cribo | *Drymarchon* | Yellow Tailed Cribo |
| *Drymarchon* | Black Tailed Cribo | *Elaphe* | King Rat Snake |
| *Drymarchon* | Black Tailed Cribo | *Elaphe* | Chinese Beauty Snake |
| *Drymarchon* | Black Tailed Cribo | *Gonionotophis* | Cape File Snake |
| *Drymarchon* | Black Tailed Cribo | *Gonionotophis* | West African File Snake |

*Fig. 1 (cont.)*

| First Snake Species | | Second Snake Species | |
| --- | --- | --- | --- |
| Genus | Common Name | Genus | Common Name |
| Drymarchon | Black Tailed Cribo | Heloderma | Beaded Lizard |
| Drymarchon | Black Tailed Cribo | Hydrodynastes | False Water Cobra |
| Drymarchon | Black Tailed Cribo | Lampropeltis | Honduran Milk Snake |
| Drymarchon | Black Tailed Cribo | Lampropeltis | Speckled Kingsnake |
| Drymarchon | Black Tailed Cribo | Lampropeltis | Atlantic Milk Snake |
| Drymarchon | Black Tailed Cribo | Lampropeltis | Desert Kingsnake |
| Drymarchon | Black Tailed Cribo | Lampropeltis | Eastern Kingsnake |
| Drymarchon | Black Tailed Cribo | Lampropeltis | California Kingsnake |
| Drymarchon | Black Tailed Cribo | Lampropeltis | Andean Milk Snake |
| Drymarchon | Black Tailed Cribo | Lampropeltis | Florida Kingsnake |
| Drymarchon | Black Tailed Cribo | Lampropeltis | Sinaloan Milk Snake |
| Drymarchon | Black Tailed Cribo | Lampropeltis | Black Milk Snake |
| Drymarchon | Black Tailed Cribo | Morelia | Coastal Carpet Python |
| Drymarchon | Black Tailed Cribo | Morelia | Jaguar Carpet Python |
| Drymarchon | Black Tailed Cribo | Morelia | Darwin Carpet Python |
| Drymarchon | Black Tailed Cribo | Morelia | Irian Jaya Carpet Python |
| Drymarchon | Black Tailed Cribo | Morelia | Carpet Python |
| Drymarchon | Black Tailed Cribo | Orthriophis | Mussurana (Clelia clelia) |
| Drymarchon | Black Tailed Cribo | Orthriophis | Yunnan Beauty Snake |
| Drymarchon | Black Tailed Cribo | Pantherophis | Corn Snake |
| Drymarchon | Black Tailed Cribo | Philodryas | Baron's Racer |
| Drymarchon | Black Tailed Cribo | Pituophis | Sonoran Gopher Snake |
| Drymarchon | Black Tailed Cribo | Pituophis | Cape Gopher Snake |
| Drymarchon | Black Tailed Cribo | Pituophis | Bull Snake |
| Drymarchon | Black Tailed Cribo | Python | Angolan Python |
| Drymarchon | Black Tailed Cribo | Python | Jampea Reticulated Python |
| Drymarchon | Black Tailed Cribo | Python | Reticulated Python |
| Drymarchon | Black Tailed Cribo | Python | Blood Python |
| Drymarchon | Black Tailed Cribo | Python | Ball Python |
| Drymarchon | Black Tailed Cribo | Rhamphiophis | Red Beaked Snakes |
| Drymarchon | Black Tailed Cribo | Spilotes | Tiger Rat Snake |
| Drymarchon | Black Tailed Cribo | Toxicodryas | Blandings Tree Snake |
| Drymarchon | Black Tailed Cribo | Lampropeltis x Elaphe HYBRID | California Cornsnake Hybrid |
| Drymarchon | Black Tailed Cribo | Aspidites x Python HYBRID | Woma x Ball Python Hyrbid |
| Drymarchon | Black Tailed Cribo | Xenopeltis | Sunbeam |
| Drymarchon | Yellow Tailed Cribo | Aspidites | Woma |
| Drymarchon | Yellow Tailed Cribo | Boa | Sonoran Boa Constrictor |
| Drymarchon | Yellow Tailed Cribo | Boa | Boa Constrictor |

*Fig. 1 (cont.)*

| First Snake Species | | Second Snake Species | |
|---|---|---|---|
| Genus | Common Name | Genus | Common Name |
| *Drymarchon* | Yellow Tailed Cribo | *Boa* | Tarahumara Boa Constrictor |
| *Drymarchon* | Yellow Tailed Cribo | *Boiga* | Dog Toothed Cat Snake |
| *Drymarchon* | Yellow Tailed Cribo | *Boiruna* | Mussurana (Boiruna maculata) |
| *Drymarchon* | Yellow Tailed Cribo | *Corallus* | Amazon Tree Boa |
| *Drymarchon* | Yellow Tailed Cribo | *Drymarchon* | Unicolor Cribo |
| *Drymarchon* | Yellow Tailed Cribo | *Drymarchon* | Black Tailed Cribo |
| *Drymarchon* | Yellow Tailed Cribo | *Elaphe* | King Rat Snake |
| *Drymarchon* | Yellow Tailed Cribo | *Elaphe* | Chinese Beauty Snake |
| *Drymarchon* | Yellow Tailed Cribo | *Gonionotophis* | Cape File Snake |
| *Drymarchon* | Yellow Tailed Cribo | *Gonionotophis* | West African File Snake |
| *Drymarchon* | Yellow Tailed Cribo | *Heloderma* | Beaded Lizard |
| *Drymarchon* | Yellow Tailed Cribo | *Hydrodynastes* | False Water Cobra |
| *Drymarchon* | Yellow Tailed Cribo | *Lampropeltis* | Honduran Milk Snake |
| *Drymarchon* | Yellow Tailed Cribo | *Lampropeltis* | Speckled Kingsnake |
| *Drymarchon* | Yellow Tailed Cribo | *Lampropeltis* | Atlantic Milk Snake |
| *Drymarchon* | Yellow Tailed Cribo | *Lampropeltis* | Desert Kingsnake |
| *Drymarchon* | Yellow Tailed Cribo | *Lampropeltis* | Eastern Kingsnake |
| *Drymarchon* | Yellow Tailed Cribo | *Lampropeltis* | California Kingsnake |
| *Drymarchon* | Yellow Tailed Cribo | *Lampropeltis* | Andean Milk Snake |
| *Drymarchon* | Yellow Tailed Cribo | *Lampropeltis* | Florida Kingsnake |
| *Drymarchon* | Yellow Tailed Cribo | *Lampropeltis* | Sinaloan Milk Snake |
| *Drymarchon* | Yellow Tailed Cribo | *Lampropeltis* | Black Milk Snake |
| *Drymarchon* | Yellow Tailed Cribo | *Morelia* | Coastal Carpet Python |
| *Drymarchon* | Yellow Tailed Cribo | *Morelia* | Jaguar Carpet Python |
| *Drymarchon* | Yellow Tailed Cribo | *Morelia* | Darwin Carpet Python |
| *Drymarchon* | Yellow Tailed Cribo | *Morelia* | Irian Jaya Carpet Python |
| *Drymarchon* | Yellow Tailed Cribo | *Morelia* | Carpet Python |
| *Drymarchon* | Yellow Tailed Cribo | *Orthriophis* | Mussurana (Clelia clelia) |
| *Drymarchon* | Yellow Tailed Cribo | *Orthriophis* | Yunnan Beauty Snake |
| *Drymarchon* | Yellow Tailed Cribo | *Pantherophis* | Corn Snake |
| *Drymarchon* | Yellow Tailed Cribo | *Philodryas* | Baron's Racer |
| *Drymarchon* | Yellow Tailed Cribo | *Pituophis* | Sonoran Gopher Snake |
| *Drymarchon* | Yellow Tailed Cribo | *Pituophis* | Cape Gopher Snake |
| *Drymarchon* | Yellow Tailed Cribo | *Pituophis* | Bull Snake |
| *Drymarchon* | Yellow Tailed Cribo | *Python* | Angolan Python |
| *Drymarchon* | Yellow Tailed Cribo | *Python* | Jampea Reticulated Python |
| *Drymarchon* | Yellow Tailed Cribo | *Python* | Reticulated Python |
| *Drymarchon* | Yellow Tailed Cribo | *Python* | Blood Python |
| *Drymarchon* | Yellow Tailed Cribo | *Python* | Ball Python |
| *Drymarchon* | Yellow Tailed Cribo | *Rhamphiophis* | Red Beaked Snakes |

*Fig. 1 (cont.)*

| First Snake Species | | Second Snake Species | |
|---|---|---|---|
| Genus | Common Name | Genus | Common Name |
| Drymarchon | Yellow Tailed Cribo | Spilotes | Tiger Rat Snake |
| Drymarchon | Yellow Tailed Cribo | Toxicodryas | Blandings Tree Snake |
| Drymarchon | Yellow Tailed Cribo | Lampropeltis x Elaphe HYBRID | California Cornsnake Hybrid |
| Drymarchon | Yellow Tailed Cribo | Aspidites x Python HYBRID | Woma x Ball Python Hyrbid |
| Drymarchon | Yellow Tailed Cribo | Xenopeltis | Sunbeam |
| Elaphe | King Rat Snake | Aspidites | Woma |
| Elaphe | King Rat Snake | Boa | Sonoran Boa Constrictor |
| Elaphe | King Rat Snake | Boa | Boa Constrictor |
| Elaphe | King Rat Snake | Boa | Tarahumara Boa Constrictor |
| Elaphe | King Rat Snake | Boiga | Dog Toothed Cat Snake |
| Elaphe | King Rat Snake | Boiruna | Mussurana (Boiruna maculata) |
| Elaphe | King Rat Snake | Corallus | Amazon Tree Boa |
| Elaphe | King Rat Snake | Drymarchon | Unicolor Cribo |
| Elaphe | King Rat Snake | Drymarchon | Black Tailed Cribo |
| Elaphe | King Rat Snake | Drymarchon | Yellow Tailed Cribo |
| Elaphe | King Rat Snake | Elaphe | Chinese Beauty Snake |
| Elaphe | King Rat Snake | Gonionotophis | Cape File Snake |
| Elaphe | King Rat Snake | Gonionotophis | West African File Snake |
| Elaphe | King Rat Snake | Heloderma | Beaded Lizard |
| Elaphe | King Rat Snake | Hydrodynastes | False Water Cobra |
| Elaphe | King Rat Snake | Lampropeltis | Honduran Milk Snake |
| Elaphe | King Rat Snake | Lampropeltis | Speckled Kingsnake |
| Elaphe | King Rat Snake | Lampropeltis | Atlantic Milk Snake |
| Elaphe | King Rat Snake | Lampropeltis | Desert Kingsnake |
| Elaphe | King Rat Snake | Lampropeltis | Eastern Kingsnake |
| Elaphe | King Rat Snake | Lampropeltis | California Kingsnake |
| Elaphe | King Rat Snake | Lampropeltis | Andean Milk Snake |
| Elaphe | King Rat Snake | Lampropeltis | Florida Kingsnake |
| Elaphe | King Rat Snake | Lampropeltis | Sinaloan Milk Snake |
| Elaphe | King Rat Snake | Lampropeltis | Black Milk Snake |
| Elaphe | King Rat Snake | Morelia | Coastal Carpet Python |
| Elaphe | King Rat Snake | Morelia | Jaguar Carpet Python |
| Elaphe | King Rat Snake | Morelia | Darwin Carpet Python |
| Elaphe | King Rat Snake | Morelia | Irian Jaya Carpet Python |
| Elaphe | King Rat Snake | Morelia | Carpet Python |
| Elaphe | King Rat Snake | Orthriophis | Mussurana (Clelia clelia) |
| Elaphe | King Rat Snake | Orthriophis | Yunnan Beauty Snake |
| Elaphe | King Rat Snake | Pantherophis | Corn Snake |

*Fig. 1 (cont.)*

| First Snake Species | | Second Snake Species | |
|---|---|---|---|
| Genus | Common Name | Genus | Common Name |
| *Elaphe* | King Rat Snake | *Philodryas* | Baron's Racer |
| *Elaphe* | King Rat Snake | *Pituophis* | Sonoran Gopher Snake |
| *Elaphe* | King Rat Snake | *Pituophis* | Cape Gopher Snake |
| *Elaphe* | King Rat Snake | *Pituophis* | Bull Snake |
| *Elaphe* | King Rat Snake | *Python* | Angolan Python |
| *Elaphe* | King Rat Snake | *Python* | Jampea Reticulated Python |
| *Elaphe* | King Rat Snake | *Python* | Reticulated Python |
| *Elaphe* | King Rat Snake | *Python* | Blood Python |
| *Elaphe* | King Rat Snake | *Python* | Ball Python |
| *Elaphe* | King Rat Snake | *Rhamphiophis* | Red Beaked Snakes |
| *Elaphe* | King Rat Snake | *Spilotes* | Tiger Rat Snake |
| *Elaphe* | King Rat Snake | *Toxicodryas* | Blandings Tree Snake |
| *Elaphe* | King Rat Snake | *Lampropeltis x Elaphe* HYBRID | California Cornsnake Hybrid |
| *Elaphe* | King Rat Snake | *Aspidites x Python* HYBRID | Woma x Ball Python Hyrbid |
| *Elaphe* | King Rat Snake | *Xenopeltis* | Sunbeam |
| *Elaphe* | Chinese Beauty Snake | *Aspidites* | Woma |
| *Elaphe* | Chinese Beauty Snake | *Boa* | Sonoran Boa Constrictor |
| *Elaphe* | Chinese Beauty Snake | *Boa* | Boa Constrictor |
| *Elaphe* | Chinese Beauty Snake | *Boa* | Tarahumara Boa Constrictor |
| *Elaphe* | Chinese Beauty Snake | *Boiga* | Dog Toothed Cat Snake |
| *Elaphe* | Chinese Beauty Snake | *Boiruna* | Mussurana (Boiruna maculata) |
| *Elaphe* | Chinese Beauty Snake | *Corallus* | Amazon Tree Boa |
| *Elaphe* | Chinese Beauty Snake | *Drymarchon* | Unicolor Cribo |
| *Elaphe* | Chinese Beauty Snake | *Drymarchon* | Black Tailed Cribo |
| *Elaphe* | Chinese Beauty Snake | *Drymarchon* | Yellow Tailed Cribo |
| *Elaphe* | Chinese Beauty Snake | *Elaphe* | King Rat Snake |
| *Elaphe* | Chinese Beauty Snake | *Gonionotophis* | Cape File Snake |
| *Elaphe* | Chinese Beauty Snake | *Gonionotophis* | West African File Snake |
| *Elaphe* | Chinese Beauty Snake | *Heloderma* | Beaded Lizard |
| *Elaphe* | Chinese Beauty Snake | *Hydrodynastes* | False Water Cobra |
| *Elaphe* | Chinese Beauty Snake | *Lampropeltis* | Honduran Milk Snake |
| *Elaphe* | Chinese Beauty Snake | *Lampropeltis* | Speckled Kingsnake |
| *Elaphe* | Chinese Beauty Snake | *Lampropeltis* | Atlantic Milk Snake |
| *Elaphe* | Chinese Beauty Snake | *Lampropeltis* | Desert Kingsnake |
| *Elaphe* | Chinese Beauty Snake | *Lampropeltis* | Eastern Kingsnake |
| *Elaphe* | Chinese Beauty Snake | *Lampropeltis* | California Kingsnake |
| *Elaphe* | Chinese Beauty Snake | *Lampropeltis* | Andean Milk Snake |
| *Elaphe* | Chinese Beauty Snake | *Lampropeltis* | Florida Kingsnake |

*Fig. 1 (cont.)*

| First Snake Species | | Second Snake Species | |
|---|---|---|---|
| Genus | Common Name | Genus | Common Name |
| *Elaphe* | Chinese Beauty Snake | *Lampropeltis* | Sinaloan Milk Snake |
| *Elaphe* | Chinese Beauty Snake | *Lampropeltis* | Black Milk Snake |
| *Elaphe* | Chinese Beauty Snake | *Morelia* | Coastal Carpet Python |
| *Elaphe* | Chinese Beauty Snake | *Morelia* | Jaguar Carpet Python |
| *Elaphe* | Chinese Beauty Snake | *Morelia* | Darwin Carpet Python |
| *Elaphe* | Chinese Beauty Snake | *Morelia* | Irian Jaya Carpet Python |
| *Elaphe* | Chinese Beauty Snake | *Morelia* | Carpet Python |
| *Elaphe* | Chinese Beauty Snake | *Orthriophis* | Mussurana (Cielia clelia) |
| *Elaphe* | Chinese Beauty Snake | *Orthriophis* | Yunnan Beauty Snake |
| *Elaphe* | Chinese Beauty Snake | *Pantherophis* | Corn Snake |
| *Elaphe* | Chinese Beauty Snake | *Philodryas* | Baron's Racer |
| *Elaphe* | Chinese Beauty Snake | *Pituophis* | Sonoran Gopher Snake |
| *Elaphe* | Chinese Beauty Snake | *Pituophis* | Cape Gopher Snake |
| *Elaphe* | Chinese Beauty Snake | *Pituophis* | Bull Snake |
| *Elaphe* | Chinese Beauty Snake | *Python* | Angolan Python |
| *Elaphe* | Chinese Beauty Snake | *Python* | Jampea Reticulated Python |
| *Elaphe* | Chinese Beauty Snake | *Python* | Reticulated Python |
| *Elaphe* | Chinese Beauty Snake | *Python* | Blood Python |
| *Elaphe* | Chinese Beauty Snake | *Python* | Ball Python |
| *Elaphe* | Chinese Beauty Snake | *Rhamphiophis* | Red Beaked Snakes |
| *Elaphe* | Chinese Beauty Snake | *Spilotes* | Tiger Rat Snake |
| *Elaphe* | Chinese Beauty Snake | *Toxicodryas* | Blandings Tree Snake |
| *Elaphe* | Chinese Beauty Snake | *Lampropeltis x Elaphe* HYBRID | California Cornsnake Hybrid |
| *Elaphe* | Chinese Beauty Snake | *Aspidites x Python* HYBRID | Woma x Ball Python Hyrbid |
| *Elaphe* | Chinese Beauty Snake | *Xenopeltis* | Sunbeam |
| *Gonionotophis* | Cape File Snake | *Aspidites* | Woma |
| *Gonionotophis* | Cape File Snake | *Boa* | Sonoran Boa Constrictor |
| *Gonionotophis* | Cape File Snake | *Boa* | Boa Constrictor |
| *Gonionotophis* | Cape File Snake | *Boa* | Tarahumara Boa Constrictor |
| *Gonionotophis* | Cape File Snake | *Boiga* | Dog Toothed Cat Snake |
| *Gonionotophis* | Cape File Snake | *Boiruna* | Mussurana (Boiruna maculata) |
| *Gonionotophis* | Cape File Snake | *Corallus* | Amazon Tree Boa |
| *Gonionotophis* | Cape File Snake | *Drymarchon* | Unicolor Cribo |
| *Gonionotophis* | Cape File Snake | *Drymarchon* | Black Tailed Cribo |
| *Gonionotophis* | Cape File Snake | *Drymarchon* | Yellow Tailed Cribo |
| *Gonionotophis* | Cape File Snake | *Elaphe* | King Rat Snake |
| *Gonionotophis* | Cape File Snake | *Elaphe* | Chinese Beauty Snake |
| *Gonionotophis* | Cape File Snake | *Gonionotophis* | West African File Snake |

*Fig. 1 (cont.)*

| First Snake Species | | Second Snake Species | |
|---|---|---|---|
| Genus | Common Name | Genus | Common Name |
| *Gonionotophis* | Cape File Snake | *Heloderma* | Beaded Lizard |
| *Gonionotophis* | Cape File Snake | *Hydrodynastes* | False Water Cobra |
| *Gonionotophis* | Cape File Snake | *Lampropeltis* | Honduran Milk Snake |
| *Gonionotophis* | Cape File Snake | *Lampropeltis* | Speckled Kingsnake |
| *Gonionotophis* | Cape File Snake | *Lampropeltis* | Atlantic Milk Snake |
| *Gonionotophis* | Cape File Snake | *Lampropeltis* | Desert Kingsnake |
| *Gonionotophis* | Cape File Snake | *Lampropeltis* | Eastern Kingsnake |
| *Gonionotophis* | Cape File Snake | *Lampropeltis* | California Kingsnake |
| *Gonionotophis* | Cape File Snake | *Lampropeltis* | Andean Milk Snake |
| *Gonionotophis* | Cape File Snake | *Lampropeltis* | Florida Kingsnake |
| *Gonionotophis* | Cape File Snake | *Lampropeltis* | Sinaloan Milk Snake |
| *Gonionotophis* | Cape File Snake | *Lampropeltis* | Black Milk Snake |
| *Gonionotophis* | Cape File Snake | *Morelia* | Coastal Carpet Python |
| *Gonionotophis* | Cape File Snake | *Morelia* | Jaguar Carpet Python |
| *Gonionotophis* | Cape File Snake | *Morelia* | Darwin Carpet Python |
| *Gonionotophis* | Cape File Snake | *Morelia* | Irian Jaya Carpet Python |
| *Gonionotophis* | Cape File Snake | *Morelia* | Carpet Python |
| *Gonionotophis* | Cape File Snake | *Orthriophis* | Mussurana (Clelia clelia) |
| *Gonionotophis* | Cape File Snake | *Orthriophis* | Yunnan Beauty Snake |
| *Gonionotophis* | Cape File Snake | *Pantherophis* | Corn Snake |
| *Gonionotophis* | Cape File Snake | *Philodryas* | Baron's Racer |
| *Gonionotophis* | Cape File Snake | *Pituophis* | Sonoran Gopher Snake |
| *Gonionotophis* | Cape File Snake | *Pituophis* | Cape Gopher Snake |
| *Gonionotophis* | Cape File Snake | *Pituophis* | Bull Snake |
| *Gonionotophis* | Cape File Snake | *Python* | Angolan Python |
| *Gonionotophis* | Cape File Snake | *Python* | Jampea Reticulated Python |
| *Gonionotophis* | Cape File Snake | *Python* | Reticulated Python |
| *Gonionotophis* | Cape File Snake | *Python* | Blood Python |
| *Gonionotophis* | Cape File Snake | *Python* | Ball Python |
| *Gonionotophis* | Cape File Snake | *Rhamphiophis* | Red Beaked Snakes |
| *Gonionotophis* | Cape File Snake | *Spilotes* | Tiger Rat Snake |
| *Gonionotophis* | Cape File Snake | *Toxicodryas* | Blandings Tree Snake |
| *Gonionotophis* | Cape File Snake | *Lampropeltis x Elaphe* HYBRID | California Cornsnake Hybrid |
| *Gonionotophis* | Cape File Snake | *Aspidites x Python* HYBRID | Woma x Ball Python Hyrbid |
| *Gonionotophis* | Cape File Snake | *Xenopeltis* | Sunbeam |
| *Gonionotophis* | West African File Snake | *Aspidites* | Woma |
| *Gonionotophis* | West African File Snake | *Boa* | Sonoran Boa Constrictor |
| *Gonionotophis* | West African File Snake | *Boa* | Boa Constrictor |

*Fig. 1 (cont.)*

| First Snake Species | | Second Snake Species | |
|---|---|---|---|
| Genus | Common Name | Genus | Common Name |
| *Gonionotophis* | West African File Snake | *Boa* | Tarahumara Boa Constrictor |
| *Gonionotophis* | West African File Snake | *Boiga* | Dog Toothed Cat Snake |
| *Gonionotophis* | West African File Snake | *Boiruna* | Mussurana (Boiruna maculata) |
| *Gonionotophis* | West African File Snake | *Corallus* | Amazon Tree Boa |
| *Gonionotophis* | West African File Snake | *Drymarchon* | Unicolor Cribo |
| *Gonionotophis* | West African File Snake | *Drymarchon* | Black Tailed Cribo |
| *Gonionotophis* | West African File Snake | *Drymarchon* | Yellow Tailed Cribo |
| *Gonionotophis* | West African File Snake | *Elaphe* | King Rat Snake |
| *Gonionotophis* | West African File Snake | *Elaphe* | Chinese Beauty Snake |
| *Gonionotophis* | West African File Snake | *Gonionotophis* | Cape File Snake |
| *Gonionotophis* | West African File Snake | *Heloderma* | Beaded Lizard |
| *Gonionotophis* | West African File Snake | *Hydrodynastes* | False Water Cobra |
| *Gonionotophis* | West African File Snake | *Lampropeltis* | Honduran Milk Snake |
| *Gonionotophis* | West African File Snake | *Lampropeltis* | Speckled Kingsnake |
| *Gonionotophis* | West African File Snake | *Lampropeltis* | Atlantic Milk Snake |
| *Gonionotophis* | West African File Snake | *Lampropeltis* | Desert Kingsnake |
| *Gonionotophis* | West African File Snake | *Lampropeltis* | Eastern Kingsnake |
| *Gonionotophis* | West African File Snake | *Lampropeltis* | California Kingsnake |
| *Gonionotophis* | West African File Snake | *Lampropeltis* | Andean Milk Snake |
| *Gonionotophis* | West African File Snake | *Lampropeltis* | Florida Kingsnake |
| *Gonionotophis* | West African File Snake | *Lampropeltis* | Sinaloan Milk Snake |
| *Gonionotophis* | West African File Snake | *Lampropeltis* | Black Milk Snake |
| *Gonionotophis* | West African File Snake | *Morelia* | Coastal Carpet Python |
| *Gonionotophis* | West African File Snake | *Morelia* | Jaguar Carpet Python |
| *Gonionotophis* | West African File Snake | *Morelia* | Darwin Carpet Python |
| *Gonionotophis* | West African File Snake | *Morelia* | Irian Jaya Carpet Python |
| *Gonionotophis* | West African File Snake | *Morelia* | Carpet Python |
| *Gonionotophis* | West African File Snake | *Orthriophis* | Mussurana (Clelia clelia) |
| *Gonionotophis* | West African File Snake | *Orthriophis* | Yunnan Beauty Snake |
| *Gonionotophis* | West African File Snake | *Pantherophis* | Corn Snake |
| *Gonionotophis* | West African File Snake | *Philodryas* | Baron's Racer |
| *Gonionotophis* | West African File Snake | *Pituophis* | Sonoran Gopher Snake |
| *Gonionotophis* | West African File Snake | *Pituophis* | Cape Gopher Snake |
| *Gonionotophis* | West African File Snake | *Pituophis* | Bull Snake |
| *Gonionotophis* | West African File Snake | *Python* | Angolan Python |
| *Gonionotophis* | West African File Snake | *Python* | Jampea Reticulated Python |
| *Gonionotophis* | West African File Snake | *Python* | Reticulated Python |
| *Gonionotophis* | West African File Snake | *Python* | Blood Python |
| *Gonionotophis* | West African File Snake | *Python* | Ball Python |
| *Gonionotophis* | West African File Snake | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Gonionotophis* | West African File Snake | *Spilotes* | Tiger Rat Snake |
| *Gonionotophis* | West African File Snake | *Toxicodryas* | Blandings Tree Snake |
| *Gonionotophis* | West African File Snake | *Lampropeltis x Elaphe* HYBRID | California Cornsnake Hybrid |
| *Gonionotophis* | West African File Snake | *Aspidites x Python* HYBRID | Woma x Ball Python Hyrbid |
| *Gonionotophis* | West African File Snake | *Xenopeltis* | Sunbeam |
| *Heloderma* | Beaded Lizard | *Aspidites* | Woma |
| *Heloderma* | Beaded Lizard | *Boa* | Sonoran Boa Constrictor |
| *Heloderma* | Beaded Lizard | *Boa* | Boa Constrictor |
| *Heloderma* | Beaded Lizard | *Boa* | Tarahumara Boa Constrictor |
| *Heloderma* | Beaded Lizard | *Boiga* | Dog Toothed Cat Snake |
| *Heloderma* | Beaded Lizard | *Boiruna* | Mussurana (Boiruna maculata) |
| *Heloderma* | Beaded Lizard | *Corallus* | Amazon Tree Boa |
| *Heloderma* | Beaded Lizard | *Drymarchon* | Unicolor Cribo |
| *Heloderma* | Beaded Lizard | *Drymarchon* | Black Tailed Cribo |
| *Heloderma* | Beaded Lizard | *Drymarchon* | Yellow Tailed Cribo |
| *Heloderma* | Beaded Lizard | *Elaphe* | King Rat Snake |
| *Heloderma* | Beaded Lizard | *Elaphe* | Chinese Beauty Snake |
| *Heloderma* | Beaded Lizard | *Gonionotophis* | Cape File Snake |
| *Heloderma* | Beaded Lizard | *Gonionotophis* | West African File Snake |
| *Heloderma* | Beaded Lizard | *Hydrodynastes* | False Water Cobra |
| *Heloderma* | Beaded Lizard | *Lampropeltis* | Honduran Milk Snake |
| *Heloderma* | Beaded Lizard | *Lampropeltis* | Speckled Kingsnake |
| *Heloderma* | Beaded Lizard | *Lampropeltis* | Atlantic Milk Snake |
| *Heloderma* | Beaded Lizard | *Lampropeltis* | Desert Kingsnake |
| *Heloderma* | Beaded Lizard | *Lampropeltis* | Eastern Kingsnake |
| *Heloderma* | Beaded Lizard | *Lampropeltis* | California Kingsnake |
| *Heloderma* | Beaded Lizard | *Lampropeltis* | Andean Milk Snake |
| *Heloderma* | Beaded Lizard | *Lampropeltis* | Florida Kingsnake |
| *Heloderma* | Beaded Lizard | *Lampropeltis* | Sinaloan Milk Snake |
| *Heloderma* | Beaded Lizard | *Lampropeltis* | Black Milk Snake |
| *Heloderma* | Beaded Lizard | *Morelia* | Coastal Carpet Python |
| *Heloderma* | Beaded Lizard | *Morelia* | Jaguar Carpet Python |
| *Heloderma* | Beaded Lizard | *Morelia* | Darwin Carpet Python |
| *Heloderma* | Beaded Lizard | *Morelia* | Irian Jaya Carpet Python |
| *Heloderma* | Beaded Lizard | *Morelia* | Carpet Python |
| *Heloderma* | Beaded Lizard | *Orthriophis* | Mussurana (Clelia clelia) |
| *Heloderma* | Beaded Lizard | *Orthriophis* | Yunnan Beauty Snake |
| *Heloderma* | Beaded Lizard | *Pantherophis* | Corn Snake |

*Fig. 1 (cont.)*

| First Snake Species | | Second Snake Species | |
|---|---|---|---|
| Genus | Common Name | Genus | Common Name |
| *Heloderma* | Beaded Lizard | *Philodryas* | Baron's Racer |
| *Heloderma* | Beaded Lizard | *Pituophis* | Sonoran Gopher Snake |
| *Heloderma* | Beaded Lizard | *Pituophis* | Cape Gopher Snake |
| *Heloderma* | Beaded Lizard | *Pituophis* | Bull Snake |
| *Heloderma* | Beaded Lizard | *Python* | Angolan Python |
| *Heloderma* | Beaded Lizard | *Python* | Jampea Reticulated Python |
| *Heloderma* | Beaded Lizard | *Python* | Reticulated Python |
| *Heloderma* | Beaded Lizard | *Python* | Blood Python |
| *Heloderma* | Beaded Lizard | *Python* | Ball Python |
| *Heloderma* | Beaded Lizard | *Rhamphiophis* | Red Beaked Snakes |
| *Heloderma* | Beaded Lizard | *Spilotes* | Tiger Rat Snake |
| *Heloderma* | Beaded Lizard | *Toxicodryas* | Blandings Tree Snake |
| *Heloderma* | Beaded Lizard | *Lampropeltis x Elaphe HYBRID* | California Cornsnake Hybrid |
| *Heloderma* | Beaded Lizard | *Aspidites x Python HYBRID* | Woma x Ball Python Hyrbid |
| *Heloderma* | Beaded Lizard | *Xenopeltis* | Sunbeam |
| *Hydrodynastes* | False Water Cobra | *Aspidites* | Woma |
| *Hydrodynastes* | False Water Cobra | *Boa* | Sonoran Boa Constrictor |
| *Hydrodynastes* | False Water Cobra | *Boa* | Boa Constrictor |
| *Hydrodynastes* | False Water Cobra | *Boa* | Tarahumara Boa Constrictor |
| *Hydrodynastes* | False Water Cobra | *Boiga* | Dog Toothed Cat Snake |
| *Hydrodynastes* | False Water Cobra | *Boiruna* | Mussurana (Boiruna maculata) |
| *Hydrodynastes* | False Water Cobra | *Corallus* | Amazon Tree Boa |
| *Hydrodynastes* | False Water Cobra | *Drymarchon* | Unicolor Cribo |
| *Hydrodynastes* | False Water Cobra | *Drymarchon* | Black Tailed Cribo |
| *Hydrodynastes* | False Water Cobra | *Drymarchon* | Yellow Tailed Cribo |
| *Hydrodynastes* | False Water Cobra | *Elaphe* | King Rat Snake |
| *Hydrodynastes* | False Water Cobra | *Elaphe* | Chinese Beauty Snake |
| *Hydrodynastes* | False Water Cobra | *Gonionotophis* | Cape File Snake |
| *Hydrodynastes* | False Water Cobra | *Gonionotophis* | West African File Snake |
| *Hydrodynastes* | False Water Cobra | *Heloderma* | Beaded Lizard |
| *Hydrodynastes* | False Water Cobra | *Lampropeltis* | Honduran Milk Snake |
| *Hydrodynastes* | False Water Cobra | *Lampropeltis* | Speckled Kingsnake |
| *Hydrodynastes* | False Water Cobra | *Lampropeltis* | Atlantic Milk Snake |
| *Hydrodynastes* | False Water Cobra | *Lampropeltis* | Desert Kingsnake |
| *Hydrodynastes* | False Water Cobra | *Lampropeltis* | Eastern Kingsnake |
| *Hydrodynastes* | False Water Cobra | *Lampropeltis* | California Kingsnake |
| *Hydrodynastes* | False Water Cobra | *Lampropeltis* | Andean Milk Snake |
| *Hydrodynastes* | False Water Cobra | *Lampropeltis* | Florida Kingsnake |

*Fig. 1 (cont.)*

| First Snake Species | | Second Snake Species | |
|---|---|---|---|
| Genus | Common Name | Genus | Common Name |
| *Hydrodynastes* | False Water Cobra | *Lampropeltis* | Sinaloan Milk Snake |
| *Hydrodynastes* | False Water Cobra | *Lampropeltis* | Black Milk Snake |
| *Hydrodynastes* | False Water Cobra | *Morelia* | Coastal Carpet Python |
| *Hydrodynastes* | False Water Cobra | *Morelia* | Jaguar Carpet Python |
| *Hydrodynastes* | False Water Cobra | *Morelia* | Darwin Carpet Python |
| *Hydrodynastes* | False Water Cobra | *Morelia* | Irian Jaya Carpet Python |
| *Hydrodynastes* | False Water Cobra | *Morelia* | Carpet Python |
| *Hydrodynastes* | False Water Cobra | *Orthriophis* | Mussurana (Cielia clelia) |
| *Hydrodynastes* | False Water Cobra | *Orthriophis* | Yunnan Beauty Snake |
| *Hydrodynastes* | False Water Cobra | *Pantherophis* | Corn Snake |
| *Hydrodynastes* | False Water Cobra | *Philodryas* | Baron's Racer |
| *Hydrodynastes* | False Water Cobra | *Pituophis* | Sonoran Gopher Snake |
| *Hydrodynastes* | False Water Cobra | *Pituophis* | Cape Gopher Snake |
| *Hydrodynastes* | False Water Cobra | *Pituophis* | Bull Snake |
| *Hydrodynastes* | False Water Cobra | *Python* | Angolan Python |
| *Hydrodynastes* | False Water Cobra | *Python* | Jampea Reticulated Python |
| *Hydrodynastes* | False Water Cobra | *Python* | Reticulated Python |
| *Hydrodynastes* | False Water Cobra | *Python* | Blood Python |
| *Hydrodynastes* | False Water Cobra | *Python* | Ball Python |
| *Hydrodynastes* | False Water Cobra | *Rhamphiophis* | Red Beaked Snakes |
| *Hydrodynastes* | False Water Cobra | *Spilotes* | Tiger Rat Snake |
| *Hydrodynastes* | False Water Cobra | *Toxicodryas* | Blandings Tree Snake |
| *Hydrodynastes* | False Water Cobra | *Lampropeltis x Elaphe* HYBRID | California Cornsnake Hybrid |
| *Hydrodynastes* | False Water Cobra | *Aspidites x Python* HYBRID | Woma x Ball Python Hyrbid |
| *Hydrodynastes* | False Water Cobra | *Xenopeltis* | Sunbeam |
| *Lampropeltis* | Honduran Milk Snake | *Aspidites* | Woma |
| *Lampropeltis* | Honduran Milk Snake | *Boa* | Sonoran Boa Constrictor |
| *Lampropeltis* | Honduran Milk Snake | *Boa* | Boa Constrictor |
| *Lampropeltis* | Honduran Milk Snake | *Boa* | Tarahumara Boa Constrictor |
| *Lampropeltis* | Honduran Milk Snake | *Boiga* | Dog Toothed Cat Snake |
| *Lampropeltis* | Honduran Milk Snake | *Boiruna* | Mussurana (Boiruna maculata) |
| *Lampropeltis* | Honduran Milk Snake | *Corallus* | Amazon Tree Boa |
| *Lampropeltis* | Honduran Milk Snake | *Drymarchon* | Unicolor Cribo |
| *Lampropeltis* | Honduran Milk Snake | *Drymarchon* | Black Tailed Cribo |
| *Lampropeltis* | Honduran Milk Snake | *Drymarchon* | Yellow Tailed Cribo |
| *Lampropeltis* | Honduran Milk Snake | *Elaphe* | King Rat Snake |
| *Lampropeltis* | Honduran Milk Snake | *Elaphe* | Chinese Beauty Snake |
| *Lampropeltis* | Honduran Milk Snake | *Gonionotophis* | Cape File Snake |

*Fig. 1 (cont.)*

| First Snake Species | | Second Snake Species | |
|---|---|---|---|
| Genus | Common Name | Genus | Common Name |
| *Lampropeltis* | Honduran Milk Snake | *Gonionotophis* | West African File Snake |
| *Lampropeltis* | Honduran Milk Snake | *Heloderma* | Beaded Lizard |
| *Lampropeltis* | Honduran Milk Snake | *Hydrodynastes* | False Water Cobra |
| *Lampropeltis* | Honduran Milk Snake | *Lampropeltis* | Speckled Kingsnake |
| *Lampropeltis* | Honduran Milk Snake | *Lampropeltis* | Atlantic Milk Snake |
| *Lampropeltis* | Honduran Milk Snake | *Lampropeltis* | Desert Kingsnake |
| *Lampropeltis* | Honduran Milk Snake | *Lampropeltis* | Eastern Kingsnake |
| *Lampropeltis* | Honduran Milk Snake | *Lampropeltis* | California Kingsnake |
| *Lampropeltis* | Honduran Milk Snake | *Lampropeltis* | Andean Milk Snake |
| *Lampropeltis* | Honduran Milk Snake | *Lampropeltis* | Florida Kingsnake |
| *Lampropeltis* | Honduran Milk Snake | *Lampropeltis* | Sinaloan Milk Snake |
| *Lampropeltis* | Honduran Milk Snake | *Lampropeltis* | Black Milk Snake |
| *Lampropeltis* | Honduran Milk Snake | *Morelia* | Coastal Carpet Python |
| *Lampropeltis* | Honduran Milk Snake | *Morelia* | Jaguar Carpet Python |
| *Lampropeltis* | Honduran Milk Snake | *Morelia* | Darwin Carpet Python |
| *Lampropeltis* | Honduran Milk Snake | *Morelia* | Irian Jaya Carpet Python |
| *Lampropeltis* | Honduran Milk Snake | *Morelia* | Carpet Python |
| *Lampropeltis* | Honduran Milk Snake | *Orthriophis* | Mussurana (Clelia clelia) |
| *Lampropeltis* | Honduran Milk Snake | *Orthriophis* | Yunnan Beauty Snake |
| *Lampropeltis* | Honduran Milk Snake | *Pantherophis* | Corn Snake |
| *Lampropeltis* | Honduran Milk Snake | *Philodryas* | Baron's Racer |
| *Lampropeltis* | Honduran Milk Snake | *Pituophis* | Sonoran Gopher Snake |
| *Lampropeltis* | Honduran Milk Snake | *Pituophis* | Cape Gopher Snake |
| *Lampropeltis* | Honduran Milk Snake | *Pituophis* | Bull Snake |
| *Lampropeltis* | Honduran Milk Snake | *Python* | Angolan Python |
| *Lampropeltis* | Honduran Milk Snake | *Python* | Jampea Reticulated Python |
| *Lampropeltis* | Honduran Milk Snake | *Python* | Reticulated Python |
| *Lampropeltis* | Honduran Milk Snake | *Python* | Blood Python |
| *Lampropeltis* | Honduran Milk Snake | *Python* | Ball Python |
| *Lampropeltis* | Honduran Milk Snake | *Rhamphiophis* | Red Beaked Snakes |
| *Lampropeltis* | Honduran Milk Snake | *Spilotes* | Tiger Rat Snake |
| *Lampropeltis* | Honduran Milk Snake | *Toxicodryas* | Blandings Tree Snake |
| *Lampropeltis* | Honduran Milk Snake | *Lampropeltis x Elaphe* HYBRID | California Cornsnake Hybrid |
| *Lampropeltis* | Honduran Milk Snake | *Aspidites x Python* HYBRID | Woma x Ball Python Hyrbid |
| *Lampropeltis* | Honduran Milk Snake | *Xenopeltis* | Sunbeam |
| *Lampropeltis* | Speckled Kingsnake | *Aspidites* | Woma |
| *Lampropeltis* | Speckled Kingsnake | *Boa* | Sonoran Boa Constrictor |
| *Lampropeltis* | Speckled Kingsnake | *Boa* | Boa Constrictor |

*Fig. 1 (cont.)*

| First Snake Species | | Second Snake Species | |
|---|---|---|---|
| Genus | Common Name | Genus | Common Name |
| *Lampropeltis* | Speckled Kingsnake | *Boa* | Tarahumara Boa Constrictor |
| *Lampropeltis* | Speckled Kingsnake | *Boiga* | Dog Toothed Cat Snake |
| *Lampropeltis* | Speckled Kingsnake | *Boiruna* | Mussurana (Boiruna maculata) |
| *Lampropeltis* | Speckled Kingsnake | *Corallus* | Amazon Tree Boa |
| *Lampropeltis* | Speckled Kingsnake | *Drymarchon* | Unicolor Cribo |
| *Lampropeltis* | Speckled Kingsnake | *Drymarchon* | Black Tailed Cribo |
| *Lampropeltis* | Speckled Kingsnake | *Drymarchon* | Yellow Tailed Cribo |
| *Lampropeltis* | Speckled Kingsnake | *Elaphe* | King Rat Snake |
| *Lampropeltis* | Speckled Kingsnake | *Elaphe* | Chinese Beauty Snake |
| *Lampropeltis* | Speckled Kingsnake | *Gonionotophis* | Cape File Snake |
| *Lampropeltis* | Speckled Kingsnake | *Gonionotophis* | West African File Snake |
| *Lampropeltis* | Speckled Kingsnake | *Heloderma* | Beaded Lizard |
| *Lampropeltis* | Speckled Kingsnake | *Hydrodynastes* | False Water Cobra |
| *Lampropeltis* | Speckled Kingsnake | *Lampropeltis* | Honduran Milk Snake |
| *Lampropeltis* | Speckled Kingsnake | *Lampropeltis* | Atlantic Milk Snake |
| *Lampropeltis* | Speckled Kingsnake | *Lampropeltis* | Desert Kingsnake |
| *Lampropeltis* | Speckled Kingsnake | *Lampropeltis* | Eastern Kingsnake |
| *Lampropeltis* | Speckled Kingsnake | *Lampropeltis* | California Kingsnake |
| *Lampropeltis* | Speckled Kingsnake | *Lampropeltis* | Andean Milk Snake |
| *Lampropeltis* | Speckled Kingsnake | *Lampropeltis* | Florida Kingsnake |
| *Lampropeltis* | Speckled Kingsnake | *Lampropeltis* | Sinaloan Milk Snake |
| *Lampropeltis* | Speckled Kingsnake | *Lampropeltis* | Black Milk Snake |
| *Lampropeltis* | Speckled Kingsnake | *Morelia* | Coastal Carpet Python |
| *Lampropeltis* | Speckled Kingsnake | *Morelia* | Jaguar Carpet Python |
| *Lampropeltis* | Speckled Kingsnake | *Morelia* | Darwin Carpet Python |
| *Lampropeltis* | Speckled Kingsnake | *Morelia* | Irian Jaya Carpet Python |
| *Lampropeltis* | Speckled Kingsnake | *Morelia* | Carpet Python |
| *Lampropeltis* | Speckled Kingsnake | *Orthriophis* | Mussurana (Clelia clelia) |
| *Lampropeltis* | Speckled Kingsnake | *Orthriophis* | Yunnan Beauty Snake |
| *Lampropeltis* | Speckled Kingsnake | *Pantherophis* | Corn Snake |
| *Lampropeltis* | Speckled Kingsnake | *Philodryas* | Baron's Racer |
| *Lampropeltis* | Speckled Kingsnake | *Pituophis* | Sonoran Gopher Snake |
| *Lampropeltis* | Speckled Kingsnake | *Pituophis* | Cape Gopher Snake |
| *Lampropeltis* | Speckled Kingsnake | *Pituophis* | Bull Snake |
| *Lampropeltis* | Speckled Kingsnake | *Python* | Angolan Python |
| *Lampropeltis* | Speckled Kingsnake | *Python* | Jampea Reticulated Python |
| *Lampropeltis* | Speckled Kingsnake | *Python* | Reticulated Python |
| *Lampropeltis* | Speckled Kingsnake | *Python* | Blood Python |
| *Lampropeltis* | Speckled Kingsnake | *Python* | Ball Python |
| *Lampropeltis* | Speckled Kingsnake | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Lampropeltis* | Speckled Kingsnake | *Spilotes* | Tiger Rat Snake |
| *Lampropeltis* | Speckled Kingsnake | *Toxicodryas* | Blandings Tree Snake |
| *Lampropeltis* | Speckled Kingsnake | *Lampropeltis x Elaphe* HYBRID | California Cornsnake Hybrid |
| *Lampropeltis* | Speckled Kingsnake | *Aspidites x Python* HYBRID | Woma x Ball Python Hyrbid |
| *Lampropeltis* | Speckled Kingsnake | *Xenopeltis* | Sunbeam |
| *Lampropeltis* | Atlantic Milk Snake | *Aspidites* | Woma |
| *Lampropeltis* | Atlantic Milk Snake | *Boa* | Sonoran Boa Constrictor |
| *Lampropeltis* | Atlantic Milk Snake | *Boa* | Boa Constrictor |
| *Lampropeltis* | Atlantic Milk Snake | *Boa* | Tarahumara Boa Constrictor |
| *Lampropeltis* | Atlantic Milk Snake | *Boiga* | Dog Toothed Cat Snake |
| *Lampropeltis* | Atlantic Milk Snake | *Boiruna* | Mussurana (Boiruna maculata) |
| *Lampropeltis* | Atlantic Milk Snake | *Corallus* | Amazon Tree Boa |
| *Lampropeltis* | Atlantic Milk Snake | *Drymarchon* | Unicolor Cribo |
| *Lampropeltis* | Atlantic Milk Snake | *Drymarchon* | Black Tailed Cribo |
| *Lampropeltis* | Atlantic Milk Snake | *Drymarchon* | Yellow Tailed Cribo |
| *Lampropeltis* | Atlantic Milk Snake | *Elaphe* | King Rat Snake |
| *Lampropeltis* | Atlantic Milk Snake | *Elaphe* | Chinese Beauty Snake |
| *Lampropeltis* | Atlantic Milk Snake | *Gonionotophis* | Cape File Snake |
| *Lampropeltis* | Atlantic Milk Snake | *Gonionotophis* | West African File Snake |
| *Lampropeltis* | Atlantic Milk Snake | *Heloderma* | Beaded Lizard |
| *Lampropeltis* | Atlantic Milk Snake | *Hydrodynastes* | False Water Cobra |
| *Lampropeltis* | Atlantic Milk Snake | *Lampropeltis* | Honduran Milk Snake |
| *Lampropeltis* | Atlantic Milk Snake | *Lampropeltis* | Speckled Kingsnake |
| *Lampropeltis* | Atlantic Milk Snake | *Lampropeltis* | Desert Kingsnake |
| *Lampropeltis* | Atlantic Milk Snake | *Lampropeltis* | Eastern Kingsnake |
| *Lampropeltis* | Atlantic Milk Snake | *Lampropeltis* | California Kingsnake |
| *Lampropeltis* | Atlantic Milk Snake | *Lampropeltis* | Andean Milk Snake |
| *Lampropeltis* | Atlantic Milk Snake | *Lampropeltis* | Florida Kingsnake |
| *Lampropeltis* | Atlantic Milk Snake | *Lampropeltis* | Sinaloan Milk Snake |
| *Lampropeltis* | Atlantic Milk Snake | *Lampropeltis* | Black Milk Snake |
| *Lampropeltis* | Atlantic Milk Snake | *Morelia* | Coastal Carpet Python |
| *Lampropeltis* | Atlantic Milk Snake | *Morelia* | Jaguar Carpet Python |
| *Lampropeltis* | Atlantic Milk Snake | *Morelia* | Darwin Carpet Python |
| *Lampropeltis* | Atlantic Milk Snake | *Morelia* | Irian Jaya Carpet Python |
| *Lampropeltis* | Atlantic Milk Snake | *Morelia* | Carpet Python |
| *Lampropeltis* | Atlantic Milk Snake | *Orthriophis* | Mussurana (Clelia clelia) |
| *Lampropeltis* | Atlantic Milk Snake | *Orthriophis* | Yunnan Beauty Snake |
| *Lampropeltis* | Atlantic Milk Snake | *Pantherophis* | Corn Snake |

*Fig. 1 (cont.)*

| First Snake Species | | Second Snake Species | |
|---|---|---|---|
| Genus | Common Name | Genus | Common Name |
| *Lampropeltis* | Atlantic Milk Snake | *Philodryas* | Baron's Racer |
| *Lampropeltis* | Atlantic Milk Snake | *Pituophis* | Sonoran Gopher Snake |
| *Lampropeltis* | Atlantic Milk Snake | *Pituophis* | Cape Gopher Snake |
| *Lampropeltis* | Atlantic Milk Snake | *Pituophis* | Bull Snake |
| *Lampropeltis* | Atlantic Milk Snake | *Python* | Angolan Python |
| *Lampropeltis* | Atlantic Milk Snake | *Python* | Jampea Reticulated Python |
| *Lampropeltis* | Atlantic Milk Snake | *Python* | Reticulated Python |
| *Lampropeltis* | Atlantic Milk Snake | *Python* | Blood Python |
| *Lampropeltis* | Atlantic Milk Snake | *Python* | Ball Python |
| *Lampropeltis* | Atlantic Milk Snake | *Rhamphiophis* | Red Beaked Snakes |
| *Lampropeltis* | Atlantic Milk Snake | *Spilotes* | Tiger Rat Snake |
| *Lampropeltis* | Atlantic Milk Snake | *Toxicodryas* | Blandings Tree Snake |
| *Lampropeltis* | Atlantic Milk Snake | *Lampropeltis x Elaphe* HYBRID | California Cornsnake Hybrid |
| *Lampropeltis* | Atlantic Milk Snake | *Aspidites x Python* HYBRID | Woma x Ball Python Hyrbid |
| *Lampropeltis* | Atlantic Milk Snake | *Xenopeltis* | Sunbeam |
| *Lampropeltis* | Desert Kingsnake | *Aspidites* | Woma |
| *Lampropeltis* | Desert Kingsnake | *Boa* | Sonoran Boa Constrictor |
| *Lampropeltis* | Desert Kingsnake | *Boa* | Boa Constrictor |
| *Lampropeltis* | Desert Kingsnake | *Boa* | Tarahumara Boa Constrictor |
| *Lampropeltis* | Desert Kingsnake | *Boiga* | Dog Toothed Cat Snake |
| *Lampropeltis* | Desert Kingsnake | *Boiruna* | Mussurana (Boiruna maculata) |
| *Lampropeltis* | Desert Kingsnake | *Corallus* | Amazon Tree Boa |
| *Lampropeltis* | Desert Kingsnake | *Drymarchon* | Unicolor Cribo |
| *Lampropeltis* | Desert Kingsnake | *Drymarchon* | Black Tailed Cribo |
| *Lampropeltis* | Desert Kingsnake | *Drymarchon* | Yellow Tailed Cribo |
| *Lampropeltis* | Desert Kingsnake | *Elaphe* | King Rat Snake |
| *Lampropeltis* | Desert Kingsnake | *Elaphe* | Chinese Beauty Snake |
| *Lampropeltis* | Desert Kingsnake | *Gonionotophis* | Cape File Snake |
| *Lampropeltis* | Desert Kingsnake | *Gonionotophis* | West African File Snake |
| *Lampropeltis* | Desert Kingsnake | *Heloderma* | Beaded Lizard |
| *Lampropeltis* | Desert Kingsnake | *Hydrodynastes* | False Water Cobra |
| *Lampropeltis* | Desert Kingsnake | *Lampropeltis* | Honduran Milk Snake |
| *Lampropeltis* | Desert Kingsnake | *Lampropeltis* | Speckled Kingsnake |
| *Lampropeltis* | Desert Kingsnake | *Lampropeltis* | Atlantic Milk Snake |
| *Lampropeltis* | Desert Kingsnake | *Lampropeltis* | Eastern Kingsnake |
| *Lampropeltis* | Desert Kingsnake | *Lampropeltis* | California Kingsnake |
| *Lampropeltis* | Desert Kingsnake | *Lampropeltis* | Andean Milk Snake |
| *Lampropeltis* | Desert Kingsnake | *Lampropeltis* | Florida Kingsnake |

*Fig. 1 (cont.)*

| First Snake Species | | Second Snake Species | |
|---|---|---|---|
| Genus | Common Name | Genus | Common Name |
| *Lampropeltis* | Desert Kingsnake | *Lampropeltis* | Sinaloan Milk Snake |
| *Lampropeltis* | Desert Kingsnake | *Lampropeltis* | Black Milk Snake |
| *Lampropeltis* | Desert Kingsnake | *Morelia* | Coastal Carpet Python |
| *Lampropeltis* | Desert Kingsnake | *Morelia* | Jaguar Carpet Python |
| *Lampropeltis* | Desert Kingsnake | *Morelia* | Darwin Carpet Python |
| *Lampropeltis* | Desert Kingsnake | *Morelia* | Irian Jaya Carpet Python |
| *Lampropeltis* | Desert Kingsnake | *Morelia* | Carpet Python |
| *Lampropeltis* | Desert Kingsnake | *Orthriophis* | Mussurana (Cielia clelia) |
| *Lampropeltis* | Desert Kingsnake | *Orthriophis* | Yunnan Beauty Snake |
| *Lampropeltis* | Desert Kingsnake | *Pantherophis* | Corn Snake |
| *Lampropeltis* | Desert Kingsnake | *Philodryas* | Baron's Racer |
| *Lampropeltis* | Desert Kingsnake | *Pituophis* | Sonoran Gopher Snake |
| *Lampropeltis* | Desert Kingsnake | *Pituophis* | Cape Gopher Snake |
| *Lampropeltis* | Desert Kingsnake | *Pituophis* | Bull Snake |
| *Lampropeltis* | Desert Kingsnake | *Python* | Angolan Python |
| *Lampropeltis* | Desert Kingsnake | *Python* | Jampea Reticulated Python |
| *Lampropeltis* | Desert Kingsnake | *Python* | Reticulated Python |
| *Lampropeltis* | Desert Kingsnake | *Python* | Blood Python |
| *Lampropeltis* | Desert Kingsnake | *Python* | Ball Python |
| *Lampropeltis* | Desert Kingsnake | *Rhamphiophis* | Red Beaked Snakes |
| *Lampropeltis* | Desert Kingsnake | *Spilotes* | Tiger Rat Snake |
| *Lampropeltis* | Desert Kingsnake | *Toxicodryas* | Blandings Tree Snake |
| *Lampropeltis* | Desert Kingsnake | *Lampropeltis x Elaphe* HYBRID | California Cornsnake Hybrid |
| *Lampropeltis* | Desert Kingsnake | *Aspidites x Python* HYBRID | Woma x Ball Python Hyrbid |
| *Lampropeltis* | Desert Kingsnake | *Xenopeltis* | Sunbeam |
| *Lampropeltis* | Eastern Kingsnake | *Aspidites* | Woma |
| *Lampropeltis* | Eastern Kingsnake | *Boa* | Sonoran Boa Constrictor |
| *Lampropeltis* | Eastern Kingsnake | *Boa* | Boa Constrictor |
| *Lampropeltis* | Eastern Kingsnake | *Boa* | Tarahumara Boa Constrictor |
| *Lampropeltis* | Eastern Kingsnake | *Boiga* | Dog Toothed Cat Snake |
| *Lampropeltis* | Eastern Kingsnake | *Boiruna* | Mussurana (Boiruna maculata) |
| *Lampropeltis* | Eastern Kingsnake | *Corallus* | Amazon Tree Boa |
| *Lampropeltis* | Eastern Kingsnake | *Drymarchon* | Unicolor Cribo |
| *Lampropeltis* | Eastern Kingsnake | *Drymarchon* | Black Tailed Cribo |
| *Lampropeltis* | Eastern Kingsnake | *Drymarchon* | Yellow Tailed Cribo |
| *Lampropeltis* | Eastern Kingsnake | *Elaphe* | King Rat Snake |
| *Lampropeltis* | Eastern Kingsnake | *Elaphe* | Chinese Beauty Snake |
| *Lampropeltis* | Eastern Kingsnake | *Gonionotophis* | Cape File Snake |

*Fig. 1 (cont.)*

| First Snake Species | | Second Snake Species | |
|---|---|---|---|
| Genus | Common Name | Genus | Common Name |
| *Lampropeltis* | Eastern Kingsnake | *Gonionotophis* | West African File Snake |
| *Lampropeltis* | Eastern Kingsnake | *Heloderma* | Beaded Lizard |
| *Lampropeltis* | Eastern Kingsnake | *Hydrodynastes* | False Water Cobra |
| *Lampropeltis* | Eastern Kingsnake | *Lampropeltis* | Honduran Milk Snake |
| *Lampropeltis* | Eastern Kingsnake | *Lampropeltis* | Speckled Kingsnake |
| *Lampropeltis* | Eastern Kingsnake | *Lampropeltis* | Atlantic Milk Snake |
| *Lampropeltis* | Eastern Kingsnake | *Lampropeltis* | Desert Kingsnake |
| *Lampropeltis* | Eastern Kingsnake | *Lampropeltis* | California Kingsnake |
| *Lampropeltis* | Eastern Kingsnake | *Lampropeltis* | Andean Milk Snake |
| *Lampropeltis* | Eastern Kingsnake | *Lampropeltis* | Florida Kingsnake |
| *Lampropeltis* | Eastern Kingsnake | *Lampropeltis* | Sinaloan Milk Snake |
| *Lampropeltis* | Eastern Kingsnake | *Lampropeltis* | Black Milk Snake |
| *Lampropeltis* | Eastern Kingsnake | *Morelia* | Coastal Carpet Python |
| *Lampropeltis* | Eastern Kingsnake | *Morelia* | Jaguar Carpet Python |
| *Lampropeltis* | Eastern Kingsnake | *Morelia* | Darwin Carpet Python |
| *Lampropeltis* | Eastern Kingsnake | *Morelia* | Irian Jaya Carpet Python |
| *Lampropeltis* | Eastern Kingsnake | *Morelia* | Carpet Python |
| *Lampropeltis* | Eastern Kingsnake | *Orthriophis* | Mussurana (Clelia clelia) |
| *Lampropeltis* | Eastern Kingsnake | *Orthriophis* | Yunnan Beauty Snake |
| *Lampropeltis* | Eastern Kingsnake | *Pantherophis* | Corn Snake |
| *Lampropeltis* | Eastern Kingsnake | *Philodryas* | Baron's Racer |
| *Lampropeltis* | Eastern Kingsnake | *Pituophis* | Sonoran Gopher Snake |
| *Lampropeltis* | Eastern Kingsnake | *Pituophis* | Cape Gopher Snake |
| *Lampropeltis* | Eastern Kingsnake | *Pituophis* | Bull Snake |
| *Lampropeltis* | Eastern Kingsnake | *Python* | Angolan Python |
| *Lampropeltis* | Eastern Kingsnake | *Python* | Jampea Reticulated Python |
| *Lampropeltis* | Eastern Kingsnake | *Python* | Reticulated Python |
| *Lampropeltis* | Eastern Kingsnake | *Python* | Blood Python |
| *Lampropeltis* | Eastern Kingsnake | *Python* | Ball Python |
| *Lampropeltis* | Eastern Kingsnake | *Rhamphiophis* | Red Beaked Snakes |
| *Lampropeltis* | Eastern Kingsnake | *Spilotes* | Tiger Rat Snake |
| *Lampropeltis* | Eastern Kingsnake | *Toxicodryas* | Blandings Tree Snake |
| *Lampropeltis* | Eastern Kingsnake | *Lampropeltis x Elaphe* HYBRID | California Cornsnake Hybrid |
| *Lampropeltis* | Eastern Kingsnake | *Aspidites x Python* HYBRID | Woma x Ball Python Hyrbid |
| *Lampropeltis* | Eastern Kingsnake | *Xenopeltis* | Sunbeam |
| *Lampropeltis* | California Kingsnake | *Aspidites* | Woma |
| *Lampropeltis* | California Kingsnake | *Boa* | Sonoran Boa Constrictor |
| *Lampropeltis* | California Kingsnake | *Boa* | Boa Constrictor |

*Fig. 1 (cont.)*

| First Snake Species | | Second Snake Species | |
|---|---|---|---|
| Genus | Common Name | Genus | Common Name |
| *Lampropeltis* | California Kingsnake | *Boa* | Tarahumara Boa Constrictor |
| *Lampropeltis* | California Kingsnake | *Boiga* | Dog Toothed Cat Snake |
| *Lampropeltis* | California Kingsnake | *Boiruna* | Mussurana (Boiruna maculata) |
| *Lampropeltis* | California Kingsnake | *Corallus* | Amazon Tree Boa |
| *Lampropeltis* | California Kingsnake | *Drymarchon* | Unicolor Cribo |
| *Lampropeltis* | California Kingsnake | *Drymarchon* | Black Tailed Cribo |
| *Lampropeltis* | California Kingsnake | *Drymarchon* | Yellow Tailed Cribo |
| *Lampropeltis* | California Kingsnake | *Elaphe* | King Rat Snake |
| *Lampropeltis* | California Kingsnake | *Elaphe* | Chinese Beauty Snake |
| *Lampropeltis* | California Kingsnake | *Gonionotophis* | Cape File Snake |
| *Lampropeltis* | California Kingsnake | *Gonionotophis* | West African File Snake |
| *Lampropeltis* | California Kingsnake | *Heloderma* | Beaded Lizard |
| *Lampropeltis* | California Kingsnake | *Hydrodynastes* | False Water Cobra |
| *Lampropeltis* | California Kingsnake | *Lampropeltis* | Honduran Milk Snake |
| *Lampropeltis* | California Kingsnake | *Lampropeltis* | Speckled Kingsnake |
| *Lampropeltis* | California Kingsnake | *Lampropeltis* | Atlantic Milk Snake |
| *Lampropeltis* | California Kingsnake | *Lampropeltis* | Desert Kingsnake |
| *Lampropeltis* | California Kingsnake | *Lampropeltis* | Eastern Kingsnake |
| *Lampropeltis* | California Kingsnake | *Lampropeltis* | Andean Milk Snake |
| *Lampropeltis* | California Kingsnake | *Lampropeltis* | Florida Kingsnake |
| *Lampropeltis* | California Kingsnake | *Lampropeltis* | Sinaloan Milk Snake |
| *Lampropeltis* | California Kingsnake | *Lampropeltis* | Black Milk Snake |
| *Lampropeltis* | California Kingsnake | *Morelia* | Coastal Carpet Python |
| *Lampropeltis* | California Kingsnake | *Morelia* | Jaguar Carpet Python |
| *Lampropeltis* | California Kingsnake | *Morelia* | Darwin Carpet Python |
| *Lampropeltis* | California Kingsnake | *Morelia* | Irian Jaya Carpet Python |
| *Lampropeltis* | California Kingsnake | *Morelia* | Carpet Python |
| *Lampropeltis* | California Kingsnake | *Orthriophis* | Mussurana (Clelia clelia) |
| *Lampropeltis* | California Kingsnake | *Orthriophis* | Yunnan Beauty Snake |
| *Lampropeltis* | California Kingsnake | *Pantherophis* | Corn Snake |
| *Lampropeltis* | California Kingsnake | *Philodryas* | Baron's Racer |
| *Lampropeltis* | California Kingsnake | *Pituophis* | Sonoran Gopher Snake |
| *Lampropeltis* | California Kingsnake | *Pituophis* | Cape Gopher Snake |
| *Lampropeltis* | California Kingsnake | *Pituophis* | Bull Snake |
| *Lampropeltis* | California Kingsnake | *Python* | Angolan Python |
| *Lampropeltis* | California Kingsnake | *Python* | Jampea Reticulated Python |
| *Lampropeltis* | California Kingsnake | *Python* | Reticulated Python |
| *Lampropeltis* | California Kingsnake | *Python* | Blood Python |
| *Lampropeltis* | California Kingsnake | *Python* | Ball Python |
| *Lampropeltis* | California Kingsnake | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Lampropeltis* | California Kingsnake | *Spilotes* | Tiger Rat Snake |
| *Lampropeltis* | California Kingsnake | *Toxicodryas* | Blandings Tree Snake |
| *Lampropeltis* | California Kingsnake | *Lampropeltis x Elaphe* HYBRID | California Cornsnake Hybrid |
| *Lampropeltis* | California Kingsnake | *Aspidites x Python* HYBRID | Woma x Ball Python Hyrbid |
| *Lampropeltis* | California Kingsnake | *Xenopeltis* | Sunbeam |
| *Lampropeltis* | Andean Milk Snake | *Aspidites* | Woma |
| *Lampropeltis* | Andean Milk Snake | *Boa* | Sonoran Boa Constrictor |
| *Lampropeltis* | Andean Milk Snake | *Boa* | Boa Constrictor |
| *Lampropeltis* | Andean Milk Snake | *Boa* | Tarahumara Boa Constrictor |
| *Lampropeltis* | Andean Milk Snake | *Boiga* | Dog Toothed Cat Snake |
| *Lampropeltis* | Andean Milk Snake | *Boiruna* | Mussurana (Boiruna maculata) |
| *Lampropeltis* | Andean Milk Snake | *Corallus* | Amazon Tree Boa |
| *Lampropeltis* | Andean Milk Snake | *Drymarchon* | Unicolor Cribo |
| *Lampropeltis* | Andean Milk Snake | *Drymarchon* | Black Tailed Cribo |
| *Lampropeltis* | Andean Milk Snake | *Drymarchon* | Yellow Tailed Cribo |
| *Lampropeltis* | Andean Milk Snake | *Elaphe* | King Rat Snake |
| *Lampropeltis* | Andean Milk Snake | *Elaphe* | Chinese Beauty Snake |
| *Lampropeltis* | Andean Milk Snake | *Gonionotophis* | Cape File Snake |
| *Lampropeltis* | Andean Milk Snake | *Gonionotophis* | West African File Snake |
| *Lampropeltis* | Andean Milk Snake | *Heloderma* | Beaded Lizard |
| *Lampropeltis* | Andean Milk Snake | *Hydrodynastes* | False Water Cobra |
| *Lampropeltis* | Andean Milk Snake | *Lampropeltis* | Honduran Milk Snake |
| *Lampropeltis* | Andean Milk Snake | *Lampropeltis* | Speckled Kingsnake |
| *Lampropeltis* | Andean Milk Snake | *Lampropeltis* | Atlantic Milk Snake |
| *Lampropeltis* | Andean Milk Snake | *Lampropeltis* | Desert Kingsnake |
| *Lampropeltis* | Andean Milk Snake | *Lampropeltis* | Eastern Kingsnake |
| *Lampropeltis* | Andean Milk Snake | *Lampropeltis* | California Kingsnake |
| *Lampropeltis* | Andean Milk Snake | *Lampropeltis* | Florida Kingsnake |
| *Lampropeltis* | Andean Milk Snake | *Lampropeltis* | Sinaloan Milk Snake |
| *Lampropeltis* | Andean Milk Snake | *Lampropeltis* | Black Milk Snake |
| *Lampropeltis* | Andean Milk Snake | *Morelia* | Coastal Carpet Python |
| *Lampropeltis* | Andean Milk Snake | *Morelia* | Jaguar Carpet Python |
| *Lampropeltis* | Andean Milk Snake | *Morelia* | Darwin Carpet Python |
| *Lampropeltis* | Andean Milk Snake | *Morelia* | Irian Jaya Carpet Python |
| *Lampropeltis* | Andean Milk Snake | *Morelia* | Carpet Python |
| *Lampropeltis* | Andean Milk Snake | *Orthriophis* | Mussurana (Clelia clelia) |
| *Lampropeltis* | Andean Milk Snake | *Orthriophis* | Yunnan Beauty Snake |
| *Lampropeltis* | Andean Milk Snake | *Pantherophis* | Corn Snake |

*Fig. 1 (cont.)*

| First Snake Species | | Second Snake Species | |
|---|---|---|---|
| Genus | Common Name | Genus | Common Name |
| *Lampropeltis* | Andean Milk Snake | *Philodryas* | Baron's Racer |
| *Lampropeltis* | Andean Milk Snake | *Pituophis* | Sonoran Gopher Snake |
| *Lampropeltis* | Andean Milk Snake | *Pituophis* | Cape Gopher Snake |
| *Lampropeltis* | Andean Milk Snake | *Pituophis* | Bull Snake |
| *Lampropeltis* | Andean Milk Snake | *Python* | Angolan Python |
| *Lampropeltis* | Andean Milk Snake | *Python* | Jampea Reticulated Python |
| *Lampropeltis* | Andean Milk Snake | *Python* | Reticulated Python |
| *Lampropeltis* | Andean Milk Snake | *Python* | Blood Python |
| *Lampropeltis* | Andean Milk Snake | *Python* | Ball Python |
| *Lampropeltis* | Andean Milk Snake | *Rhamphiophis* | Red Beaked Snakes |
| *Lampropeltis* | Andean Milk Snake | *Spilotes* | Tiger Rat Snake |
| *Lampropeltis* | Andean Milk Snake | *Toxicodryas* | Blandings Tree Snake |
| *Lampropeltis* | Andean Milk Snake | *Lampropeltis x Elaphe* HYBRID | California Cornsnake Hybrid |
| *Lampropeltis* | Andean Milk Snake | *Aspidites x Python* HYBRID | Woma x Ball Python Hyrbid |
| *Lampropeltis* | Andean Milk Snake | *Xenopeltis* | Sunbeam |
| *Lampropeltis* | Florida Kingsnake | *Aspidites* | Woma |
| *Lampropeltis* | Florida Kingsnake | *Boa* | Sonoran Boa Constrictor |
| *Lampropeltis* | Florida Kingsnake | *Boa* | Boa Constrictor |
| *Lampropeltis* | Florida Kingsnake | *Boa* | Tarahumara Boa Constrictor |
| *Lampropeltis* | Florida Kingsnake | *Boiga* | Dog Toothed Cat Snake |
| *Lampropeltis* | Florida Kingsnake | *Boiruna* | Mussurana (Boiruna maculata) |
| *Lampropeltis* | Florida Kingsnake | *Corallus* | Amazon Tree Boa |
| *Lampropeltis* | Florida Kingsnake | *Drymarchon* | Unicolor Cribo |
| *Lampropeltis* | Florida Kingsnake | *Drymarchon* | Black Tailed Cribo |
| *Lampropeltis* | Florida Kingsnake | *Drymarchon* | Yellow Tailed Cribo |
| *Lampropeltis* | Florida Kingsnake | *Elaphe* | King Rat Snake |
| *Lampropeltis* | Florida Kingsnake | *Elaphe* | Chinese Beauty Snake |
| *Lampropeltis* | Florida Kingsnake | *Gonionotophis* | Cape File Snake |
| *Lampropeltis* | Florida Kingsnake | *Gonionotophis* | West African File Snake |
| *Lampropeltis* | Florida Kingsnake | *Heloderma* | Beaded Lizard |
| *Lampropeltis* | Florida Kingsnake | *Hydrodynastes* | False Water Cobra |
| *Lampropeltis* | Florida Kingsnake | *Lampropeltis* | Honduran Milk Snake |
| *Lampropeltis* | Florida Kingsnake | *Lampropeltis* | Speckled Kingsnake |
| *Lampropeltis* | Florida Kingsnake | *Lampropeltis* | Atlantic Milk Snake |
| *Lampropeltis* | Florida Kingsnake | *Lampropeltis* | Desert Kingsnake |
| *Lampropeltis* | Florida Kingsnake | *Lampropeltis* | Eastern Kingsnake |
| *Lampropeltis* | Florida Kingsnake | *Lampropeltis* | California Kingsnake |
| *Lampropeltis* | Florida Kingsnake | *Lampropeltis* | Andean Milk Snake |

*Fig. 1 (cont.)*

| First Snake Species | | Second Snake Species | |
|---|---|---|---|
| Genus | Common Name | Genus | Common Name |
| *Lampropeltis* | Florida Kingsnake | *Lampropeltis* | Sinaloan Milk Snake |
| *Lampropeltis* | Florida Kingsnake | *Lampropeltis* | Black Milk Snake |
| *Lampropeltis* | Florida Kingsnake | *Morelia* | Coastal Carpet Python |
| *Lampropeltis* | Florida Kingsnake | *Morelia* | Jaguar Carpet Python |
| *Lampropeltis* | Florida Kingsnake | *Morelia* | Darwin Carpet Python |
| *Lampropeltis* | Florida Kingsnake | *Morelia* | Irian Jaya Carpet Python |
| *Lampropeltis* | Florida Kingsnake | *Morelia* | Carpet Python |
| *Lampropeltis* | Florida Kingsnake | *Orthriophis* | Mussurana (Cielia clelia) |
| *Lampropeltis* | Florida Kingsnake | *Orthriophis* | Yunnan Beauty Snake |
| *Lampropeltis* | Florida Kingsnake | *Pantherophis* | Corn Snake |
| *Lampropeltis* | Florida Kingsnake | *Philodryas* | Baron's Racer |
| *Lampropeltis* | Florida Kingsnake | *Pituophis* | Sonoran Gopher Snake |
| *Lampropeltis* | Florida Kingsnake | *Pituophis* | Cape Gopher Snake |
| *Lampropeltis* | Florida Kingsnake | *Pituophis* | Bull Snake |
| *Lampropeltis* | Florida Kingsnake | *Python* | Angolan Python |
| *Lampropeltis* | Florida Kingsnake | *Python* | Jampea Reticulated Python |
| *Lampropeltis* | Florida Kingsnake | *Python* | Reticulated Python |
| *Lampropeltis* | Florida Kingsnake | *Python* | Blood Python |
| *Lampropeltis* | Florida Kingsnake | *Python* | Ball Python |
| *Lampropeltis* | Florida Kingsnake | *Rhamphiophis* | Red Beaked Snakes |
| *Lampropeltis* | Florida Kingsnake | *Spilotes* | Tiger Rat Snake |
| *Lampropeltis* | Florida Kingsnake | *Toxicodryas* | Blandings Tree Snake |
| *Lampropeltis* | Florida Kingsnake | *Lampropeltis x Elaphe* HYBRID | California Cornsnake Hybrid |
| *Lampropeltis* | Florida Kingsnake | *Aspidites x Python* HYBRID | Woma x Ball Python Hyrbid |
| *Lampropeltis* | Florida Kingsnake | *Xenopeltis* | Sunbeam |
| *Lampropeltis* | Sinaloan Milk Snake | *Aspidites* | Woma |
| *Lampropeltis* | Sinaloan Milk Snake | *Boa* | Sonoran Boa Constrictor |
| *Lampropeltis* | Sinaloan Milk Snake | *Boa* | Boa Constrictor |
| *Lampropeltis* | Sinaloan Milk Snake | *Boa* | Tarahumara Boa Constrictor |
| *Lampropeltis* | Sinaloan Milk Snake | *Boiga* | Dog Toothed Cat Snake |
| *Lampropeltis* | Sinaloan Milk Snake | *Boiruna* | Mussurana (Boiruna maculata) |
| *Lampropeltis* | Sinaloan Milk Snake | *Corallus* | Amazon Tree Boa |
| *Lampropeltis* | Sinaloan Milk Snake | *Drymarchon* | Unicolor Cribo |
| *Lampropeltis* | Sinaloan Milk Snake | *Drymarchon* | Black Tailed Cribo |
| *Lampropeltis* | Sinaloan Milk Snake | *Drymarchon* | Yellow Tailed Cribo |
| *Lampropeltis* | Sinaloan Milk Snake | *Elaphe* | King Rat Snake |
| *Lampropeltis* | Sinaloan Milk Snake | *Elaphe* | Chinese Beauty Snake |
| *Lampropeltis* | Sinaloan Milk Snake | *Gonionotophis* | Cape File Snake |

*Fig. 1 (cont.)*

| First Snake Species | | Second Snake Species | |
|---|---|---|---|
| Genus | Common Name | Genus | Common Name |
| *Lampropeltis* | Sinaloan Milk Snake | *Gonionotophis* | West African File Snake |
| *Lampropeltis* | Sinaloan Milk Snake | *Heloderma* | Beaded Lizard |
| *Lampropeltis* | Sinaloan Milk Snake | *Hydrodynastes* | False Water Cobra |
| *Lampropeltis* | Sinaloan Milk Snake | *Lampropeltis* | Honduran Milk Snake |
| *Lampropeltis* | Sinaloan Milk Snake | *Lampropeltis* | Speckled Kingsnake |
| *Lampropeltis* | Sinaloan Milk Snake | *Lampropeltis* | Atlantic Milk Snake |
| *Lampropeltis* | Sinaloan Milk Snake | *Lampropeltis* | Desert Kingsnake |
| *Lampropeltis* | Sinaloan Milk Snake | *Lampropeltis* | Eastern Kingsnake |
| *Lampropeltis* | Sinaloan Milk Snake | *Lampropeltis* | California Kingsnake |
| *Lampropeltis* | Sinaloan Milk Snake | *Lampropeltis* | Andean Milk Snake |
| *Lampropeltis* | Sinaloan Milk Snake | *Lampropeltis* | Florida Kingsnake |
| *Lampropeltis* | Sinaloan Milk Snake | *Lampropeltis* | Black Milk Snake |
| *Lampropeltis* | Sinaloan Milk Snake | *Morelia* | Coastal Carpet Python |
| *Lampropeltis* | Sinaloan Milk Snake | *Morelia* | Jaguar Carpet Python |
| *Lampropeltis* | Sinaloan Milk Snake | *Morelia* | Darwin Carpet Python |
| *Lampropeltis* | Sinaloan Milk Snake | *Morelia* | Irian Jaya Carpet Python |
| *Lampropeltis* | Sinaloan Milk Snake | *Morelia* | Carpet Python |
| *Lampropeltis* | Sinaloan Milk Snake | *Orthriophis* | Mussurana (Clelia clelia) |
| *Lampropeltis* | Sinaloan Milk Snake | *Orthriophis* | Yunnan Beauty Snake |
| *Lampropeltis* | Sinaloan Milk Snake | *Pantherophis* | Corn Snake |
| *Lampropeltis* | Sinaloan Milk Snake | *Philodryas* | Baron's Racer |
| *Lampropeltis* | Sinaloan Milk Snake | *Pituophis* | Sonoran Gopher Snake |
| *Lampropeltis* | Sinaloan Milk Snake | *Pituophis* | Cape Gopher Snake |
| *Lampropeltis* | Sinaloan Milk Snake | *Pituophis* | Bull Snake |
| *Lampropeltis* | Sinaloan Milk Snake | *Python* | Angolan Python |
| *Lampropeltis* | Sinaloan Milk Snake | *Python* | Jampea Reticulated Python |
| *Lampropeltis* | Sinaloan Milk Snake | *Python* | Reticulated Python |
| *Lampropeltis* | Sinaloan Milk Snake | *Python* | Blood Python |
| *Lampropeltis* | Sinaloan Milk Snake | *Python* | Ball Python |
| *Lampropeltis* | Sinaloan Milk Snake | *Rhamphiophis* | Red Beaked Snakes |
| *Lampropeltis* | Sinaloan Milk Snake | *Spilotes* | Tiger Rat Snake |
| *Lampropeltis* | Sinaloan Milk Snake | *Toxicodryas* | Blandings Tree Snake |
| *Lampropeltis* | Sinaloan Milk Snake | *Lampropeltis x Elaphe* HYBRID | California Cornsnake Hybrid |
| *Lampropeltis* | Sinaloan Milk Snake | *Aspidites x Python* HYBRID | Woma x Ball Python Hyrbid |
| *Lampropeltis* | Sinaloan Milk Snake | *Xenopeltis* | Sunbeam |
| *Lampropeltis* | Black Milk Snake | *Aspidites* | Woma |
| *Lampropeltis* | Black Milk Snake | *Boa* | Sonoran Boa Constrictor |
| *Lampropeltis* | Black Milk Snake | *Boa* | Boa Constrictor |

*Fig. 1 (cont.)*

| First Snake Species | | Second Snake Species | |
|---|---|---|---|
| Genus | Common Name | Genus | Common Name |
| *Lampropeltis* | Black Milk Snake | *Boa* | Tarahumara Boa Constrictor |
| *Lampropeltis* | Black Milk Snake | *Boiga* | Dog Toothed Cat Snake |
| *Lampropeltis* | Black Milk Snake | *Boiruna* | Mussurana (Boiruna maculata) |
| *Lampropeltis* | Black Milk Snake | *Corallus* | Amazon Tree Boa |
| *Lampropeltis* | Black Milk Snake | *Drymarchon* | Unicolor Cribo |
| *Lampropeltis* | Black Milk Snake | *Drymarchon* | Black Tailed Cribo |
| *Lampropeltis* | Black Milk Snake | *Drymarchon* | Yellow Tailed Cribo |
| *Lampropeltis* | Black Milk Snake | *Elaphe* | King Rat Snake |
| *Lampropeltis* | Black Milk Snake | *Elaphe* | Chinese Beauty Snake |
| *Lampropeltis* | Black Milk Snake | *Gonionotophis* | Cape File Snake |
| *Lampropeltis* | Black Milk Snake | *Gonionotophis* | West African File Snake |
| *Lampropeltis* | Black Milk Snake | *Heloderma* | Beaded Lizard |
| *Lampropeltis* | Black Milk Snake | *Hydrodynastes* | False Water Cobra |
| *Lampropeltis* | Black Milk Snake | *Lampropeltis* | Honduran Milk Snake |
| *Lampropeltis* | Black Milk Snake | *Lampropeltis* | Speckled Kingsnake |
| *Lampropeltis* | Black Milk Snake | *Lampropeltis* | Atlantic Milk Snake |
| *Lampropeltis* | Black Milk Snake | *Lampropeltis* | Desert Kingsnake |
| *Lampropeltis* | Black Milk Snake | *Lampropeltis* | Eastern Kingsnake |
| *Lampropeltis* | Black Milk Snake | *Lampropeltis* | California Kingsnake |
| *Lampropeltis* | Black Milk Snake | *Lampropeltis* | Andean Milk Snake |
| *Lampropeltis* | Black Milk Snake | *Lampropeltis* | Florida Kingsnake |
| *Lampropeltis* | Black Milk Snake | *Lampropeltis* | Sinaloan Milk Snake |
| *Lampropeltis* | Black Milk Snake | *Morelia* | Coastal Carpet Python |
| *Lampropeltis* | Black Milk Snake | *Morelia* | Jaguar Carpet Python |
| *Lampropeltis* | Black Milk Snake | *Morelia* | Darwin Carpet Python |
| *Lampropeltis* | Black Milk Snake | *Morelia* | Irian Jaya Carpet Python |
| *Lampropeltis* | Black Milk Snake | *Morelia* | Carpet Python |
| *Lampropeltis* | Black Milk Snake | *Orthriophis* | Mussurana (Clelia clelia) |
| *Lampropeltis* | Black Milk Snake | *Orthriophis* | Yunnan Beauty Snake |
| *Lampropeltis* | Black Milk Snake | *Pantherophis* | Corn Snake |
| *Lampropeltis* | Black Milk Snake | *Philodryas* | Baron's Racer |
| *Lampropeltis* | Black Milk Snake | *Pituophis* | Sonoran Gopher Snake |
| *Lampropeltis* | Black Milk Snake | *Pituophis* | Cape Gopher Snake |
| *Lampropeltis* | Black Milk Snake | *Pituophis* | Bull Snake |
| *Lampropeltis* | Black Milk Snake | *Python* | Angolan Python |
| *Lampropeltis* | Black Milk Snake | *Python* | Jampea Reticulated Python |
| *Lampropeltis* | Black Milk Snake | *Python* | Reticulated Python |
| *Lampropeltis* | Black Milk Snake | *Python* | Blood Python |
| *Lampropeltis* | Black Milk Snake | *Python* | Ball Python |
| *Lampropeltis* | Black Milk Snake | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Lampropeltis* | Black Milk Snake | *Spilotes* | Tiger Rat Snake |
| *Lampropeltis* | Black Milk Snake | *Toxicodryas* | Blandings Tree Snake |
| *Lampropeltis* | Black Milk Snake | *Lampropeltis x Elaphe HYBRID* | California Cornsnake Hybrid |
| *Lampropeltis* | Black Milk Snake | *Aspidites x Python HYBRID* | Woma x Ball Python Hyrbid |
| *Lampropeltis* | Black Milk Snake | *Xenopeltis* | Sunbeam |
| *Morelia* | Coastal Carpet Python | *Aspidites* | Woma |
| *Morelia* | Coastal Carpet Python | *Boa* | Sonoran Boa Constrictor |
| *Morelia* | Coastal Carpet Python | *Boa* | Boa Constrictor |
| *Morelia* | Coastal Carpet Python | *Boa* | Tarahumara Boa Constrictor |
| *Morelia* | Coastal Carpet Python | *Boiga* | Dog Toothed Cat Snake |
| *Morelia* | Coastal Carpet Python | *Boiruna* | Mussurana (Boiruna maculata) |
| *Morelia* | Coastal Carpet Python | *Corallus* | Amazon Tree Boa |
| *Morelia* | Coastal Carpet Python | *Drymarchon* | Unicolor Cribo |
| *Morelia* | Coastal Carpet Python | *Drymarchon* | Black Tailed Cribo |
| *Morelia* | Coastal Carpet Python | *Drymarchon* | Yellow Tailed Cribo |
| *Morelia* | Coastal Carpet Python | *Elaphe* | King Rat Snake |
| *Morelia* | Coastal Carpet Python | *Elaphe* | Chinese Beauty Snake |
| *Morelia* | Coastal Carpet Python | *Gonionotophis* | Cape File Snake |
| *Morelia* | Coastal Carpet Python | *Gonionotophis* | West African File Snake |
| *Morelia* | Coastal Carpet Python | *Heloderma* | Beaded Lizard |
| *Morelia* | Coastal Carpet Python | *Hydrodynastes* | False Water Cobra |
| *Morelia* | Coastal Carpet Python | *Lampropeltis* | Honduran Milk Snake |
| *Morelia* | Coastal Carpet Python | *Lampropeltis* | Speckled Kingsnake |
| *Morelia* | Coastal Carpet Python | *Lampropeltis* | Atlantic Milk Snake |
| *Morelia* | Coastal Carpet Python | *Lampropeltis* | Desert Kingsnake |
| *Morelia* | Coastal Carpet Python | *Lampropeltis* | Eastern Kingsnake |
| *Morelia* | Coastal Carpet Python | *Lampropeltis* | California Kingsnake |
| *Morelia* | Coastal Carpet Python | *Lampropeltis* | Andean Milk Snake |
| *Morelia* | Coastal Carpet Python | *Lampropeltis* | Florida Kingsnake |
| *Morelia* | Coastal Carpet Python | *Lampropeltis* | Sinaloan Milk Snake |
| *Morelia* | Coastal Carpet Python | *Lampropeltis* | Black Milk Snake |
| *Morelia* | Coastal Carpet Python | *Morelia* | Jaguar Carpet Python |
| *Morelia* | Coastal Carpet Python | *Morelia* | Darwin Carpet Python |
| *Morelia* | Coastal Carpet Python | *Morelia* | Irian Jaya Carpet Python |
| *Morelia* | Coastal Carpet Python | *Morelia* | Carpet Python |
| *Morelia* | Coastal Carpet Python | *Orthriophis* | Mussurana (Clelia clelia) |
| *Morelia* | Coastal Carpet Python | *Orthriophis* | Yunnan Beauty Snake |
| *Morelia* | Coastal Carpet Python | *Pantherophis* | Corn Snake |

*Fig. 1 (cont.)*

| First Snake Species | | Second Snake Species | |
|---|---|---|---|
| Genus | Common Name | Genus | Common Name |
| *Morelia* | Coastal Carpet Python | *Philodryas* | Baron's Racer |
| *Morelia* | Coastal Carpet Python | *Pituophis* | Sonoran Gopher Snake |
| *Morelia* | Coastal Carpet Python | *Pituophis* | Cape Gopher Snake |
| *Morelia* | Coastal Carpet Python | *Pituophis* | Bull Snake |
| *Morelia* | Coastal Carpet Python | *Python* | Angolan Python |
| *Morelia* | Coastal Carpet Python | *Python* | Jampea Reticulated Python |
| *Morelia* | Coastal Carpet Python | *Python* | Reticulated Python |
| *Morelia* | Coastal Carpet Python | *Python* | Blood Python |
| *Morelia* | Coastal Carpet Python | *Python* | Ball Python |
| *Morelia* | Coastal Carpet Python | *Rhamphiophis* | Red Beaked Snakes |
| *Morelia* | Coastal Carpet Python | *Spilotes* | Tiger Rat Snake |
| *Morelia* | Coastal Carpet Python | *Toxicodryas* | Blandings Tree Snake |
| *Morelia* | Coastal Carpet Python | *Lampropeltis x Elaphe* HYBRID | California Cornsnake Hybrid |
| *Morelia* | Coastal Carpet Python | *Aspidites x Python* HYBRID | Woma x Ball Python Hyrbid |
| *Morelia* | Coastal Carpet Python | *Xenopeltis* | Sunbeam |
| *Morelia* | Jaguar Carpet Python | *Aspidites* | Woma |
| *Morelia* | Jaguar Carpet Python | *Boa* | Sonoran Boa Constrictor |
| *Morelia* | Jaguar Carpet Python | *Boa* | Boa Constrictor |
| *Morelia* | Jaguar Carpet Python | *Boa* | Tarahumara Boa Constrictor |
| *Morelia* | Jaguar Carpet Python | *Boiga* | Dog Toothed Cat Snake |
| *Morelia* | Jaguar Carpet Python | *Boiruna* | Mussurana (Boiruna maculata) |
| *Morelia* | Jaguar Carpet Python | *Corallus* | Amazon Tree Boa |
| *Morelia* | Jaguar Carpet Python | *Drymarchon* | Unicolor Cribo |
| *Morelia* | Jaguar Carpet Python | *Drymarchon* | Black Tailed Cribo |
| *Morelia* | Jaguar Carpet Python | *Drymarchon* | Yellow Tailed Cribo |
| *Morelia* | Jaguar Carpet Python | *Elaphe* | King Rat Snake |
| *Morelia* | Jaguar Carpet Python | *Elaphe* | Chinese Beauty Snake |
| *Morelia* | Jaguar Carpet Python | *Gonionotophis* | Cape File Snake |
| *Morelia* | Jaguar Carpet Python | *Gonionotophis* | West African File Snake |
| *Morelia* | Jaguar Carpet Python | *Heloderma* | Beaded Lizard |
| *Morelia* | Jaguar Carpet Python | *Hydrodynastes* | False Water Cobra |
| *Morelia* | Jaguar Carpet Python | *Lampropeltis* | Honduran Milk Snake |
| *Morelia* | Jaguar Carpet Python | *Lampropeltis* | Speckled Kingsnake |
| *Morelia* | Jaguar Carpet Python | *Lampropeltis* | Atlantic Milk Snake |
| *Morelia* | Jaguar Carpet Python | *Lampropeltis* | Desert Kingsnake |
| *Morelia* | Jaguar Carpet Python | *Lampropeltis* | Eastern Kingsnake |
| *Morelia* | Jaguar Carpet Python | *Lampropeltis* | California Kingsnake |
| *Morelia* | Jaguar Carpet Python | *Lampropeltis* | Andean Milk Snake |

*Fig. 1 (cont.)*

| First Snake Species | | Second Snake Species | |
|---|---|---|---|
| Genus | Common Name | Genus | Common Name |
| *Morelia* | Jaguar Carpet Python | *Lampropeltis* | Florida Kingsnake |
| *Morelia* | Jaguar Carpet Python | *Lampropeltis* | Sinaloan Milk Snake |
| *Morelia* | Jaguar Carpet Python | *Lampropeltis* | Black Milk Snake |
| *Morelia* | Jaguar Carpet Python | *Morelia* | Coastal Carpet Python |
| *Morelia* | Jaguar Carpet Python | *Morelia* | Darwin Carpet Python |
| *Morelia* | Jaguar Carpet Python | *Morelia* | Irian Jaya Carpet Python |
| *Morelia* | Jaguar Carpet Python | *Morelia* | Carpet Python |
| *Morelia* | Jaguar Carpet Python | *Orthriophis* | Mussurana (Clelia clelia) |
| *Morelia* | Jaguar Carpet Python | *Orthriophis* | Yunnan Beauty Snake |
| *Morelia* | Jaguar Carpet Python | *Pantherophis* | Corn Snake |
| *Morelia* | Jaguar Carpet Python | *Philodryas* | Baron's Racer |
| *Morelia* | Jaguar Carpet Python | *Pituophis* | Sonoran Gopher Snake |
| *Morelia* | Jaguar Carpet Python | *Pituophis* | Cape Gopher Snake |
| *Morelia* | Jaguar Carpet Python | *Pituophis* | Bull Snake |
| *Morelia* | Jaguar Carpet Python | *Python* | Angolan Python |
| *Morelia* | Jaguar Carpet Python | *Python* | Jampea Reticulated Python |
| *Morelia* | Jaguar Carpet Python | *Python* | Reticulated Python |
| *Morelia* | Jaguar Carpet Python | *Python* | Blood Python |
| *Morelia* | Jaguar Carpet Python | *Python* | Ball Python |
| *Morelia* | Jaguar Carpet Python | *Rhamphiophis* | Red Beaked Snakes |
| *Morelia* | Jaguar Carpet Python | *Spilotes* | Tiger Rat Snake |
| *Morelia* | Jaguar Carpet Python | *Toxicodryas* | Blandings Tree Snake |
| *Morelia* | Jaguar Carpet Python | *Lampropeltis x Elaphe* HYBRID | California Cornsnake Hybrid |
| *Morelia* | Jaguar Carpet Python | *Aspidites x Python* HYBRID | Woma x Ball Python Hyrbid |
| *Morelia* | Jaguar Carpet Python | *Xenopeltis* | Sunbeam |
| *Morelia* | Darwin Carpet Python | *Aspidites* | Woma |
| *Morelia* | Darwin Carpet Python | *Boa* | Sonoran Boa Constrictor |
| *Morelia* | Darwin Carpet Python | *Boa* | Boa Constrictor |
| *Morelia* | Darwin Carpet Python | *Boa* | Tarahumara Boa Constrictor |
| *Morelia* | Darwin Carpet Python | *Boiga* | Dog Toothed Cat Snake |
| *Morelia* | Darwin Carpet Python | *Boiruna* | Mussurana (Boiruna maculata) |
| *Morelia* | Darwin Carpet Python | *Corallus* | Amazon Tree Boa |
| *Morelia* | Darwin Carpet Python | *Drymarchon* | Unicolor Cribo |
| *Morelia* | Darwin Carpet Python | *Drymarchon* | Black Tailed Cribo |
| *Morelia* | Darwin Carpet Python | *Drymarchon* | Yellow Tailed Cribo |
| *Morelia* | Darwin Carpet Python | *Elaphe* | King Rat Snake |
| *Morelia* | Darwin Carpet Python | *Elaphe* | Chinese Beauty Snake |
| *Morelia* | Darwin Carpet Python | *Gonionotophis* | Cape File Snake |

*Fig. 1 (cont.)*

| FIRST SNAKE SPECIES | | SECOND SNAKE SPECIES | |
|---|---|---|---|
| Genus | Common Name | Genus | Common Name |
| *Morelia* | Darwin Carpet Python | *Gonionotophis* | West African File Snake |
| *Morelia* | Darwin Carpet Python | *Heloderma* | Beaded Lizard |
| *Morelia* | Darwin Carpet Python | *Hydrodynastes* | False Water Cobra |
| *Morelia* | Darwin Carpet Python | *Lampropeltis* | Honduran Milk Snake |
| *Morelia* | Darwin Carpet Python | *Lampropeltis* | Speckled Kingsnake |
| *Morelia* | Darwin Carpet Python | *Lampropeltis* | Atlantic Milk Snake |
| *Morelia* | Darwin Carpet Python | *Lampropeltis* | Desert Kingsnake |
| *Morelia* | Darwin Carpet Python | *Lampropeltis* | Eastern Kingsnake |
| *Morelia* | Darwin Carpet Python | *Lampropeltis* | California Kingsnake |
| *Morelia* | Darwin Carpet Python | *Lampropeltis* | Andean Milk Snake |
| *Morelia* | Darwin Carpet Python | *Lampropeltis* | Florida Kingsnake |
| *Morelia* | Darwin Carpet Python | *Lampropeltis* | Sinaloan Milk Snake |
| *Morelia* | Darwin Carpet Python | *Lampropeltis* | Black Milk Snake |
| *Morelia* | Darwin Carpet Python | *Morelia* | Coastal Carpet Python |
| *Morelia* | Darwin Carpet Python | *Morelia* | Jaguar Carpet Python |
| *Morelia* | Darwin Carpet Python | *Morelia* | Irian Jaya Carpet Python |
| *Morelia* | Darwin Carpet Python | *Morelia* | Carpet Python |
| *Morelia* | Darwin Carpet Python | *Orthriophis* | Mussurana (Clelia clelia) |
| *Morelia* | Darwin Carpet Python | *Orthriophis* | Yunnan Beauty Snake |
| *Morelia* | Darwin Carpet Python | *Pantherophis* | Corn Snake |
| *Morelia* | Darwin Carpet Python | *Philodryas* | Baron's Racer |
| *Morelia* | Darwin Carpet Python | *Pituophis* | Sonoran Gopher Snake |
| *Morelia* | Darwin Carpet Python | *Pituophis* | Cape Gopher Snake |
| *Morelia* | Darwin Carpet Python | *Pituophis* | Bull Snake |
| *Morelia* | Darwin Carpet Python | *Python* | Angolan Python |
| *Morelia* | Darwin Carpet Python | *Python* | Jampea Reticulated Python |
| *Morelia* | Darwin Carpet Python | *Python* | Reticulated Python |
| *Morelia* | Darwin Carpet Python | *Python* | Blood Python |
| *Morelia* | Darwin Carpet Python | *Python* | Ball Python |
| *Morelia* | Darwin Carpet Python | *Rhamphiophis* | Red Beaked Snakes |
| *Morelia* | Darwin Carpet Python | *Spilotes* | Tiger Rat Snake |
| *Morelia* | Darwin Carpet Python | *Toxicodryas* | Blandings Tree Snake |
| *Morelia* | Darwin Carpet Python | *Lampropeltis x Elaphe* HYBRID | California Cornsnake Hybrid |
| *Morelia* | Darwin Carpet Python | *Aspidites x Python* HYBRID | Woma x Ball Python Hyrbid |
| *Morelia* | Darwin Carpet Python | *Xenopeltis* | Sunbeam |
| *Morelia* | Irian Jaya Carpet Python | *Aspidites* | Woma |
| *Morelia* | Irian Jaya Carpet Python | *Boa* | Sonoran Boa Constrictor |
| *Morelia* | Irian Jaya Carpet Python | *Boa* | Boa Constrictor |

*Fig. 1 (cont.)*

| First Snake Species | | Second Snake Species | |
|---|---|---|---|
| Genus | Common Name | Genus | Common Name |
| *Morelia* | Irian Jaya Carpet Python | *Boa* | Tarahumara Boa Constrictor |
| *Morelia* | Irian Jaya Carpet Python | *Boiga* | Dog Toothed Cat Snake |
| *Morelia* | Irian Jaya Carpet Python | *Boiruna* | Mussurana (Boiruna maculata) |
| *Morelia* | Irian Jaya Carpet Python | *Corallus* | Amazon Tree Boa |
| *Morelia* | Irian Jaya Carpet Python | *Drymarchon* | Unicolor Cribo |
| *Morelia* | Irian Jaya Carpet Python | *Drymarchon* | Black Tailed Cribo |
| *Morelia* | Irian Jaya Carpet Python | *Drymarchon* | Yellow Tailed Cribo |
| *Morelia* | Irian Jaya Carpet Python | *Elaphe* | King Rat Snake |
| *Morelia* | Irian Jaya Carpet Python | *Elaphe* | Chinese Beauty Snake |
| *Morelia* | Irian Jaya Carpet Python | *Gonionotophis* | Cape File Snake |
| *Morelia* | Irian Jaya Carpet Python | *Gonionotophis* | West African File Snake |
| *Morelia* | Irian Jaya Carpet Python | *Heloderma* | Beaded Lizard |
| *Morelia* | Irian Jaya Carpet Python | *Hydrodynastes* | False Water Cobra |
| *Morelia* | Irian Jaya Carpet Python | *Lampropeltis* | Honduran Milk Snake |
| *Morelia* | Irian Jaya Carpet Python | *Lampropeltis* | Speckled Kingsnake |
| *Morelia* | Irian Jaya Carpet Python | *Lampropeltis* | Atlantic Milk Snake |
| *Morelia* | Irian Jaya Carpet Python | *Lampropeltis* | Desert Kingsnake |
| *Morelia* | Irian Jaya Carpet Python | *Lampropeltis* | Eastern Kingsnake |
| *Morelia* | Irian Jaya Carpet Python | *Lampropeltis* | California Kingsnake |
| *Morelia* | Irian Jaya Carpet Python | *Lampropeltis* | Andean Milk Snake |
| *Morelia* | Irian Jaya Carpet Python | *Lampropeltis* | Florida Kingsnake |
| *Morelia* | Irian Jaya Carpet Python | *Lampropeltis* | Sinaloan Milk Snake |
| *Morelia* | Irian Jaya Carpet Python | *Lampropeltis* | Black Milk Snake |
| *Morelia* | Irian Jaya Carpet Python | *Morelia* | Coastal Carpet Python |
| *Morelia* | Irian Jaya Carpet Python | *Morelia* | Jaguar Carpet Python |
| *Morelia* | Irian Jaya Carpet Python | *Morelia* | Darwin Carpet Python |
| *Morelia* | Irian Jaya Carpet Python | *Morelia* | Carpet Python |
| *Morelia* | Irian Jaya Carpet Python | *Orthriophis* | Mussurana (Clelia clelia) |
| *Morelia* | Irian Jaya Carpet Python | *Orthriophis* | Yunnan Beauty Snake |
| *Morelia* | Irian Jaya Carpet Python | *Pantherophis* | Corn Snake |
| *Morelia* | Irian Jaya Carpet Python | *Philodryas* | Baron's Racer |
| *Morelia* | Irian Jaya Carpet Python | *Pituophis* | Sonoran Gopher Snake |
| *Morelia* | Irian Jaya Carpet Python | *Pituophis* | Cape Gopher Snake |
| *Morelia* | Irian Jaya Carpet Python | *Pituophis* | Bull Snake |
| *Morelia* | Irian Jaya Carpet Python | *Python* | Angolan Python |
| *Morelia* | Irian Jaya Carpet Python | *Python* | Jampea Reticulated Python |
| *Morelia* | Irian Jaya Carpet Python | *Python* | Reticulated Python |
| *Morelia* | Irian Jaya Carpet Python | *Python* | Blood Python |
| *Morelia* | Irian Jaya Carpet Python | *Python* | Ball Python |
| *Morelia* | Irian Jaya Carpet Python | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Morelia* | Irian Jaya Carpet Python | *Spilotes* | Tiger Rat Snake |
| *Morelia* | Irian Jaya Carpet Python | *Toxicodryas* | Blandings Tree Snake |
| *Morelia* | Irian Jaya Carpet Python | *Lampropeltis x Elaphe* HYBRID | California Cornsnake Hybrid |
| *Morelia* | Irian Jaya Carpet Python | *Aspidites x Python* HYBRID | Woma x Ball Python Hyrbid |
| *Morelia* | Irian Jaya Carpet Python | *Xenopeltis* | Sunbeam |
| *Morelia* | Carpet Python | *Aspidites* | Woma |
| *Morelia* | Carpet Python | *Boa* | Sonoran Boa Constrictor |
| *Morelia* | Carpet Python | *Boa* | Boa Constrictor |
| *Morelia* | Carpet Python | *Boa* | Tarahumara Boa Constrictor |
| *Morelia* | Carpet Python | *Boiga* | Dog Toothed Cat Snake |
| *Morelia* | Carpet Python | *Boiruna* | Mussurana (Boiruna maculata) |
| *Morelia* | Carpet Python | *Corallus* | Amazon Tree Boa |
| *Morelia* | Carpet Python | *Drymarchon* | Unicolor Cribo |
| *Morelia* | Carpet Python | *Drymarchon* | Black Tailed Cribo |
| *Morelia* | Carpet Python | *Drymarchon* | Yellow Tailed Cribo |
| *Morelia* | Carpet Python | *Elaphe* | King Rat Snake |
| *Morelia* | Carpet Python | *Elaphe* | Chinese Beauty Snake |
| *Morelia* | Carpet Python | *Gonionotophis* | Cape File Snake |
| *Morelia* | Carpet Python | *Gonionotophis* | West African File Snake |
| *Morelia* | Carpet Python | *Heloderma* | Beaded Lizard |
| *Morelia* | Carpet Python | *Hydrodynastes* | False Water Cobra |
| *Morelia* | Carpet Python | *Lampropeltis* | Honduran Milk Snake |
| *Morelia* | Carpet Python | *Lampropeltis* | Speckled Kingsnake |
| *Morelia* | Carpet Python | *Lampropeltis* | Atlantic Milk Snake |
| *Morelia* | Carpet Python | *Lampropeltis* | Desert Kingsnake |
| *Morelia* | Carpet Python | *Lampropeltis* | Eastern Kingsnake |
| *Morelia* | Carpet Python | *Lampropeltis* | California Kingsnake |
| *Morelia* | Carpet Python | *Lampropeltis* | Andean Milk Snake |
| *Morelia* | Carpet Python | *Lampropeltis* | Florida Kingsnake |
| *Morelia* | Carpet Python | *Lampropeltis* | Sinaloan Milk Snake |
| *Morelia* | Carpet Python | *Lampropeltis* | Black Milk Snake |
| *Morelia* | Carpet Python | *Morelia* | Coastal Carpet Python |
| *Morelia* | Carpet Python | *Morelia* | Jaguar Carpet Python |
| *Morelia* | Carpet Python | *Morelia* | Darwin Carpet Python |
| *Morelia* | Carpet Python | *Morelia* | Irian Jaya Carpet Python |
| *Morelia* | Carpet Python | *Orthriophis* | Mussurana (Clelia clelia) |
| *Morelia* | Carpet Python | *Orthriophis* | Yunnan Beauty Snake |
| *Morelia* | Carpet Python | *Pantherophis* | Corn Snake |

*Fig. 1 (cont.)*

| First Snake Species | | Second Snake Species | |
|---|---|---|---|
| Genus | Common Name | Genus | Common Name |
| *Morelia* | Carpet Python | *Philodryas* | Baron's Racer |
| *Morelia* | Carpet Python | *Pituophis* | Sonoran Gopher Snake |
| *Morelia* | Carpet Python | *Pituophis* | Cape Gopher Snake |
| *Morelia* | Carpet Python | *Pituophis* | Bull Snake |
| *Morelia* | Carpet Python | *Python* | Angolan Python |
| *Morelia* | Carpet Python | *Python* | Jampea Reticulated Python |
| *Morelia* | Carpet Python | *Python* | Reticulated Python |
| *Morelia* | Carpet Python | *Python* | Blood Python |
| *Morelia* | Carpet Python | *Python* | Ball Python |
| *Morelia* | Carpet Python | *Rhamphiophis* | Red Beaked Snakes |
| *Morelia* | Carpet Python | *Spilotes* | Tiger Rat Snake |
| *Morelia* | Carpet Python | *Toxicodryas* | Blandings Tree Snake |
| *Morelia* | Carpet Python | *Lampropeltis x Elaphe HYBRID* | California Cornsnake Hybrid |
| *Morelia* | Carpet Python | *Aspidites x Python HYBRID* | Woma x Ball Python Hyrbid |
| *Morelia* | Carpet Python | *Xenopeltis* | Sunbeam |
| *Orthriophis* | Mussurana (Clelia clelia) | *Aspidites* | Woma |
| *Orthriophis* | Mussurana (Clelia clelia) | *Boa* | Sonoran Boa Constrictor |
| *Orthriophis* | Mussurana (Clelia clelia) | *Boa* | Boa Constrictor |
| *Orthriophis* | Mussurana (Clelia clelia) | *Boa* | Tarahumara Boa Constrictor |
| *Orthriophis* | Mussurana (Clelia clelia) | *Boiga* | Dog Toothed Cat Snake |
| *Orthriophis* | Mussurana (Clelia clelia) | *Boiruna* | Mussurana (Boiruna maculata) |
| *Orthriophis* | Mussurana (Clelia clelia) | *Corallus* | Amazon Tree Boa |
| *Orthriophis* | Mussurana (Clelia clelia) | *Drymarchon* | Unicolor Cribo |
| *Orthriophis* | Mussurana (Clelia clelia) | *Drymarchon* | Black Tailed Cribo |
| *Orthriophis* | Mussurana (Clelia clelia) | *Drymarchon* | Yellow Tailed Cribo |
| *Orthriophis* | Mussurana (Clelia clelia) | *Elaphe* | King Rat Snake |
| *Orthriophis* | Mussurana (Clelia clelia) | *Elaphe* | Chinese Beauty Snake |
| *Orthriophis* | Mussurana (Clelia clelia) | *Gonionotophis* | Cape File Snake |
| *Orthriophis* | Mussurana (Clelia clelia) | *Gonionotophis* | West African File Snake |
| *Orthriophis* | Mussurana (Clelia clelia) | *Heloderma* | Beaded Lizard |
| *Orthriophis* | Mussurana (Clelia clelia) | *Hydrodynastes* | False Water Cobra |
| *Orthriophis* | Mussurana (Clelia clelia) | *Lampropeltis* | Honduran Milk Snake |
| *Orthriophis* | Mussurana (Clelia clelia) | *Lampropeltis* | Speckled Kingsnake |
| *Orthriophis* | Mussurana (Clelia clelia) | *Lampropeltis* | Atlantic Milk Snake |
| *Orthriophis* | Mussurana (Clelia clelia) | *Lampropeltis* | Desert Kingsnake |
| *Orthriophis* | Mussurana (Clelia clelia) | *Lampropeltis* | Eastern Kingsnake |
| *Orthriophis* | Mussurana (Clelia clelia) | *Lampropeltis* | California Kingsnake |
| *Orthriophis* | Mussurana (Clelia clelia) | *Lampropeltis* | Andean Milk Snake |

*Fig. 1 (cont.)*

| First Snake Species | | Second Snake Species | |
|---|---|---|---|
| Genus | Common Name | Genus | Common Name |
| Orthriophis | Mussurana (Clelia clelia) | Lampropeltis | Florida Kingsnake |
| Orthriophis | Mussurana (Clelia clelia) | Lampropeltis | Sinaloan Milk Snake |
| Orthriophis | Mussurana (Clelia clelia) | Lampropeltis | Black Milk Snake |
| Orthriophis | Mussurana (Clelia clelia) | Morelia | Coastal Carpet Python |
| Orthriophis | Mussurana (Clelia clelia) | Morelia | Jaguar Carpet Python |
| Orthriophis | Mussurana (Clelia clelia) | Morelia | Darwin Carpet Python |
| Orthriophis | Mussurana (Clelia clelia) | Morelia | Irian Jaya Carpet Python |
| Orthriophis | Mussurana (Clelia clelia) | Morelia | Carpet Python |
| Orthriophis | Mussurana (Clelia clelia) | Orthriophis | Yunnan Beauty Snake |
| Orthriophis | Mussurana (Clelia clelia) | Pantherophis | Corn Snake |
| Orthriophis | Mussurana (Clelia clelia) | Philodryas | Baron's Racer |
| Orthriophis | Mussurana (Clelia clelia) | Pituophis | Sonoran Gopher Snake |
| Orthriophis | Mussurana (Clelia clelia) | Pituophis | Cape Gopher Snake |
| Orthriophis | Mussurana (Clelia clelia) | Pituophis | Bull Snake |
| Orthriophis | Mussurana (Clelia clelia) | Python | Angolan Python |
| Orthriophis | Mussurana (Clelia clelia) | Python | Jampea Reticulated Python |
| Orthriophis | Mussurana (Clelia clelia) | Python | Reticulated Python |
| Orthriophis | Mussurana (Clelia clelia) | Python | Blood Python |
| Orthriophis | Mussurana (Clelia clelia) | Python | Ball Python |
| Orthriophis | Mussurana (Clelia clelia) | Rhamphiophis | Red Beaked Snakes |
| Orthriophis | Mussurana (Clelia clelia) | Spilotes | Tiger Rat Snake |
| Orthriophis | Mussurana (Clelia clelia) | Toxicodryas | Blandings Tree Snake |
| Orthriophis | Mussurana (Clelia clelia) | Lampropeltis x Elaphe HYBRID | California Cornsnake Hybrid |
| Orthriophis | Mussurana (Clelia clelia) | Aspidites x Python HYBRID | Woma x Ball Python Hyrbid |
| Orthriophis | Mussurana (Clelia clelia) | Xenopeltis | Sunbeam |
| Orthriophis | Yunnan Beauty Snake | Aspidites | Woma |
| Orthriophis | Yunnan Beauty Snake | Boa | Sonoran Boa Constrictor |
| Orthriophis | Yunnan Beauty Snake | Boa | Boa Constrictor |
| Orthriophis | Yunnan Beauty Snake | Boa | Tarahumara Boa Constrictor |
| Orthriophis | Yunnan Beauty Snake | Boiga | Dog Toothed Cat Snake |
| Orthriophis | Yunnan Beauty Snake | Boiruna | Mussurana (Boiruna maculata) |
| Orthriophis | Yunnan Beauty Snake | Corallus | Amazon Tree Boa |
| Orthriophis | Yunnan Beauty Snake | Drymarchon | Unicolor Cribo |
| Orthriophis | Yunnan Beauty Snake | Drymarchon | Black Tailed Cribo |
| Orthriophis | Yunnan Beauty Snake | Drymarchon | Yellow Tailed Cribo |
| Orthriophis | Yunnan Beauty Snake | Elaphe | King Rat Snake |
| Orthriophis | Yunnan Beauty Snake | Elaphe | Chinese Beauty Snake |
| Orthriophis | Yunnan Beauty Snake | Gonionotophis | Cape File Snake |

*Fig. 1 (cont.)*

| First Snake Species | | Second Snake Species | |
|---|---|---|---|
| Genus | Common Name | Genus | Common Name |
| *Orthriophis* | Yunnan Beauty Snake | *Gonionotophis* | West African File Snake |
| *Orthriophis* | Yunnan Beauty Snake | *Heloderma* | Beaded Lizard |
| *Orthriophis* | Yunnan Beauty Snake | *Hydrodynastes* | False Water Cobra |
| *Orthriophis* | Yunnan Beauty Snake | *Lampropeltis* | Honduran Milk Snake |
| *Orthriophis* | Yunnan Beauty Snake | *Lampropeltis* | Speckled Kingsnake |
| *Orthriophis* | Yunnan Beauty Snake | *Lampropeltis* | Atlantic Milk Snake |
| *Orthriophis* | Yunnan Beauty Snake | *Lampropeltis* | Desert Kingsnake |
| *Orthriophis* | Yunnan Beauty Snake | *Lampropeltis* | Eastern Kingsnake |
| *Orthriophis* | Yunnan Beauty Snake | *Lampropeltis* | California Kingsnake |
| *Orthriophis* | Yunnan Beauty Snake | *Lampropeltis* | Andean Milk Snake |
| *Orthriophis* | Yunnan Beauty Snake | *Lampropeltis* | Florida Kingsnake |
| *Orthriophis* | Yunnan Beauty Snake | *Lampropeltis* | Sinaloan Milk Snake |
| *Orthriophis* | Yunnan Beauty Snake | *Lampropeltis* | Black Milk Snake |
| *Orthriophis* | Yunnan Beauty Snake | *Morelia* | Coastal Carpet Python |
| *Orthriophis* | Yunnan Beauty Snake | *Morelia* | Jaguar Carpet Python |
| *Orthriophis* | Yunnan Beauty Snake | *Morelia* | Darwin Carpet Python |
| *Orthriophis* | Yunnan Beauty Snake | *Morelia* | Irian Jaya Carpet Python |
| *Orthriophis* | Yunnan Beauty Snake | *Morelia* | Carpet Python |
| *Orthriophis* | Yunnan Beauty Snake | *Orthriophis* | Mussurana (Clelia clelia) |
| *Orthriophis* | Yunnan Beauty Snake | *Pantherophis* | Corn Snake |
| *Orthriophis* | Yunnan Beauty Snake | *Philodryas* | Baron's Racer |
| *Orthriophis* | Yunnan Beauty Snake | *Pituophis* | Sonoran Gopher Snake |
| *Orthriophis* | Yunnan Beauty Snake | *Pituophis* | Cape Gopher Snake |
| *Orthriophis* | Yunnan Beauty Snake | *Pituophis* | Bull Snake |
| *Orthriophis* | Yunnan Beauty Snake | *Python* | Angolan Python |
| *Orthriophis* | Yunnan Beauty Snake | *Python* | Jampea Reticulated Python |
| *Orthriophis* | Yunnan Beauty Snake | *Python* | Reticulated Python |
| *Orthriophis* | Yunnan Beauty Snake | *Python* | Blood Python |
| *Orthriophis* | Yunnan Beauty Snake | *Python* | Ball Python |
| *Orthriophis* | Yunnan Beauty Snake | *Rhamphiophis* | Red Beaked Snakes |
| *Orthriophis* | Yunnan Beauty Snake | *Spilotes* | Tiger Rat Snake |
| *Orthriophis* | Yunnan Beauty Snake | *Toxicodryas* | Blandings Tree Snake |
| *Orthriophis* | Yunnan Beauty Snake | *Lampropeltis x Elaphe* HYBRID | California Cornsnake Hybrid |
| *Orthriophis* | Yunnan Beauty Snake | *Aspidites x Python* HYBRID | Woma x Ball Python Hyrbid |
| *Orthriophis* | Yunnan Beauty Snake | *Xenopeltis* | Sunbeam |
| *Pantherophis* | Corn Snake | *Aspidites* | Woma |
| *Pantherophis* | Corn Snake | *Boa* | Sonoran Boa Constrictor |
| *Pantherophis* | Corn Snake | *Boa* | Boa Constrictor |

*Fig. 1 (cont.)*

| First Snake Species | | Second Snake Species | |
|---|---|---|---|
| Genus | Common Name | Genus | Common Name |
| *Pantherophis* | Corn Snake | *Boa* | Tarahumara Boa Constrictor |
| *Pantherophis* | Corn Snake | *Boiga* | Dog Toothed Cat Snake |
| *Pantherophis* | Corn Snake | *Boiruna* | Mussurana (Boiruna maculata) |
| *Pantherophis* | Corn Snake | *Corallus* | Amazon Tree Boa |
| *Pantherophis* | Corn Snake | *Drymarchon* | Unicolor Cribo |
| *Pantherophis* | Corn Snake | *Drymarchon* | Black Tailed Cribo |
| *Pantherophis* | Corn Snake | *Drymarchon* | Yellow Tailed Cribo |
| *Pantherophis* | Corn Snake | *Elaphe* | King Rat Snake |
| *Pantherophis* | Corn Snake | *Elaphe* | Chinese Beauty Snake |
| *Pantherophis* | Corn Snake | *Gonionotophis* | Cape File Snake |
| *Pantherophis* | Corn Snake | *Gonionotophis* | West African File Snake |
| *Pantherophis* | Corn Snake | *Heloderma* | Beaded Lizard |
| *Pantherophis* | Corn Snake | *Hydrodynastes* | False Water Cobra |
| *Pantherophis* | Corn Snake | *Lampropeltis* | Honduran Milk Snake |
| *Pantherophis* | Corn Snake | *Lampropeltis* | Speckled Kingsnake |
| *Pantherophis* | Corn Snake | *Lampropeltis* | Atlantic Milk Snake |
| *Pantherophis* | Corn Snake | *Lampropeltis* | Desert Kingsnake |
| *Pantherophis* | Corn Snake | *Lampropeltis* | Eastern Kingsnake |
| *Pantherophis* | Corn Snake | *Lampropeltis* | California Kingsnake |
| *Pantherophis* | Corn Snake | *Lampropeltis* | Andean Milk Snake |
| *Pantherophis* | Corn Snake | *Lampropeltis* | Florida Kingsnake |
| *Pantherophis* | Corn Snake | *Lampropeltis* | Sinaloan Milk Snake |
| *Pantherophis* | Corn Snake | *Lampropeltis* | Black Milk Snake |
| *Pantherophis* | Corn Snake | *Morelia* | Coastal Carpet Python |
| *Pantherophis* | Corn Snake | *Morelia* | Jaguar Carpet Python |
| *Pantherophis* | Corn Snake | *Morelia* | Darwin Carpet Python |
| *Pantherophis* | Corn Snake | *Morelia* | Irian Jaya Carpet Python |
| *Pantherophis* | Corn Snake | *Morelia* | Carpet Python |
| *Pantherophis* | Corn Snake | *Orthriophis* | Mussurana (Cielia clelia) |
| *Pantherophis* | Corn Snake | *Orthriophis* | Yunnan Beauty Snake |
| *Pantherophis* | Corn Snake | *Philodryas* | Baron's Racer |
| *Pantherophis* | Corn Snake | *Pituophis* | Sonoran Gopher Snake |
| *Pantherophis* | Corn Snake | *Pituophis* | Cape Gopher Snake |
| *Pantherophis* | Corn Snake | *Pituophis* | Bull Snake |
| *Pantherophis* | Corn Snake | *Python* | Angolan Python |
| *Pantherophis* | Corn Snake | *Python* | Jampea Reticulated Python |
| *Pantherophis* | Corn Snake | *Python* | Reticulated Python |
| *Pantherophis* | Corn Snake | *Python* | Blood Python |
| *Pantherophis* | Corn Snake | *Python* | Ball Python |
| *Pantherophis* | Corn Snake | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Pantherophis* | Corn Snake | *Spilotes* | Tiger Rat Snake |
| *Pantherophis* | Corn Snake | *Toxicodryas* | Blandings Tree Snake |
| *Pantherophis* | Corn Snake | *Lampropeltis x Elaphe* HYBRID | California Cornsnake Hybrid |
| *Pantherophis* | Corn Snake | *Aspidites x Python* HYBRID | Woma x Ball Python Hyrbid |
| *Pantherophis* | Corn Snake | *Xenopeltis* | Sunbeam |
| *Philodryas* | Baron's Racer | *Aspidites* | Woma |
| *Philodryas* | Baron's Racer | *Boa* | Sonoran Boa Constrictor |
| *Philodryas* | Baron's Racer | *Boa* | Boa Constrictor |
| *Philodryas* | Baron's Racer | *Boa* | Tarahumara Boa Constrictor |
| *Philodryas* | Baron's Racer | *Boiga* | Dog Toothed Cat Snake |
| *Philodryas* | Baron's Racer | *Boiruna* | Mussurana (Boiruna maculata) |
| *Philodryas* | Baron's Racer | *Corallus* | Amazon Tree Boa |
| *Philodryas* | Baron's Racer | *Drymarchon* | Unicolor Cribo |
| *Philodryas* | Baron's Racer | *Drymarchon* | Black Tailed Cribo |
| *Philodryas* | Baron's Racer | *Drymarchon* | Yellow Tailed Cribo |
| *Philodryas* | Baron's Racer | *Elaphe* | King Rat Snake |
| *Philodryas* | Baron's Racer | *Elaphe* | Chinese Beauty Snake |
| *Philodryas* | Baron's Racer | *Gonionotophis* | Cape File Snake |
| *Philodryas* | Baron's Racer | *Gonionotophis* | West African File Snake |
| *Philodryas* | Baron's Racer | *Heloderma* | Beaded Lizard |
| *Philodryas* | Baron's Racer | *Hydrodynastes* | False Water Cobra |
| *Philodryas* | Baron's Racer | *Lampropeltis* | Honduran Milk Snake |
| *Philodryas* | Baron's Racer | *Lampropeltis* | Speckled Kingsnake |
| *Philodryas* | Baron's Racer | *Lampropeltis* | Atlantic Milk Snake |
| *Philodryas* | Baron's Racer | *Lampropeltis* | Desert Kingsnake |
| *Philodryas* | Baron's Racer | *Lampropeltis* | Eastern Kingsnake |
| *Philodryas* | Baron's Racer | *Lampropeltis* | California Kingsnake |
| *Philodryas* | Baron's Racer | *Lampropeltis* | Andean Milk Snake |
| *Philodryas* | Baron's Racer | *Lampropeltis* | Florida Kingsnake |
| *Philodryas* | Baron's Racer | *Lampropeltis* | Sinaloan Milk Snake |
| *Philodryas* | Baron's Racer | *Lampropeltis* | Black Milk Snake |
| *Philodryas* | Baron's Racer | *Morelia* | Coastal Carpet Python |
| *Philodryas* | Baron's Racer | *Morelia* | Jaguar Carpet Python |
| *Philodryas* | Baron's Racer | *Morelia* | Darwin Carpet Python |
| *Philodryas* | Baron's Racer | *Morelia* | Irian Jaya Carpet Python |
| *Philodryas* | Baron's Racer | *Morelia* | Carpet Python |
| *Philodryas* | Baron's Racer | *Orthriophis* | Mussurana (Clelia clelia) |
| *Philodryas* | Baron's Racer | *Orthriophis* | Yunnan Beauty Snake |

Fig. 1 (cont.)

| First Snake Species | | Second Snake Species | |
|---|---|---|---|
| Genus | Common Name | Genus | Common Name |
| *Philodryas* | Baron's Racer | *Pantherophis* | Corn Snake |
| *Philodryas* | Baron's Racer | *Pituophis* | Sonoran Gopher Snake |
| *Philodryas* | Baron's Racer | *Pituophis* | Cape Gopher Snake |
| *Philodryas* | Baron's Racer | *Pituophis* | Bull Snake |
| *Philodryas* | Baron's Racer | *Python* | Angolan Python |
| *Philodryas* | Baron's Racer | *Python* | Jampea Reticulated Python |
| *Philodryas* | Baron's Racer | *Python* | Reticulated Python |
| *Philodryas* | Baron's Racer | *Python* | Blood Python |
| *Philodryas* | Baron's Racer | *Python* | Ball Python |
| *Philodryas* | Baron's Racer | *Rhamphiophis* | Red Beaked Snakes |
| *Philodryas* | Baron's Racer | *Spilotes* | Tiger Rat Snake |
| *Philodryas* | Baron's Racer | *Toxicodryas* | Blandings Tree Snake |
| *Philodryas* | Baron's Racer | *Lampropeltis x Elaphe* HYBRID | California Cornsnake Hybrid |
| *Philodryas* | Baron's Racer | *Aspidites x Python* HYBRID | Woma x Ball Python Hyrbid |
| *Philodryas* | Baron's Racer | *Xenopeltis* | Sunbeam |
| *Pituophis* | Sonoran Gopher Snake | *Aspidites* | Woma |
| *Pituophis* | Sonoran Gopher Snake | *Boa* | Sonoran Boa Constrictor |
| *Pituophis* | Sonoran Gopher Snake | *Boa* | Boa Constrictor |
| *Pituophis* | Sonoran Gopher Snake | *Boa* | Tarahumara Boa Constrictor |
| *Pituophis* | Sonoran Gopher Snake | *Boiga* | Dog Toothed Cat Snake |
| *Pituophis* | Sonoran Gopher Snake | *Boiruna* | Mussurana (Boiruna maculata) |
| *Pituophis* | Sonoran Gopher Snake | *Corallus* | Amazon Tree Boa |
| *Pituophis* | Sonoran Gopher Snake | *Drymarchon* | Unicolor Cribo |
| *Pituophis* | Sonoran Gopher Snake | *Drymarchon* | Black Tailed Cribo |
| *Pituophis* | Sonoran Gopher Snake | *Drymarchon* | Yellow Tailed Cribo |
| *Pituophis* | Sonoran Gopher Snake | *Elaphe* | King Rat Snake |
| *Pituophis* | Sonoran Gopher Snake | *Elaphe* | Chinese Beauty Snake |
| *Pituophis* | Sonoran Gopher Snake | *Gonionotophis* | Cape File Snake |
| *Pituophis* | Sonoran Gopher Snake | *Gonionotophis* | West African File Snake |
| *Pituophis* | Sonoran Gopher Snake | *Heloderma* | Beaded Lizard |
| *Pituophis* | Sonoran Gopher Snake | *Hydrodynastes* | False Water Cobra |
| *Pituophis* | Sonoran Gopher Snake | *Lampropeltis* | Honduran Milk Snake |
| *Pituophis* | Sonoran Gopher Snake | *Lampropeltis* | Speckled Kingsnake |
| *Pituophis* | Sonoran Gopher Snake | *Lampropeltis* | Atlantic Milk Snake |
| *Pituophis* | Sonoran Gopher Snake | *Lampropeltis* | Desert Kingsnake |
| *Pituophis* | Sonoran Gopher Snake | *Lampropeltis* | Eastern Kingsnake |
| *Pituophis* | Sonoran Gopher Snake | *Lampropeltis* | California Kingsnake |
| *Pituophis* | Sonoran Gopher Snake | *Lampropeltis* | Andean Milk Snake |

*Fig. 1 (cont.)*

| First Snake Species | | Second Snake Species | |
|---|---|---|---|
| Genus | Common Name | Genus | Common Name |
| *Pituophis* | Sonoran Gopher Snake | *Lampropeltis* | Florida Kingsnake |
| *Pituophis* | Sonoran Gopher Snake | *Lampropeltis* | Sinaloan Milk Snake |
| *Pituophis* | Sonoran Gopher Snake | *Lampropeltis* | Black Milk Snake |
| *Pituophis* | Sonoran Gopher Snake | *Morelia* | Coastal Carpet Python |
| *Pituophis* | Sonoran Gopher Snake | *Morelia* | Jaguar Carpet Python |
| *Pituophis* | Sonoran Gopher Snake | *Morelia* | Darwin Carpet Python |
| *Pituophis* | Sonoran Gopher Snake | *Morelia* | Irian Jaya Carpet Python |
| *Pituophis* | Sonoran Gopher Snake | *Morelia* | Carpet Python |
| *Pituophis* | Sonoran Gopher Snake | *Orthriophis* | Mussurana (Clelia clelia) |
| *Pituophis* | Sonoran Gopher Snake | *Orthriophis* | Yunnan Beauty Snake |
| *Pituophis* | Sonoran Gopher Snake | *Pantherophis* | Corn Snake |
| *Pituophis* | Sonoran Gopher Snake | *Philodryas* | Baron's Racer |
| *Pituophis* | Sonoran Gopher Snake | *Pituophis* | Cape Gopher Snake |
| *Pituophis* | Sonoran Gopher Snake | *Pituophis* | Bull Snake |
| *Pituophis* | Sonoran Gopher Snake | *Python* | Angolan Python |
| *Pituophis* | Sonoran Gopher Snake | *Python* | Jampea Reticulated Python |
| *Pituophis* | Sonoran Gopher Snake | *Python* | Reticulated Python |
| *Pituophis* | Sonoran Gopher Snake | *Python* | Blood Python |
| *Pituophis* | Sonoran Gopher Snake | *Python* | Ball Python |
| *Pituophis* | Sonoran Gopher Snake | *Rhamphiophis* | Red Beaked Snakes |
| *Pituophis* | Sonoran Gopher Snake | *Spilotes* | Tiger Rat Snake |
| *Pituophis* | Sonoran Gopher Snake | *Toxicodryas* | Blandings Tree Snake |
| *Pituophis* | Sonoran Gopher Snake | *Lampropeltis x Elaphe* HYBRID | California Cornsnake Hybrid |
| *Pituophis* | Sonoran Gopher Snake | *Aspidites x Python* HYBRID | Woma x Ball Python Hyrbid |
| *Pituophis* | Sonoran Gopher Snake | *Xenopeltis* | Sunbeam |
| *Pituophis* | Cape Gopher Snake | *Aspidites* | Woma |
| *Pituophis* | Cape Gopher Snake | *Boa* | Sonoran Boa Constrictor |
| *Pituophis* | Cape Gopher Snake | *Boa* | Boa Constrictor |
| *Pituophis* | Cape Gopher Snake | *Boa* | Tarahumara Boa Constrictor |
| *Pituophis* | Cape Gopher Snake | *Boiga* | Dog Toothed Cat Snake |
| *Pituophis* | Cape Gopher Snake | *Boiruna* | Mussurana (Boiruna maculata) |
| *Pituophis* | Cape Gopher Snake | *Corallus* | Amazon Tree Boa |
| *Pituophis* | Cape Gopher Snake | *Drymarchon* | Unicolor Cribo |
| *Pituophis* | Cape Gopher Snake | *Drymarchon* | Black Tailed Cribo |
| *Pituophis* | Cape Gopher Snake | *Drymarchon* | Yellow Tailed Cribo |
| *Pituophis* | Cape Gopher Snake | *Elaphe* | King Rat Snake |
| *Pituophis* | Cape Gopher Snake | *Elaphe* | Chinese Beauty Snake |
| *Pituophis* | Cape Gopher Snake | *Gonionotophis* | Cape File Snake |

*Fig. 1 (cont.)*

| First Snake Species | | Second Snake Species | |
|---|---|---|---|
| Genus | Common Name | Genus | Common Name |
| *Pituophis* | Cape Gopher Snake | *Gonionotophis* | West African File Snake |
| *Pituophis* | Cape Gopher Snake | *Heloderma* | Beaded Lizard |
| *Pituophis* | Cape Gopher Snake | *Hydrodynastes* | False Water Cobra |
| *Pituophis* | Cape Gopher Snake | *Lampropeltis* | Honduran Milk Snake |
| *Pituophis* | Cape Gopher Snake | *Lampropeltis* | Speckled Kingsnake |
| *Pituophis* | Cape Gopher Snake | *Lampropeltis* | Atlantic Milk Snake |
| *Pituophis* | Cape Gopher Snake | *Lampropeltis* | Desert Kingsnake |
| *Pituophis* | Cape Gopher Snake | *Lampropeltis* | Eastern Kingsnake |
| *Pituophis* | Cape Gopher Snake | *Lampropeltis* | California Kingsnake |
| *Pituophis* | Cape Gopher Snake | *Lampropeltis* | Andean Milk Snake |
| *Pituophis* | Cape Gopher Snake | *Lampropeltis* | Florida Kingsnake |
| *Pituophis* | Cape Gopher Snake | *Lampropeltis* | Sinaloan Milk Snake |
| *Pituophis* | Cape Gopher Snake | *Lampropeltis* | Black Milk Snake |
| *Pituophis* | Cape Gopher Snake | *Morelia* | Coastal Carpet Python |
| *Pituophis* | Cape Gopher Snake | *Morelia* | Jaguar Carpet Python |
| *Pituophis* | Cape Gopher Snake | *Morelia* | Darwin Carpet Python |
| *Pituophis* | Cape Gopher Snake | *Morelia* | Irian Jaya Carpet Python |
| *Pituophis* | Cape Gopher Snake | *Morelia* | Carpet Python |
| *Pituophis* | Cape Gopher Snake | *Orthriophis* | Mussurana (Clelia clelia) |
| *Pituophis* | Cape Gopher Snake | *Orthriophis* | Yunnan Beauty Snake |
| *Pituophis* | Cape Gopher Snake | *Pantherophis* | Corn Snake |
| *Pituophis* | Cape Gopher Snake | *Philodryas* | Baron's Racer |
| *Pituophis* | Cape Gopher Snake | *Pituophis* | Sonoran Gopher Snake |
| *Pituophis* | Cape Gopher Snake | *Pituophis* | Bull Snake |
| *Pituophis* | Cape Gopher Snake | *Python* | Angolan Python |
| *Pituophis* | Cape Gopher Snake | *Python* | Jampea Reticulated Python |
| *Pituophis* | Cape Gopher Snake | *Python* | Reticulated Python |
| *Pituophis* | Cape Gopher Snake | *Python* | Blood Python |
| *Pituophis* | Cape Gopher Snake | *Python* | Ball Python |
| *Pituophis* | Cape Gopher Snake | *Rhamphiophis* | Red Beaked Snakes |
| *Pituophis* | Cape Gopher Snake | *Spilotes* | Tiger Rat Snake |
| *Pituophis* | Cape Gopher Snake | *Toxicodryas* | Blandings Tree Snake |
| *Pituophis* | Cape Gopher Snake | *Lampropeltis x Elaphe* HYBRID | California Cornsnake Hybrid |
| *Pituophis* | Cape Gopher Snake | *Aspidites x Python* HYBRID | Woma x Ball Python Hyrbid |
| *Pituophis* | Cape Gopher Snake | *Xenopeltis* | Sunbeam |
| *Pituophis* | Bull Snake | *Aspidites* | Woma |
| *Pituophis* | Bull Snake | *Boa* | Sonoran Boa Constrictor |
| *Pituophis* | Bull Snake | *Boa* | Boa Constrictor |

*Fig. 1 (cont.)*

| First Snake Species | | Second Snake Species | |
|---|---|---|---|
| Genus | Common Name | Genus | Common Name |
| *Pituophis* | Bull Snake | *Boa* | Tarahumara Boa Constrictor |
| *Pituophis* | Bull Snake | *Boiga* | Dog Toothed Cat Snake |
| *Pituophis* | Bull Snake | *Boiruna* | Mussurana (Boiruna maculata) |
| *Pituophis* | Bull Snake | *Corallus* | Amazon Tree Boa |
| *Pituophis* | Bull Snake | *Drymarchon* | Unicolor Cribo |
| *Pituophis* | Bull Snake | *Drymarchon* | Black Tailed Cribo |
| *Pituophis* | Bull Snake | *Drymarchon* | Yellow Tailed Cribo |
| *Pituophis* | Bull Snake | *Elaphe* | King Rat Snake |
| *Pituophis* | Bull Snake | *Elaphe* | Chinese Beauty Snake |
| *Pituophis* | Bull Snake | *Gonionotophis* | Cape File Snake |
| *Pituophis* | Bull Snake | *Gonionotophis* | West African File Snake |
| *Pituophis* | Bull Snake | *Heloderma* | Beaded Lizard |
| *Pituophis* | Bull Snake | *Hydrodynastes* | False Water Cobra |
| *Pituophis* | Bull Snake | *Lampropeltis* | Honduran Milk Snake |
| *Pituophis* | Bull Snake | *Lampropeltis* | Speckled Kingsnake |
| *Pituophis* | Bull Snake | *Lampropeltis* | Atlantic Milk Snake |
| *Pituophis* | Bull Snake | *Lampropeltis* | Desert Kingsnake |
| *Pituophis* | Bull Snake | *Lampropeltis* | Eastern Kingsnake |
| *Pituophis* | Bull Snake | *Lampropeltis* | California Kingsnake |
| *Pituophis* | Bull Snake | *Lampropeltis* | Andean Milk Snake |
| *Pituophis* | Bull Snake | *Lampropeltis* | Florida Kingsnake |
| *Pituophis* | Bull Snake | *Lampropeltis* | Sinaloan Milk Snake |
| *Pituophis* | Bull Snake | *Lampropeltis* | Black Milk Snake |
| *Pituophis* | Bull Snake | *Morelia* | Coastal Carpet Python |
| *Pituophis* | Bull Snake | *Morelia* | Jaguar Carpet Python |
| *Pituophis* | Bull Snake | *Morelia* | Darwin Carpet Python |
| *Pituophis* | Bull Snake | *Morelia* | Irian Jaya Carpet Python |
| *Pituophis* | Bull Snake | *Morelia* | Carpet Python |
| *Pituophis* | Bull Snake | *Orthriophis* | Mussurana (Cielia clelia) |
| *Pituophis* | Bull Snake | *Orthriophis* | Yunnan Beauty Snake |
| *Pituophis* | Bull Snake | *Pantherophis* | Corn Snake |
| *Pituophis* | Bull Snake | *Philodryas* | Baron's Racer |
| *Pituophis* | Bull Snake | *Pituophis* | Sonoran Gopher Snake |
| *Pituophis* | Bull Snake | *Pituophis* | Cape Gopher Snake |
| *Pituophis* | Bull Snake | *Python* | Angolan Python |
| *Pituophis* | Bull Snake | *Python* | Jampea Reticulated Python |
| *Pituophis* | Bull Snake | *Python* | Reticulated Python |
| *Pituophis* | Bull Snake | *Python* | Blood Python |
| *Pituophis* | Bull Snake | *Python* | Ball Python |
| *Pituophis* | Bull Snake | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Pituophis* | Bull Snake | *Spilotes* | Tiger Rat Snake |
| *Pituophis* | Bull Snake | *Toxicodryas* | Blandings Tree Snake |
| *Pituophis* | Bull Snake | *Lampropeltis x Elaphe* HYBRID | California Cornsnake Hybrid |
| *Pituophis* | Bull Snake | *Aspidites x Python* HYBRID | Woma x Ball Python Hyrbid |
| *Pituophis* | Bull Snake | *Xenopeltis* | Sunbeam |
| *Python* | Angolan Python | *Aspidites* | Woma |
| *Python* | Angolan Python | *Boa* | Sonoran Boa Constrictor |
| *Python* | Angolan Python | *Boa* | Boa Constrictor |
| *Python* | Angolan Python | *Boa* | Tarahumara Boa Constrictor |
| *Python* | Angolan Python | *Boiga* | Dog Toothed Cat Snake |
| *Python* | Angolan Python | *Boiruna* | Mussurana (Boiruna maculata) |
| *Python* | Angolan Python | *Corallus* | Amazon Tree Boa |
| *Python* | Angolan Python | *Drymarchon* | Unicolor Cribo |
| *Python* | Angolan Python | *Drymarchon* | Black Tailed Cribo |
| *Python* | Angolan Python | *Drymarchon* | Yellow Tailed Cribo |
| *Python* | Angolan Python | *Elaphe* | King Rat Snake |
| *Python* | Angolan Python | *Elaphe* | Chinese Beauty Snake |
| *Python* | Angolan Python | *Gonionotophis* | Cape File Snake |
| *Python* | Angolan Python | *Gonionotophis* | West African File Snake |
| *Python* | Angolan Python | *Heloderma* | Beaded Lizard |
| *Python* | Angolan Python | *Hydrodynastes* | False Water Cobra |
| *Python* | Angolan Python | *Lampropeltis* | Honduran Milk Snake |
| *Python* | Angolan Python | *Lampropeltis* | Speckled Kingsnake |
| *Python* | Angolan Python | *Lampropeltis* | Atlantic Milk Snake |
| *Python* | Angolan Python | *Lampropeltis* | Desert Kingsnake |
| *Python* | Angolan Python | *Lampropeltis* | Eastern Kingsnake |
| *Python* | Angolan Python | *Lampropeltis* | California Kingsnake |
| *Python* | Angolan Python | *Lampropeltis* | Andean Milk Snake |
| *Python* | Angolan Python | *Lampropeltis* | Florida Kingsnake |
| *Python* | Angolan Python | *Lampropeltis* | Sinaloan Milk Snake |
| *Python* | Angolan Python | *Lampropeltis* | Black Milk Snake |
| *Python* | Angolan Python | *Morelia* | Coastal Carpet Python |
| *Python* | Angolan Python | *Morelia* | Jaguar Carpet Python |
| *Python* | Angolan Python | *Morelia* | Darwin Carpet Python |
| *Python* | Angolan Python | *Morelia* | Irian Jaya Carpet Python |
| *Python* | Angolan Python | *Morelia* | Carpet Python |
| *Python* | Angolan Python | *Orthriophis* | Mussurana (Clelia clelia) |
| *Python* | Angolan Python | *Orthriophis* | Yunnan Beauty Snake |

*Fig. 1 (cont.)*

| First Snake Species | | Second Snake Species | |
|---|---|---|---|
| Genus | Common Name | Genus | Common Name |
| Python | Angolan Python | Pantherophis | Corn Snake |
| Python | Angolan Python | Philodryas | Baron's Racer |
| Python | Angolan Python | Pituophis | Sonoran Gopher Snake |
| Python | Angolan Python | Pituophis | Cape Gopher Snake |
| Python | Angolan Python | Pituophis | Bull Snake |
| Python | Angolan Python | Python | Jampea Reticulated Python |
| Python | Angolan Python | Python | Reticulated Python |
| Python | Angolan Python | Python | Blood Python |
| Python | Angolan Python | Python | Ball Python |
| Python | Angolan Python | Rhamphiophis | Red Beaked Snakes |
| Python | Angolan Python | Spilotes | Tiger Rat Snake |
| Python | Angolan Python | Toxicodryas | Blandings Tree Snake |
| Python | Angolan Python | Lampropeltis x Elaphe HYBRID | California Cornsnake Hybrid |
| Python | Angolan Python | Aspidites x Python HYBRID | Woma x Ball Python Hyrbid |
| Python | Angolan Python | Xenopeltis | Sunbeam |
| Python | Jampea Reticulated Python | Aspidites | Woma |
| Python | Jampea Reticulated Python | Boa | Sonoran Boa Constrictor |
| Python | Jampea Reticulated Python | Boa | Boa Constrictor |
| Python | Jampea Reticulated Python | Boa | Tarahumara Boa Constrictor |
| Python | Jampea Reticulated Python | Boiga | Dog Toothed Cat Snake |
| Python | Jampea Reticulated Python | Boiruna | Mussurana (Boiruna maculata) |
| Python | Jampea Reticulated Python | Corallus | Amazon Tree Boa |
| Python | Jampea Reticulated Python | Drymarchon | Unicolor Cribo |
| Python | Jampea Reticulated Python | Drymarchon | Black Tailed Cribo |
| Python | Jampea Reticulated Python | Drymarchon | Yellow Tailed Cribo |
| Python | Jampea Reticulated Python | Elaphe | King Rat Snake |
| Python | Jampea Reticulated Python | Elaphe | Chinese Beauty Snake |
| Python | Jampea Reticulated Python | Gonionotophis | Cape File Snake |
| Python | Jampea Reticulated Python | Gonionotophis | West African File Snake |
| Python | Jampea Reticulated Python | Heloderma | Beaded Lizard |
| Python | Jampea Reticulated Python | Hydrodynastes | False Water Cobra |
| Python | Jampea Reticulated Python | Lampropeltis | Honduran Milk Snake |
| Python | Jampea Reticulated Python | Lampropeltis | Speckled Kingsnake |
| Python | Jampea Reticulated Python | Lampropeltis | Atlantic Milk Snake |
| Python | Jampea Reticulated Python | Lampropeltis | Desert Kingsnake |
| Python | Jampea Reticulated Python | Lampropeltis | Eastern Kingsnake |
| Python | Jampea Reticulated Python | Lampropeltis | California Kingsnake |
| Python | Jampea Reticulated Python | Lampropeltis | Andean Milk Snake |

*Fig. 1 (cont.)*

| First Snake Species | | Second Snake Species | |
|---|---|---|---|
| Genus | Common Name | Genus | Common Name |
| Python | Jampea Reticulated Python | Lampropeltis | Florida Kingsnake |
| Python | Jampea Reticulated Python | Lampropeltis | Sinaloan Milk Snake |
| Python | Jampea Reticulated Python | Lampropeltis | Black Milk Snake |
| Python | Jampea Reticulated Python | Morelia | Coastal Carpet Python |
| Python | Jampea Reticulated Python | Morelia | Jaguar Carpet Python |
| Python | Jampea Reticulated Python | Morelia | Darwin Carpet Python |
| Python | Jampea Reticulated Python | Morelia | Irian Jaya Carpet Python |
| Python | Jampea Reticulated Python | Morelia | Carpet Python |
| Python | Jampea Reticulated Python | Orthriophis | Mussurana (Clelia clelia) |
| Python | Jampea Reticulated Python | Orthriophis | Yunnan Beauty Snake |
| Python | Jampea Reticulated Python | Pantherophis | Corn Snake |
| Python | Jampea Reticulated Python | Philodryas | Baron's Racer |
| Python | Jampea Reticulated Python | Pituophis | Sonoran Gopher Snake |
| Python | Jampea Reticulated Python | Pituophis | Cape Gopher Snake |
| Python | Jampea Reticulated Python | Pituophis | Bull Snake |
| Python | Jampea Reticulated Python | Python | Angolan Python |
| Python | Jampea Reticulated Python | Python | Reticulated Python |
| Python | Jampea Reticulated Python | Python | Blood Python |
| Python | Jampea Reticulated Python | Python | Ball Python |
| Python | Jampea Reticulated Python | Rhamphiophis | Red Beaked Snakes |
| Python | Jampea Reticulated Python | Spilotes | Tiger Rat Snake |
| Python | Jampea Reticulated Python | Toxicodryas | Blandings Tree Snake |
| Python | Jampea Reticulated Python | Lampropeltis x Elaphe HYBRID | California Cornsnake Hybrid |
| Python | Jampea Reticulated Python | Aspidites x Python HYBRID | Woma x Ball Python Hyrbid |
| Python | Jampea Reticulated Python | Xenopeltis | Sunbeam |
| Python | Reticulated Python | Aspidites | Woma |
| Python | Reticulated Python | Boa | Sonoran Boa Constrictor |
| Python | Reticulated Python | Boa | Boa Constrictor |
| Python | Reticulated Python | Boa | Tarahumara Boa Constrictor |
| Python | Reticulated Python | Boiga | Dog Toothed Cat Snake |
| Python | Reticulated Python | Boiruna | Mussurana (Boiruna maculata) |
| Python | Reticulated Python | Corallus | Amazon Tree Boa |
| Python | Reticulated Python | Drymarchon | Unicolor Cribo |
| Python | Reticulated Python | Drymarchon | Black Tailed Cribo |
| Python | Reticulated Python | Drymarchon | Yellow Tailed Cribo |
| Python | Reticulated Python | Elaphe | King Rat Snake |
| Python | Reticulated Python | Elaphe | Chinese Beauty Snake |
| Python | Reticulated Python | Gonionotophis | Cape File Snake |

Fig. 1 (cont.)

| First Snake Species | | Second Snake Species | |
|---|---|---|---|
| Genus | Common Name | Genus | Common Name |
| *Python* | Reticulated Python | *Gonionotophis* | West African File Snake |
| *Python* | Reticulated Python | *Heloderma* | Beaded Lizard |
| *Python* | Reticulated Python | *Hydrodynastes* | False Water Cobra |
| *Python* | Reticulated Python | *Lampropeltis* | Honduran Milk Snake |
| *Python* | Reticulated Python | *Lampropeltis* | Speckled Kingsnake |
| *Python* | Reticulated Python | *Lampropeltis* | Atlantic Milk Snake |
| *Python* | Reticulated Python | *Lampropeltis* | Desert Kingsnake |
| *Python* | Reticulated Python | *Lampropeltis* | Eastern Kingsnake |
| *Python* | Reticulated Python | *Lampropeltis* | California Kingsnake |
| *Python* | Reticulated Python | *Lampropeltis* | Andean Milk Snake |
| *Python* | Reticulated Python | *Lampropeltis* | Florida Kingsnake |
| *Python* | Reticulated Python | *Lampropeltis* | Sinaloan Milk Snake |
| *Python* | Reticulated Python | *Lampropeltis* | Black Milk Snake |
| *Python* | Reticulated Python | *Morelia* | Coastal Carpet Python |
| *Python* | Reticulated Python | *Morelia* | Jaguar Carpet Python |
| *Python* | Reticulated Python | *Morelia* | Darwin Carpet Python |
| *Python* | Reticulated Python | *Morelia* | Irian Jaya Carpet Python |
| *Python* | Reticulated Python | *Morelia* | Carpet Python |
| *Python* | Reticulated Python | *Orthriophis* | Mussurana (Clelia clelia) |
| *Python* | Reticulated Python | *Orthriophis* | Yunnan Beauty Snake |
| *Python* | Reticulated Python | *Pantherophis* | Corn Snake |
| *Python* | Reticulated Python | *Philodryas* | Baron's Racer |
| *Python* | Reticulated Python | *Pituophis* | Sonoran Gopher Snake |
| *Python* | Reticulated Python | *Pituophis* | Cape Gopher Snake |
| *Python* | Reticulated Python | *Pituophis* | Bull Snake |
| *Python* | Reticulated Python | *Python* | Angolan Python |
| *Python* | Reticulated Python | *Python* | Jampea Reticulated Python |
| *Python* | Reticulated Python | *Python* | Blood Python |
| *Python* | Reticulated Python | *Python* | Ball Python |
| *Python* | Reticulated Python | *Rhamphiophis* | Red Beaked Snakes |
| *Python* | Reticulated Python | *Spilotes* | Tiger Rat Snake |
| *Python* | Reticulated Python | *Toxicodryas* | Blandings Tree Snake |
| *Python* | Reticulated Python | *Lampropeltis x Elaphe* HYBRID | California Cornsnake Hybrid |
| *Python* | Reticulated Python | *Aspidites x Python* HYBRID | Woma x Ball Python Hyrbid |
| *Python* | Reticulated Python | *Xenopeltis* | Sunbeam |
| *Python* | Blood Python | *Aspidites* | Woma |
| *Python* | Blood Python | *Boa* | Sonoran Boa Constrictor |
| *Python* | Blood Python | *Boa* | Boa Constrictor |

*Fig. 1 (cont.)*

| First Snake Species | | Second Snake Species | |
|---|---|---|---|
| Genus | Common Name | Genus | Common Name |
| *Python* | Blood Python | *Boa* | Tarahumara Boa Constrictor |
| *Python* | Blood Python | *Boiga* | Dog Toothed Cat Snake |
| *Python* | Blood Python | *Boiruna* | Mussurana (Boiruna maculata) |
| *Python* | Blood Python | *Corallus* | Amazon Tree Boa |
| *Python* | Blood Python | *Drymarchon* | Unicolor Cribo |
| *Python* | Blood Python | *Drymarchon* | Black Tailed Cribo |
| *Python* | Blood Python | *Drymarchon* | Yellow Tailed Cribo |
| *Python* | Blood Python | *Elaphe* | King Rat Snake |
| *Python* | Blood Python | *Elaphe* | Chinese Beauty Snake |
| *Python* | Blood Python | *Gonionotophis* | Cape File Snake |
| *Python* | Blood Python | *Gonionotophis* | West African File Snake |
| *Python* | Blood Python | *Heloderma* | Beaded Lizard |
| *Python* | Blood Python | *Hydrodynastes* | False Water Cobra |
| *Python* | Blood Python | *Lampropeltis* | Honduran Milk Snake |
| *Python* | Blood Python | *Lampropeltis* | Speckled Kingsnake |
| *Python* | Blood Python | *Lampropeltis* | Atlantic Milk Snake |
| *Python* | Blood Python | *Lampropeltis* | Desert Kingsnake |
| *Python* | Blood Python | *Lampropeltis* | Eastern Kingsnake |
| *Python* | Blood Python | *Lampropeltis* | California Kingsnake |
| *Python* | Blood Python | *Lampropeltis* | Andean Milk Snake |
| *Python* | Blood Python | *Lampropeltis* | Florida Kingsnake |
| *Python* | Blood Python | *Lampropeltis* | Sinaloan Milk Snake |
| *Python* | Blood Python | *Lampropeltis* | Black Milk Snake |
| *Python* | Blood Python | *Morelia* | Coastal Carpet Python |
| *Python* | Blood Python | *Morelia* | Jaguar Carpet Python |
| *Python* | Blood Python | *Morelia* | Darwin Carpet Python |
| *Python* | Blood Python | *Morelia* | Irian Jaya Carpet Python |
| *Python* | Blood Python | *Morelia* | Carpet Python |
| *Python* | Blood Python | *Orthriophis* | Mussurana (Cielia clelia) |
| *Python* | Blood Python | *Orthriophis* | Yunnan Beauty Snake |
| *Python* | Blood Python | *Pantherophis* | Corn Snake |
| *Python* | Blood Python | *Philodryas* | Baron's Racer |
| *Python* | Blood Python | *Pituophis* | Sonoran Gopher Snake |
| *Python* | Blood Python | *Pituophis* | Cape Gopher Snake |
| *Python* | Blood Python | *Pituophis* | Bull Snake |
| *Python* | Blood Python | *Python* | Angolan Python |
| *Python* | Blood Python | *Python* | Jampea Reticulated Python |
| *Python* | Blood Python | *Python* | Reticulated Python |
| *Python* | Blood Python | *Python* | Ball Python |
| *Python* | Blood Python | *Rhamphiophis* | Red Beaked Snakes |

*Fig. 1 (cont.)*

| First Snake Species | | Second Snake Species | |
|---|---|---|---|
| Genus | Common Name | Genus | Common Name |
| *Python* | Blood Python | *Spilotes* | Tiger Rat Snake |
| *Python* | Blood Python | *Toxicodryas* | Blandings Tree Snake |
| *Python* | Blood Python | *Lampropeltis x Elaphe* HYBRID | California Cornsnake Hybrid |
| *Python* | Blood Python | *Aspidites x Python* HYBRID | Woma x Ball Python Hyrbid |
| *Python* | Blood Python | *Xenopeltis* | Sunbeam |
| *Python* | Ball Python | *Aspidites* | Woma |
| *Python* | Ball Python | *Boa* | Sonoran Boa Constrictor |
| *Python* | Ball Python | *Boa* | Boa Constrictor |
| *Python* | Ball Python | *Boa* | Tarahumara Boa Constrictor |
| *Python* | Ball Python | *Boiga* | Dog Toothed Cat Snake |
| *Python* | Ball Python | *Boiruna* | Mussurana (Boiruna maculata) |
| *Python* | Ball Python | *Corallus* | Amazon Tree Boa |
| *Python* | Ball Python | *Drymarchon* | Unicolor Cribo |
| *Python* | Ball Python | *Drymarchon* | Black Tailed Cribo |
| *Python* | Ball Python | *Drymarchon* | Yellow Tailed Cribo |
| *Python* | Ball Python | *Elaphe* | King Rat Snake |
| *Python* | Ball Python | *Elaphe* | Chinese Beauty Snake |
| *Python* | Ball Python | *Gonionotophis* | Cape File Snake |
| *Python* | Ball Python | *Gonionotophis* | West African File Snake |
| *Python* | Ball Python | *Heloderma* | Beaded Lizard |
| *Python* | Ball Python | *Hydrodynastes* | False Water Cobra |
| *Python* | Ball Python | *Lampropeltis* | Honduran Milk Snake |
| *Python* | Ball Python | *Lampropeltis* | Speckled Kingsnake |
| *Python* | Ball Python | *Lampropeltis* | Atlantic Milk Snake |
| *Python* | Ball Python | *Lampropeltis* | Desert Kingsnake |
| *Python* | Ball Python | *Lampropeltis* | Eastern Kingsnake |
| *Python* | Ball Python | *Lampropeltis* | California Kingsnake |
| *Python* | Ball Python | *Lampropeltis* | Andean Milk Snake |
| *Python* | Ball Python | *Lampropeltis* | Florida Kingsnake |
| *Python* | Ball Python | *Lampropeltis* | Sinaloan Milk Snake |
| *Python* | Ball Python | *Lampropeltis* | Black Milk Snake |
| *Python* | Ball Python | *Morelia* | Coastal Carpet Python |
| *Python* | Ball Python | *Morelia* | Jaguar Carpet Python |
| *Python* | Ball Python | *Morelia* | Darwin Carpet Python |
| *Python* | Ball Python | *Morelia* | Irian Jaya Carpet Python |
| *Python* | Ball Python | *Morelia* | Carpet Python |
| *Python* | Ball Python | *Orthriophis* | Mussurana (Clelia clelia) |
| *Python* | Ball Python | *Orthriophis* | Yunnan Beauty Snake |

*Fig. 1 (cont.)*

| First Snake Species | | Second Snake Species | |
|---|---|---|---|
| Genus | Common Name | Genus | Common Name |
| *Python* | Ball Python | *Pantherophis* | Corn Snake |
| *Python* | Ball Python | *Philodryas* | Baron's Racer |
| *Python* | Ball Python | *Pituophis* | Sonoran Gopher Snake |
| *Python* | Ball Python | *Pituophis* | Cape Gopher Snake |
| *Python* | Ball Python | *Pituophis* | Bull Snake |
| *Python* | Ball Python | *Python* | Angolan Python |
| *Python* | Ball Python | *Python* | Jampea Reticulated Python |
| *Python* | Ball Python | *Python* | Reticulated Python |
| *Python* | Ball Python | *Python* | Blood Python |
| *Python* | Ball Python | *Rhamphiophis* | Red Beaked Snakes |
| *Python* | Ball Python | *Spilotes* | Tiger Rat Snake |
| *Python* | Ball Python | *Toxicodryas* | Blandings Tree Snake |
| *Python* | Ball Python | *Lampropeltis x Elaphe* HYBRID | California Cornsnake Hybrid |
| *Python* | Ball Python | *Aspidites x Python* HYBRID | Woma x Ball Python Hyrbid |
| *Python* | Ball Python | *Xenopeltis* | Sunbeam |
| *Rhamphiophis* | Red Beaked Snakes | *Aspidites* | Woma |
| *Rhamphiophis* | Red Beaked Snakes | *Boa* | Sonoran Boa Constrictor |
| *Rhamphiophis* | Red Beaked Snakes | *Boa* | Boa Constrictor |
| *Rhamphiophis* | Red Beaked Snakes | *Boa* | Tarahumara Boa Constrictor |
| *Rhamphiophis* | Red Beaked Snakes | *Boiga* | Dog Toothed Cat Snake |
| *Rhamphiophis* | Red Beaked Snakes | *Boiruna* | Mussurana (Boiruna maculata) |
| *Rhamphiophis* | Red Beaked Snakes | *Corallus* | Amazon Tree Boa |
| *Rhamphiophis* | Red Beaked Snakes | *Drymarchon* | Unicolor Cribo |
| *Rhamphiophis* | Red Beaked Snakes | *Drymarchon* | Black Tailed Cribo |
| *Rhamphiophis* | Red Beaked Snakes | *Drymarchon* | Yellow Tailed Cribo |
| *Rhamphiophis* | Red Beaked Snakes | *Elaphe* | King Rat Snake |
| *Rhamphiophis* | Red Beaked Snakes | *Elaphe* | Chinese Beauty Snake |
| *Rhamphiophis* | Red Beaked Snakes | *Gonionotophis* | Cape File Snake |
| *Rhamphiophis* | Red Beaked Snakes | *Gonionotophis* | West African File Snake |
| *Rhamphiophis* | Red Beaked Snakes | *Heloderma* | Beaded Lizard |
| *Rhamphiophis* | Red Beaked Snakes | *Hydrodynastes* | False Water Cobra |
| *Rhamphiophis* | Red Beaked Snakes | *Lampropeltis* | Honduran Milk Snake |
| *Rhamphiophis* | Red Beaked Snakes | *Lampropeltis* | Speckled Kingsnake |
| *Rhamphiophis* | Red Beaked Snakes | *Lampropeltis* | Atlantic Milk Snake |
| *Rhamphiophis* | Red Beaked Snakes | *Lampropeltis* | Desert Kingsnake |
| *Rhamphiophis* | Red Beaked Snakes | *Lampropeltis* | Eastern Kingsnake |
| *Rhamphiophis* | Red Beaked Snakes | *Lampropeltis* | California Kingsnake |
| *Rhamphiophis* | Red Beaked Snakes | *Lampropeltis* | Andean Milk Snake |

*Fig. 1 (cont.)*

| First Snake Species | | Second Snake Species | |
|---|---|---|---|
| Genus | Common Name | Genus | Common Name |
| *Rhamphiophis* | Red Beaked Snakes | *Lampropeltis* | Florida Kingsnake |
| *Rhamphiophis* | Red Beaked Snakes | *Lampropeltis* | Sinaloan Milk Snake |
| *Rhamphiophis* | Red Beaked Snakes | *Lampropeltis* | Black Milk Snake |
| *Rhamphiophis* | Red Beaked Snakes | *Morelia* | Coastal Carpet Python |
| *Rhamphiophis* | Red Beaked Snakes | *Morelia* | Jaguar Carpet Python |
| *Rhamphiophis* | Red Beaked Snakes | *Morelia* | Darwin Carpet Python |
| *Rhamphiophis* | Red Beaked Snakes | *Morelia* | Irian Jaya Carpet Python |
| *Rhamphiophis* | Red Beaked Snakes | *Morelia* | Carpet Python |
| *Rhamphiophis* | Red Beaked Snakes | *Orthriophis* | Mussurana (Clelia clelia) |
| *Rhamphiophis* | Red Beaked Snakes | *Orthriophis* | Yunnan Beauty Snake |
| *Rhamphiophis* | Red Beaked Snakes | *Pantherophis* | Corn Snake |
| *Rhamphiophis* | Red Beaked Snakes | *Philodryas* | Baron's Racer |
| *Rhamphiophis* | Red Beaked Snakes | *Pituophis* | Sonoran Gopher Snake |
| *Rhamphiophis* | Red Beaked Snakes | *Pituophis* | Cape Gopher Snake |
| *Rhamphiophis* | Red Beaked Snakes | *Pituophis* | Bull Snake |
| *Rhamphiophis* | Red Beaked Snakes | *Python* | Angolan Python |
| *Rhamphiophis* | Red Beaked Snakes | *Python* | Jampea Reticulated Python |
| *Rhamphiophis* | Red Beaked Snakes | *Python* | Reticulated Python |
| *Rhamphiophis* | Red Beaked Snakes | *Python* | Blood Python |
| *Rhamphiophis* | Red Beaked Snakes | *Python* | Ball Python |
| *Rhamphiophis* | Red Beaked Snakes | *Spilotes* | Tiger Rat Snake |
| *Rhamphiophis* | Red Beaked Snakes | *Toxicodryas* | Blandings Tree Snake |
| *Rhamphiophis* | Red Beaked Snakes | *Lampropeltis x Elaphe* HYBRID | California Cornsnake Hybrid |
| *Rhamphiophis* | Red Beaked Snakes | *Aspidites x Python* HYBRID | Woma x Ball Python Hyrbid |
| *Rhamphiophis* | Red Beaked Snakes | *Xenopeltis* | Sunbeam |
| *Spilotes* | Tiger Rat Snake | *Aspidites* | Woma |
| *Spilotes* | Tiger Rat Snake | *Boa* | Sonoran Boa Constrictor |
| *Spilotes* | Tiger Rat Snake | *Boa* | Boa Constrictor |
| *Spilotes* | Tiger Rat Snake | *Boa* | Tarahumara Boa Constrictor |
| *Spilotes* | Tiger Rat Snake | *Boiga* | Dog Toothed Cat Snake |
| *Spilotes* | Tiger Rat Snake | *Boiruna* | Mussurana (Boiruna maculata) |
| *Spilotes* | Tiger Rat Snake | *Corallus* | Amazon Tree Boa |
| *Spilotes* | Tiger Rat Snake | *Drymarchon* | Unicolor Cribo |
| *Spilotes* | Tiger Rat Snake | *Drymarchon* | Black Tailed Cribo |
| *Spilotes* | Tiger Rat Snake | *Drymarchon* | Yellow Tailed Cribo |
| *Spilotes* | Tiger Rat Snake | *Elaphe* | King Rat Snake |
| *Spilotes* | Tiger Rat Snake | *Elaphe* | Chinese Beauty Snake |
| *Spilotes* | Tiger Rat Snake | *Gonionotophis* | Cape File Snake |

*Fig. 1 (cont.)*

| First Snake Species | | Second Snake Species | |
|---|---|---|---|
| Genus | Common Name | Genus | Common Name |
| *Spilotes* | Tiger Rat Snake | *Gonionotophis* | West African File Snake |
| *Spilotes* | Tiger Rat Snake | *Heloderma* | Beaded Lizard |
| *Spilotes* | Tiger Rat Snake | *Hydrodynastes* | False Water Cobra |
| *Spilotes* | Tiger Rat Snake | *Lampropeltis* | Honduran Milk Snake |
| *Spilotes* | Tiger Rat Snake | *Lampropeltis* | Speckled Kingsnake |
| *Spilotes* | Tiger Rat Snake | *Lampropeltis* | Atlantic Milk Snake |
| *Spilotes* | Tiger Rat Snake | *Lampropeltis* | Desert Kingsnake |
| *Spilotes* | Tiger Rat Snake | *Lampropeltis* | Eastern Kingsnake |
| *Spilotes* | Tiger Rat Snake | *Lampropeltis* | California Kingsnake |
| *Spilotes* | Tiger Rat Snake | *Lampropeltis* | Andean Milk Snake |
| *Spilotes* | Tiger Rat Snake | *Lampropeltis* | Florida Kingsnake |
| *Spilotes* | Tiger Rat Snake | *Lampropeltis* | Sinaloan Milk Snake |
| *Spilotes* | Tiger Rat Snake | *Lampropeltis* | Black Milk Snake |
| *Spilotes* | Tiger Rat Snake | *Morelia* | Coastal Carpet Python |
| *Spilotes* | Tiger Rat Snake | *Morelia* | Jaguar Carpet Python |
| *Spilotes* | Tiger Rat Snake | *Morelia* | Darwin Carpet Python |
| *Spilotes* | Tiger Rat Snake | *Morelia* | Irian Jaya Carpet Python |
| *Spilotes* | Tiger Rat Snake | *Morelia* | Carpet Python |
| *Spilotes* | Tiger Rat Snake | *Orthriophis* | Mussurana (Clelia clelia) |
| *Spilotes* | Tiger Rat Snake | *Orthriophis* | Yunnan Beauty Snake |
| *Spilotes* | Tiger Rat Snake | *Pantherophis* | Corn Snake |
| *Spilotes* | Tiger Rat Snake | *Philodryas* | Baron's Racer |
| *Spilotes* | Tiger Rat Snake | *Pituophis* | Sonoran Gopher Snake |
| *Spilotes* | Tiger Rat Snake | *Pituophis* | Cape Gopher Snake |
| *Spilotes* | Tiger Rat Snake | *Pituophis* | Bull Snake |
| *Spilotes* | Tiger Rat Snake | *Python* | Angolan Python |
| *Spilotes* | Tiger Rat Snake | *Python* | Jampea Reticulated Python |
| *Spilotes* | Tiger Rat Snake | *Python* | Reticulated Python |
| *Spilotes* | Tiger Rat Snake | *Python* | Blood Python |
| *Spilotes* | Tiger Rat Snake | *Python* | Ball Python |
| *Spilotes* | Tiger Rat Snake | *Rhamphiophis* | Red Beaked Snakes |
| *Spilotes* | Tiger Rat Snake | *Toxicodryas* | Blandings Tree Snake |
| *Spilotes* | Tiger Rat Snake | *Lampropeltis x Elaphe* HYBRID | California Cornsnake Hybrid |
| *Spilotes* | Tiger Rat Snake | *Aspidites x Python* HYBRID | Woma x Ball Python Hyrbid |
| *Spilotes* | Tiger Rat Snake | *Xenopeltis* | Sunbeam |
| *Toxicodryas* | Blandings Tree Snake | *Aspidites* | Woma |
| *Toxicodryas* | Blandings Tree Snake | *Boa* | Sonoran Boa Constrictor |
| *Toxicodryas* | Blandings Tree Snake | *Boa* | Boa Constrictor |

*Fig. 1 (cont.)*

| First Snake Species | | Second Snake Species | |
|---|---|---|---|
| Genus | Common Name | Genus | Common Name |
| *Toxicodryas* | Blandings Tree Snake | *Boa* | Tarahumara Boa Constrictor |
| *Toxicodryas* | Blandings Tree Snake | *Boiga* | Dog Toothed Cat Snake |
| *Toxicodryas* | Blandings Tree Snake | *Boiruna* | Mussurana (Boiruna maculata) |
| *Toxicodryas* | Blandings Tree Snake | *Corallus* | Amazon Tree Boa |
| *Toxicodryas* | Blandings Tree Snake | *Drymarchon* | Unicolor Cribo |
| *Toxicodryas* | Blandings Tree Snake | *Drymarchon* | Black Tailed Cribo |
| *Toxicodryas* | Blandings Tree Snake | *Drymarchon* | Yellow Tailed Cribo |
| *Toxicodryas* | Blandings Tree Snake | *Elaphe* | King Rat Snake |
| *Toxicodryas* | Blandings Tree Snake | *Elaphe* | Chinese Beauty Snake |
| *Toxicodryas* | Blandings Tree Snake | *Gonionotophis* | Cape File Snake |
| *Toxicodryas* | Blandings Tree Snake | *Gonionotophis* | West African File Snake |
| *Toxicodryas* | Blandings Tree Snake | *Heloderma* | Beaded Lizard |
| *Toxicodryas* | Blandings Tree Snake | *Hydrodynastes* | False Water Cobra |
| *Toxicodryas* | Blandings Tree Snake | *Lampropeltis* | Honduran Milk Snake |
| *Toxicodryas* | Blandings Tree Snake | *Lampropeltis* | Speckled Kingsnake |
| *Toxicodryas* | Blandings Tree Snake | *Lampropeltis* | Atlantic Milk Snake |
| *Toxicodryas* | Blandings Tree Snake | *Lampropeltis* | Desert Kingsnake |
| *Toxicodryas* | Blandings Tree Snake | *Lampropeltis* | Eastern Kingsnake |
| *Toxicodryas* | Blandings Tree Snake | *Lampropeltis* | California Kingsnake |
| *Toxicodryas* | Blandings Tree Snake | *Lampropeltis* | Andean Milk Snake |
| *Toxicodryas* | Blandings Tree Snake | *Lampropeltis* | Florida Kingsnake |
| *Toxicodryas* | Blandings Tree Snake | *Lampropeltis* | Sinaloan Milk Snake |
| *Toxicodryas* | Blandings Tree Snake | *Lampropeltis* | Black Milk Snake |
| *Toxicodryas* | Blandings Tree Snake | *Morelia* | Coastal Carpet Python |
| *Toxicodryas* | Blandings Tree Snake | *Morelia* | Jaguar Carpet Python |
| *Toxicodryas* | Blandings Tree Snake | *Morelia* | Darwin Carpet Python |
| *Toxicodryas* | Blandings Tree Snake | *Morelia* | Irian Jaya Carpet Python |
| *Toxicodryas* | Blandings Tree Snake | *Morelia* | Carpet Python |
| *Toxicodryas* | Blandings Tree Snake | *Orthriophis* | Mussurana (Cielia clelia) |
| *Toxicodryas* | Blandings Tree Snake | *Orthriophis* | Yunnan Beauty Snake |
| *Toxicodryas* | Blandings Tree Snake | *Pantherophis* | Corn Snake |
| *Toxicodryas* | Blandings Tree Snake | *Philodryas* | Baron's Racer |
| *Toxicodryas* | Blandings Tree Snake | *Pituophis* | Sonoran Gopher Snake |
| *Toxicodryas* | Blandings Tree Snake | *Pituophis* | Cape Gopher Snake |
| *Toxicodryas* | Blandings Tree Snake | *Pituophis* | Bull Snake |
| *Toxicodryas* | Blandings Tree Snake | *Python* | Angolan Python |
| *Toxicodryas* | Blandings Tree Snake | *Python* | Jampea Reticulated Python |
| *Toxicodryas* | Blandings Tree Snake | *Python* | Reticulated Python |
| *Toxicodryas* | Blandings Tree Snake | *Python* | Blood Python |
| *Toxicodryas* | Blandings Tree Snake | *Python* | Ball Python |

*Fig. 1 (cont.)*

| First Snake Species | | Second Snake Species | |
|---|---|---|---|
| Genus | Common Name | Genus | Common Name |
| Toxicodryas | Blandings Tree Snake | Rhamphiophis | Red Beaked Snakes |
| Toxicodryas | Blandings Tree Snake | Spilotes | Tiger Rat Snake |
| Toxicodryas | Blandings Tree Snake | Lampropeltis x Elaphe HYBRID | California Cornsnake Hybrid |
| Toxicodryas | Blandings Tree Snake | Aspidites x Python HYBRID | Woma x Ball Python Hyrbid |
| Toxicodryas | Blandings Tree Snake | Xenopeltis | Sunbeam |
| Lampropeltis x Elaphe HYBRID | California Cornsnake Hybrid | Aspidites | Woma |
| Lampropeltis x Elaphe HYBRID | California Cornsnake Hybrid | Boa | Sonoran Boa Constrictor |
| Lampropeltis x Elaphe HYBRID | California Cornsnake Hybrid | Boa | Boa Constrictor |
| Lampropeltis x Elaphe HYBRID | California Cornsnake Hybrid | Boa | Tarahumara Boa Constrictor |
| Lampropeltis x Elaphe HYBRID | California Cornsnake Hybrid | Boiga | Dog Toothed Cat Snake |
| Lampropeltis x Elaphe HYBRID | California Cornsnake Hybrid | Boiruna | Mussurana (Boiruna maculata) |
| Lampropeltis x Elaphe HYBRID | California Cornsnake Hybrid | Corallus | Amazon Tree Boa |
| Lampropeltis x Elaphe HYBRID | California Cornsnake Hybrid | Drymarchon | Unicolor Cribo |
| Lampropeltis x Elaphe HYBRID | California Cornsnake Hybrid | Drymarchon | Black Tailed Cribo |
| Lampropeltis x Elaphe HYBRID | California Cornsnake Hybrid | Drymarchon | Yellow Tailed Cribo |
| Lampropeltis x Elaphe HYBRID | California Cornsnake Hybrid | Elaphe | King Rat Snake |
| Lampropeltis x Elaphe HYBRID | California Cornsnake Hybrid | Elaphe | Chinese Beauty Snake |
| Lampropeltis x Elaphe HYBRID | California Cornsnake Hybrid | Gonionotophis | Cape File Snake |
| Lampropeltis x Elaphe HYBRID | California Cornsnake Hybrid | Gonionotophis | West African File Snake |
| Lampropeltis x Elaphe HYBRID | California Cornsnake Hybrid | Heloderma | Beaded Lizard |
| Lampropeltis x Elaphe HYBRID | California Cornsnake Hybrid | Hydrodynastes | False Water Cobra |
| Lampropeltis x Elaphe HYBRID | California Cornsnake Hybrid | Lampropeltis | Honduran Milk Snake |
| Lampropeltis x Elaphe HYBRID | California Cornsnake Hybrid | Lampropeltis | Speckled Kingsnake |

Fig. 1 (cont.)

| First Snake Species | | Second Snake Species | |
|---|---|---|---|
| Genus | Common Name | Genus | Common Name |
| Lampropeltis x Elaphe HYBRID | California Cornsnake Hybrid | Lampropeltis | Atlantic Milk Snake |
| Lampropeltis x Elaphe HYBRID | California Cornsnake Hybrid | Lampropeltis | Desert Kingsnake |
| Lampropeltis x Elaphe HYBRID | California Cornsnake Hybrid | Lampropeltis | Eastern Kingsnake |
| Lampropeltis x Elaphe HYBRID | California Cornsnake Hybrid | Lampropeltis | California Kingsnake |
| Lampropeltis x Elaphe HYBRID | California Cornsnake Hybrid | Lampropeltis | Andean Milk Snake |
| Lampropeltis x Elaphe HYBRID | California Cornsnake Hybrid | Lampropeltis | Florida Kingsnake |
| Lampropeltis x Elaphe HYBRID | California Cornsnake Hybrid | Lampropeltis | Sinaloan Milk Snake |
| Lampropeltis x Elaphe HYBRID | California Cornsnake Hybrid | Lampropeltis | Black Milk Snake |
| Lampropeltis x Elaphe HYBRID | California Cornsnake Hybrid | Morelia | Coastal Carpet Python |
| Lampropeltis x Elaphe HYBRID | California Cornsnake Hybrid | Morelia | Jaguar Carpet Python |
| Lampropeltis x Elaphe HYBRID | California Cornsnake Hybrid | Morelia | Darwin Carpet Python |
| Lampropeltis x Elaphe HYBRID | California Cornsnake Hybrid | Morelia | Irian Jaya Carpet Python |
| Lampropeltis x Elaphe HYBRID | California Cornsnake Hybrid | Morelia | Carpet Python |
| Lampropeltis x Elaphe HYBRID | California Cornsnake Hybrid | Orthriophis | Mussurana (Clelia clelia) |
| Lampropeltis x Elaphe HYBRID | California Cornsnake Hybrid | Orthriophis | Yunnan Beauty Snake |
| Lampropeltis x Elaphe HYBRID | California Cornsnake Hybrid | Pantherophis | Corn Snake |
| Lampropeltis x Elaphe HYBRID | California Cornsnake Hybrid | Philodryas | Baron's Racer |
| Lampropeltis x Elaphe HYBRID | California Cornsnake Hybrid | Pituophis | Sonoran Gopher Snake |
| Lampropeltis x Elaphe HYBRID | California Cornsnake Hybrid | Pituophis | Cape Gopher Snake |
| Lampropeltis x Elaphe HYBRID | California Cornsnake Hybrid | Pituophis | Bull Snake |
| Lampropeltis x Elaphe HYBRID | California Cornsnake Hybrid | Python | Angolan Python |
| Lampropeltis x Elaphe HYBRID | California Cornsnake Hybrid | Python | Jampea Reticulated Python |

*Fig. 1 (cont.)*

| First Snake Species | | Second Snake Species | |
|---|---|---|---|
| Genus | Common Name | Genus | Common Name |
| *Elaphe* HYBRID | | | |
| *Lampropeltis x Elaphe* HYBRID | California Cornsnake Hybrid | *Python* | Reticulated Python |
| *Lampropeltis x Elaphe* HYBRID | California Cornsnake Hybrid | *Python* | Blood Python |
| *Lampropeltis x Elaphe* HYBRID | California Cornsnake Hybrid | *Python* | Ball Python |
| *Lampropeltis x Elaphe* HYBRID | California Cornsnake Hybrid | *Rhamphiophis* | Red Beaked Snakes |
| *Lampropeltis x Elaphe* HYBRID | California Cornsnake Hybrid | *Spilotes* | Tiger Rat Snake |
| *Lampropeltis x Elaphe* HYBRID | California Cornsnake Hybrid | *Toxicodryas* | Blandings Tree Snake |
| *Lampropeltis x Elaphe* HYBRID | California Cornsnake Hybrid | *Aspidites x Python* HYBRID | Woma x Ball Python Hyrbid |
| *Lampropeltis x Elaphe* HYBRID | California Cornsnake Hybrid | *Xenopeltis* | Sunbeam |
| *Aspidites x Python* HYBRID | Woma x Ball Python Hyrbid | *Aspidites* | Woma |
| *Aspidites x Python* HYBRID | Woma x Ball Python Hyrbid | *Boa* | Sonoran Boa Constrictor |
| *Aspidites x Python* HYBRID | Woma x Ball Python Hyrbid | *Boa* | Boa Constrictor |
| *Aspidites x Python* HYBRID | Woma x Ball Python Hyrbid | *Boa* | Tarahumara Boa Constrictor |
| *Aspidites x Python* HYBRID | Woma x Ball Python Hyrbid | *Boiga* | Dog Toothed Cat Snake |
| *Aspidites x Python* HYBRID | Woma x Ball Python Hyrbid | *Boiruna* | Mussurana (Boiruna maculata) |
| *Aspidites x Python* HYBRID | Woma x Ball Python Hyrbid | *Corallus* | Amazon Tree Boa |
| *Aspidites x Python* HYBRID | Woma x Ball Python Hyrbid | *Drymarchon* | Unicolor Cribo |
| *Aspidites x Python* HYBRID | Woma x Ball Python Hyrbid | *Drymarchon* | Black Tailed Cribo |
| *Aspidites x Python* HYBRID | Woma x Ball Python Hyrbid | *Drymarchon* | Yellow Tailed Cribo |
| *Aspidites x Python* HYBRID | Woma x Ball Python Hyrbid | *Elaphe* | King Rat Snake |
| *Aspidites x Python* HYBRID | Woma x Ball Python Hyrbid | *Elaphe* | Chinese Beauty Snake |
| *Aspidites x Python* HYBRID | Woma x Ball Python Hyrbid | *Gonionotophis* | Cape File Snake |

*Fig. 1 (cont.)*

| First Snake Species | | Second Snake Species | |
|---|---|---|---|
| Genus | Common Name | Genus | Common Name |
| Aspidites x Python HYBRID | Woma x Ball Python Hyrbid | Gonionotophis | West African File Snake |
| Aspidites x Python HYBRID | Woma x Ball Python Hyrbid | Heloderma | Beaded Lizard |
| Aspidites x Python HYBRID | Woma x Ball Python Hyrbid | Hydrodynastes | False Water Cobra |
| Aspidites x Python HYBRID | Woma x Ball Python Hyrbid | Lampropeltis | Honduran Milk Snake |
| Aspidites x Python HYBRID | Woma x Ball Python Hyrbid | Lampropeltis | Speckled Kingsnake |
| Aspidites x Python HYBRID | Woma x Ball Python Hyrbid | Lampropeltis | Atlantic Milk Snake |
| Aspidites x Python HYBRID | Woma x Ball Python Hyrbid | Lampropeltis | Desert Kingsnake |
| Aspidites x Python HYBRID | Woma x Ball Python Hyrbid | Lampropeltis | Eastern Kingsnake |
| Aspidites x Python HYBRID | Woma x Ball Python Hyrbid | Lampropeltis | California Kingsnake |
| Aspidites x Python HYBRID | Woma x Ball Python Hyrbid | Lampropeltis | Andean Milk Snake |
| Aspidites x Python HYBRID | Woma x Ball Python Hyrbid | Lampropeltis | Florida Kingsnake |
| Aspidites x Python HYBRID | Woma x Ball Python Hyrbid | Lampropeltis | Sinaloan Milk Snake |
| Aspidites x Python HYBRID | Woma x Ball Python Hyrbid | Lampropeltis | Black Milk Snake |
| Aspidites x Python HYBRID | Woma x Ball Python Hyrbid | Morelia | Coastal Carpet Python |
| Aspidites x Python HYBRID | Woma x Ball Python Hyrbid | Morelia | Jaguar Carpet Python |
| Aspidites x Python HYBRID | Woma x Ball Python Hyrbid | Morelia | Darwin Carpet Python |
| Aspidites x Python HYBRID | Woma x Ball Python Hyrbid | Morelia | Irian Jaya Carpet Python |
| Aspidites x Python HYBRID | Woma x Ball Python Hyrbid | Morelia | Carpet Python |
| Aspidites x Python HYBRID | Woma x Ball Python Hyrbid | Orthriophis | Mussurana (Clelia clelia) |
| Aspidites x Python HYBRID | Woma x Ball Python Hyrbid | Orthriophis | Yunnan Beauty Snake |
| Aspidites x Python HYBRID | Woma x Ball Python Hyrbid | Pantherophis | Corn Snake |
| Aspidites x Python | Woma x Ball Python Hyrbid | Philodryas | Baron's Racer |

*Fig. 1 (cont.)*

| First Snake Species | | Second Snake Species | |
|---|---|---|---|
| Genus | Common Name | Genus | Common Name |
| HYBRID | | | |
| Aspidites x Python HYBRID | Woma x Ball Python Hyrbid | Pituophis | Sonoran Gopher Snake |
| Aspidites x Python HYBRID | Woma x Ball Python Hyrbid | Pituophis | Cape Gopher Snake |
| Aspidites x Python HYBRID | Woma x Ball Python Hyrbid | Pituophis | Bull Snake |
| Aspidites x Python HYBRID | Woma x Ball Python Hyrbid | Python | Angolan Python |
| Aspidites x Python HYBRID | Woma x Ball Python Hyrbid | Python | Jampea Reticulated Python |
| Aspidites x Python HYBRID | Woma x Ball Python Hyrbid | Python | Reticulated Python |
| Aspidites x Python HYBRID | Woma x Ball Python Hyrbid | Python | Blood Python |
| Aspidites x Python HYBRID | Woma x Ball Python Hyrbid | Python | Ball Python |
| Aspidites x Python HYBRID | Woma x Ball Python Hyrbid | Rhamphiophis | Red Beaked Snakes |
| Aspidites x Python HYBRID | Woma x Ball Python Hyrbid | Spilotes | Tiger Rat Snake |
| Aspidites x Python HYBRID | Woma x Ball Python Hyrbid | Toxicodryas | Blandings Tree Snake |
| Aspidites x Python HYBRID | Woma x Ball Python Hyrbid | Lampropeltis x Elaphe HYBRID | California Cornsnake Hybrid |
| Aspidites x Python HYBRID | Woma x Ball Python Hyrbid | Xenopeltis | Sunbeam |
| Xenopeltis | Sunbeam | Aspidites | Woma |
| Xenopeltis | Sunbeam | Boa | Sonoran Boa Constrictor |
| Xenopeltis | Sunbeam | Boa | Boa Constrictor |
| Xenopeltis | Sunbeam | Boa | Tarahumara Boa Constrictor |
| Xenopeltis | Sunbeam | Boiga | Dog Toothed Cat Snake |
| Xenopeltis | Sunbeam | Boiruna | Mussurana (Boiruna maculata) |
| Xenopeltis | Sunbeam | Corallus | Amazon Tree Boa |
| Xenopeltis | Sunbeam | Drymarchon | Unicolor Cribo |
| Xenopeltis | Sunbeam | Drymarchon | Black Tailed Cribo |
| Xenopeltis | Sunbeam | Drymarchon | Yellow Tailed Cribo |
| Xenopeltis | Sunbeam | Elaphe | King Rat Snake |
| Xenopeltis | Sunbeam | Elaphe | Chinese Beauty Snake |
| Xenopeltis | Sunbeam | Gonionotophis | Cape File Snake |
| Xenopeltis | Sunbeam | Gonionotophis | West African File Snake |
| Xenopeltis | Sunbeam | Heloderma | Beaded Lizard |

Fig. 1 (cont.)

| First Snake Species | | Second Snake Species | |
|---|---|---|---|
| Genus | Common Name | Genus | Common Name |
| *Xenopeltis* | Sunbeam | *Hydrodynastes* | False Water Cobra |
| *Xenopeltis* | Sunbeam | *Lampropeltis* | Honduran Milk Snake |
| *Xenopeltis* | Sunbeam | *Lampropeltis* | Speckled Kingsnake |
| *Xenopeltis* | Sunbeam | *Lampropeltis* | Atlantic Milk Snake |
| *Xenopeltis* | Sunbeam | *Lampropeltis* | Desert Kingsnake |
| *Xenopeltis* | Sunbeam | *Lampropeltis* | Eastern Kingsnake |
| *Xenopeltis* | Sunbeam | *Lampropeltis* | California Kingsnake |
| *Xenopeltis* | Sunbeam | *Lampropeltis* | Andean Milk Snake |
| *Xenopeltis* | Sunbeam | *Lampropeltis* | Florida Kingsnake |
| *Xenopeltis* | Sunbeam | *Lampropeltis* | Sinaloan Milk Snake |
| *Xenopeltis* | Sunbeam | *Lampropeltis* | Black Milk Snake |
| *Xenopeltis* | Sunbeam | *Morelia* | Coastal Carpet Python |
| *Xenopeltis* | Sunbeam | *Morelia* | Jaguar Carpet Python |
| *Xenopeltis* | Sunbeam | *Morelia* | Darwin Carpet Python |
| *Xenopeltis* | Sunbeam | *Morelia* | Irian Jaya Carpet Python |
| *Xenopeltis* | Sunbeam | *Morelia* | Carpet Python |
| *Xenopeltis* | Sunbeam | *Orthriophis* | Mussurana (Clelia clelia) |
| *Xenopeltis* | Sunbeam | *Orthriophis* | Yunnan Beauty Snake |
| *Xenopeltis* | Sunbeam | *Pantherophis* | Corn Snake |
| *Xenopeltis* | Sunbeam | *Philodryas* | Baron's Racer |
| *Xenopeltis* | Sunbeam | *Pituophis* | Sonoran Gopher Snake |
| *Xenopeltis* | Sunbeam | *Pituophis* | Cape Gopher Snake |
| *Xenopeltis* | Sunbeam | *Pituophis* | Bull Snake |
| *Xenopeltis* | Sunbeam | *Python* | Angolan Python |
| *Xenopeltis* | Sunbeam | *Python* | Jampea Reticulated Python |
| *Xenopeltis* | Sunbeam | *Python* | Reticulated Python |
| *Xenopeltis* | Sunbeam | *Python* | Blood Python |
| *Xenopeltis* | Sunbeam | *Python* | Ball Python |
| *Xenopeltis* | Sunbeam | *Rhamphiophis* | Red Beaked Snakes |
| *Xenopeltis* | Sunbeam | *Spilotes* | Tiger Rat Snake |
| *Xenopeltis* | Sunbeam | *Toxicodryas* | Blandings Tree Snake |
| *Xenopeltis* | Sunbeam | *Lampropeltis x Elaphe* HYBRID | California Cornsnake Hybrid |
| *Xenopeltis* | Sunbeam | *Aspidites x Python* HYBRID | Woma x Ball Python Hyrbid |

*Fig. 1 (cont.)*

ANTIVENOM COMPOSITIONS AND USES THEREOF

CROSS-REFERENCE TO RELATED APPLICATIONS

This application claims the benefit of and priority to U.S. Provisional Application No. 62/340,983, filed May 24, 2016, the entirety of which is incorporated herein by reference.

TECHNICAL FIELD

The subject matter described herein relates to therapeutic compositions derived from snake blood and methods for administering the compositions to victims of venomous snakebites.

BACKGROUND

Snakebites in humans are a neglected public health issue in many tropical and subtropical countries. About five million snakebites occur each year, resulting in up to 2.5 million envenomings (poisoning from snakebites), at least 100,000 deaths and around three times as many amputations and other permanent disabilities. Also, between 150,000 and 300,000 pets are bitten by Crotalids (pit vipers) each year in the USA. Many are put down rather than pay several thousand dollars for treatment.

Antivenom, or more specifically venom antibodies are recognized as the only effective treatment to prevent or reverse most of the venomous effects of venomous bites and stings. A significant challenge in manufacturing of antivenoms is the preparation of the correct immunogens (snake venoms). At present very few countries produce snake venoms of adequate quality for antivenom manufacture. In addition, lack of regulations and proper distribution management for antivenoms in countries with significant snakebite problems results in an inability to assess the quality and appropriateness of the antivenoms.

Autologous and analogous immunity to venoms has been well documented in folklore and science. For example, U.S. Pat. No. 4,150,118 describes the efficacy of a "material extracted from snakes such as snake serum [that] is purified to obtain an inhibitor for snake venom toxicity and/or proteolytic enzymes." However, the means of antivenom selection and collection was rudimentary.

Disclosed herein is the design and use of an efficient technique and technology to select, collect, purify and isolate autologous snake antivenom. Unlike current venom antibody production, this technology can greatly reduce or entirely eliminate the need for antigens (venom) and their use in hyperimmunization to provide a viable commercial product for treatment of snakebite victims.

SUMMARY

The following aspects and embodiments thereof described and illustrated below are meant to be exemplary and illustrative, not limiting in scope.

In one aspect, a method for treating a subject suffering from a venomous snakebite is provided comprising administering to the subject an antivenom composition comprising plasma obtained from at least one donor snake species.

In some embodiments, the antivenom composition comprises plasma from 1-5, 1-4, 1-3 or 1-2 donor snake species. In some embodiments, the composition comprises plasma from 1, 2 or 3 donor snake species.

In some embodiments, the at least one donor snake species is selected from the group consisting of Kingsnakes (*Lampropeltis* sp), Python snakes (*Python* sp), Indigo snakes (*Drymarchon* sp), Mussuranas (*Boiruna* sp), Rat snake (*Elaphe*) or File snakes (*Gonionotophis* sp).

In some embodiments, the antivenom composition comprises plasma from a first donor snake species and a second donor snake species, wherein the first and second donor snake species are different and are selected from the group consisting of Kingsnakes (*Lampropeltis* sp), Python snakes (*Python* sp), Indigo snakes (*Drymarchon* sp), Mussuranas (*Boiruna* sp), Rat snake (*Elaphe* sp) and File snakes (*Gonionotophis* sp).

In some embodiments, the ratio of the volume of plasma from the first donor snake to the volume of plasma from the second donor snake ranges from about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 5:1 to about 10:1, about 2:1 to about 5:1, about 2:1 to about 2:4, or about 2:1 to about 3:1. In some embodiments, the ratio of the volume of plasma from the first donor snake species to the volume of plasma from the second donor snake species is about 1:1, about 2:1, about 3:1, about 4:1, about 5:1, about 6:1, about 7:1, about 8:1, about 9:1, or about 10:1.

In some embodiments, the first snake species is a *Python* species and the second snake species is a *Lampropeltis* species.

In some embodiments, the donor snake species is a hybrid snake species, wherein the hybrid snake species is the offspring of two parental snake species from geographically isolated areas.

In some embodiments, the subject was bitten by a rattlesnake. In some embodiments, the rattlesnake is a snake selected from the group consisting of Southern Pacific Rattlesnake (*Crotalus oreganus helleri*), Western diamondback rattlesnake (*C. atrox*), Eastern diamondback rattlesnake (*C. adamanteus*), Pacific rattlesnake (*C. viridis viridis*), Mojave rattlesnake (*C. scutulatus scutulatus*), Timber rattlesnake (*C. horridus horridus*), and Florida ground rattlesnake (*Sistrurus miliarius barbouri*). In some embodiments, the subject was bitten by a Northern copperhead (*Agkistrodon contortrix mokasen*), or a Florida cottonmouth (*A. piscivorus conanti*).

In some embodiments, the subject is a mammal. In some embodiments, the subject is a domesticated animal. Further, in some embodiments, the subject is a dog. Furthermore, in some embodiments, the subject is a human.

In some embodiments, the administering is started within about 1 hour, about 2 hours, about 3 hours, about 4 hours, about 5 hours, about 6 hours, about 8 hours, about 10 hours, about 12 hours, about 14 hours, about 18 hours, about 20 hours, or about 24 hours after the subject was bitten by the snake.

In some embodiments, the subject is administered a dose of antivenom composition ranging from about 0.1 mL/kg to about 5 mL/kg, about 0.1 mL/kg to about 4 mL/kg, about 0.1 mL/kg to about 3 mL/kg, about 0.1 mL/kg to about 2 mL/kg, about 0.1 mL/kg to about 1 mL/kg, about 0.2 mL/kg to about 0.5 mL/kg. In some embodiments, about the dose is about 0.1 mL/kg, about 0.2 mL/kg, about 0.3 mL/kg, about 0.4 mL/kg, about 0.5 mL/kg, about 0.6 mL/kg, about 0.7 mL/kg, about 0.8 mL/kg, about 0.9 mL/kg, about 1 mL/kg, about 2 mL/kg, about 3 mL/kg, about 4 mL/kg or 5 mL/kg.

In some embodiments, the administering comprises an intravenous infusion of the antivenom composition in to about the subject. In some embodiments, the infusion is performed at a rate of about 100 mL/hr to about 200 mL/hr, about 100 mL/hr to about 300 mL/hr, about 100 mL/hr to about 150 mL/hr, about 75 mL/hr to about 150 mL/hr, about 5 mL/hr to about 20 mL/hr, about 5 mL/hr to about 15 mL/hr or 5 mL/hr to about 10 mL/hr. In some embodiments, the infusion is performed within a period of about 15 min, about 30 min, about 1 h, about 90 min, about 2 hours, about 4 hours, about 6 hours, about 8 hours, about 10 hours, about or 12 hours, or over a period of about 15 min to about 45 min, about 15 min to about 30 min, about 15 min to about 1 hour, about 30 min to about 1 hour, about 1 hour to about 4 hours, or about 30 min to about 6 hours.

In some embodiments, the subject is treated with a second infusion of the antivenom composition. In some embodiments, the second infusion of the antivenom composition is performed within or at about 1 hour, about 2 hours, about 4 hours, about 6 hours, about 8 hours, about 10 hours, about 12 hours, about 18 hours, about 24 hours, about 36 hours, about 48 hours, about 60 hours, or about 72 hours after the first infusion.

In some embodiments, the intravenous infusion is continued until the subject achieves a Snake Severity Score (SSS, as discussed further below) of about or below 4, about or below 3, about or below 2, or about or below 1. In some embodiments, the subject achieves a SSS of about or below 4, about or below 3, about or below 2, or about or below 1 within about 2 hours, about 4 hours, about 6 hours, about 8 hours, about 10 hours, about 12 hours, about 18 hours, about 24 hours, about 36 hours, about 48 hours, about 60 hours, or about 72 hours after the intravenous infusion. In some embodiments, the subject achieves a reduction in SSS of about 10, about 9, about 8, about 7, about 6, about 5, about 4, about 3, about 2, or about 1 within about 2 hours, about 4 hours, about 6 hours, about 8 hours, about 10 hours, about 12 hours, about 18 hours, about 24 hours, about 36 hours, about 48 hours, about 60 hours or about 72 hours after the intravenous infusion.

In some embodiments, the method of treatment is effective in reducing pain, wherein pain is measured using the Glasgow Composite Measure Pain Scale and wherein pain is reduced to a score of 0-3, 1-3, 2-3, or 0, 1, 2 or 3.

In some embodiments, the method of treatment is effective in reducing pain wherein pain is reduced by at least about 10%, about 20%, about 30%, about 40%, about 50%, about 60%, about 70%, about 80%, or about 90% after treatment. In some embodiments, pain reduction is assessed at 1 day, 2 days, 3 days, 4 days, 5 days, 6 days, 1 week, 10 days, or 2 weeks after any initial or subsequent infusion of the antivenom.

In some embodiments, the method of treatment reduces swelling of the snakebite area by about 10%, about 20%, about 30%, about 40%, about 50%, about 60%, about 70%, about 80%, or about 90% compared to swelling at the time the antivenom is administered. In some embodiments, swelling is assessed at 1 day, 2 days, 3 days, 4 days, 5 days, 6 days, 1 week, 10 days, or 2 weeks after administration of the antivenom.

In some embodiments, the subject is treated with a pain medication. For example, in some embodiments, the pain medication is methadone, fentanyl, or methadone. Further, in some embodiments, the subject is treated with one or more of the pain medications.

In some embodiments, the one or more pain medications is administered to the subject before administration of the antivenom. In some embodiments, the one or more pain medications is administered to the subject during administration of the antivenom. In some embodiments, the one or more pain medications is administered to the subject after administration of the antivenom.

In some embodiments, the subject is treated with an antiemetic. For example, in some embodiments, the antiemetic is maropitant or a pharmaceutical salt thereof.

In some embodiments, the antiemetic is administered to the subject before administration of the antivenom. In some embodiments, the antiemetic is administered to the subject during administration of the antivenom. In some embodiments, the antiemetic is administered to the subject after administration of the antivenom.

In another aspect, a method for preparing an antivenom composition is provided comprising obtaining plasma from the blood of a donor snake and fractionating the plasma to generate the antivenom composition. In some embodiments, the donor snake species is known to be immune to the pathological effects of autologous snake venom.

In some embodiments, the obtaining plasma from the blood of the donor snake comprises bleeding the snake until about 10% to about 20% or about 15% of the snake's blood is transferred to a sterile container.

In some embodiments, the method for preparing an antivenom composition comprises obtaining plasma from the blood of two or more donor snake species, wherein each of the two or more donor snake species is known to be immune to the pathological effects of autologous snake venom.

In some embodiments, the method further comprises isolating plasma from the blood to generate a plasma fraction. In some embodiments, the method further comprises pooling a plurality of the plasma fractions to generate a pool plasma composition.

In some embodiments, the method further comprises incubating the pooled plasma composition with an anticoagulant solution. In some embodiments, the incubating is performed at a temperature of about 2° C. to about 8° C. In some embodiments, the incubating is performed for a time period of about 1 hour to about 4 hours.

In some embodiments, the fractionating the plasma comprises centrifuging the pooled plasma followed by removing the precipitate.

In another aspect, a method for preparing an antivenom composition is provided comprising obtaining plasma from the blood of a venomous snake species and fractionating the plasma to generate the antivenom composition.

In another aspect, a composition is provided comprising a plasma fraction wherein the plasma fraction neutralizes adverse reactions to a venomous snakebite.

In some embodiments, the composition maintains at least about 75%, about 80%, about 85%, about 90%, about 95%, or about 100% of its antivenom activity if kept in a sterile container at room temperature. In some embodiments, the composition is kept at room temperature for at least 1 month, 4 months, 6 months, 9 months, 12 months, 18 months, or 1 year, wherein the composition maintains its antivenom activity.

In some embodiments, the antivenom composition further comprises pharmaceutically acceptable excipients.

In some embodiments, the donor snake species is selected from the group consisting of Kingsnakes (*Lampropeltis* sp), Pythons (*Python* sp.), Indigo snakes (*Drymarchon* sp), Mussuranas (*Boiruna* sp) or File snakes (*Gonionotophis* sp).

BRIEF DESCRIPTION OF THE DRAWINGS

Various features of illustrative embodiments of the inventions are described below with reference to the drawings.

The illustrated embodiments are intended to illustrate, but not to limit, the inventions. The drawings contain the following FIGURES:

FIG. 1 provides a table of example snake species pairs for formulating an antivenom composition described herein.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 mL to 8 mL is stated, it is intended that 2 mL, 3 mL, 4 mL, 5 mL, 6 mL, and 7 mL are also explicitly disclosed, as well as the range of values greater than or equal to 1 mL and the range of values less than or equal to 8 mL.

The term "antivenom" as used herein means a biological product or composition used in the treatment of venomous bites. An antivenom composition is therapeutically effective to reduce or eliminate the pathological effects of a venomous bit.

The term "therapeutic" as used herein means a treatment and/or prophylaxis. A therapeutic effect is obtained by suppression, remission, or eradication of a pathological state.

As used herein, a "therapeutically effective amount" is an amount required to produce a desired therapeutic effect. For example, in methods for treating a snakebite victim, a therapeutically effective amount is the amount required to reduce swelling by at least 5%, 10%, 20%, 25%, 30%, 35%, 40%, 45%, 50%, 55%, 60%, 65%, 70%, 75%, 80%, 85%, or 95% within about 2 hours, about 5 hours, about 10 hours, about 12 hours, about 15 hours, about 20 hours, about 24 hours, about 36 hours, about 48 hours, about 60 hours, or about 72 hours after administration of an antivenom. Alternatively, in methods for treating a snakebite victim, a therapeutically effective amount is the amount required to reduce pain by at least 5%, 10%, 20%, 25%, 30%, 35%, 40%, 45%, 50%, 55%, 60%, 65%, 70%, 75%, 80%, 85%, or 95% within about 2 hours, 5 hours, 10 hours, 12 hours, 15 hours, 20 hours, 24 hours, 36 hours, 48 hours, 60 hours, or 72 hours after administration of an antivenom.

The term "subject" or "patient" as used herein refers to an animal subject (e.g., canine) or a human subject, and may be used interchangeably with "victim" or "snakebite victim."

Snake Antivenom

The present disclosure relates to the treatment of snakebite victims using a composition that comprises antivenom components from a snake which is naturally resistant to one or more venomous snakes (autologous snake). In accordance with some embodiments disclosed herein, serum from these naturally resistant snakes has been shown to neutralize venom from other venomous species through mortality tests in mice.

Contemplated by the present disclosure are compositions derived from snake blood. Specifically, plasma obtained from the blood of venomous snakes is prepared then further fractionated to produce an antivenom composition. While the venom neutralization properties of certain venomous snakes have been known for centuries, no commercial products have been developed to exploit this property.

Venom-neutralizing properties of autologous snakes have been known since the mid-eighteenth century as many venomous species are immune to their own venoms. Further studies showed that venom neutralization properties of serum from individual snake species are effective against venom of different species of a given genus. For example, Weinstein et al. (J. Herpetology, 1992, 26:452-461) showed that serum from the *Lampropeltis* genus is able to neutralize venom from Crotaline snakes. Antivenom activity has also been identified in snake eggs (U.S. Pat. No. 4,150,118). However, the biological molecule or molecules responsible for the antivenom activity has not been identified to date and moreover has not been the basis for producing an antivenom therapeutic product for the reliable and convenient clinical treatment of snakebite victims. Described herein are methods for isolating an antivenom composition from the plasma or from the eggs of snakes wherein the composition can be reliably produced and stored as a dependable source for treatment of snakebite victims. Some of the advantages afforded by the compositions and methods include eliminating the need to obtain venom from venomous snakes for hyperimmunization, the need to maintain and immunize large mammals for current antivenom products, and the need to house venomous snakes. Additionally, antivenom compositions prepared from snake plasma and/or eggs are highly adapted to the venoms of venomous snakes, thereby providing broader protection than current antivenoms which are limited by the diversity of venoms which are collected from snakes.

To generate a therapeutic antivenom composition described herein, blood is obtained from a donor snake species such as but not limited to Kingsnake (*Lampropeltis* sp), Indigo snake (*Drymarchon* sp), Mussuranas (*Boiruna* sp), Rat snake (*Elaphe*) or File snake (*Gonionotophis* sp). Each donor snake is housed in a quarantined environment and about 15% of its blood taken every 4-6 weeks, preferably every 5 weeks. The need for repeated blood draws from a snake requires reduced stress on the snake as well as the ability to obtain the blood in a manner that ensures sterility. Blood is drawn from the snake into a vacuum tube, maintaining sterility of the blood. The blood is treated with an anticoagulant or blood thinner, such as citrate dextrose, and centrifuged to obtain plasma which can be frozen and pooled for use in therapeutic treatment or for further fractionation.

In a preferred embodiment, the therapeutic antivenom composition is a mixture of plasma obtained from two, three, or more donor snake species. For example, plasma from a first snake species and plasma from a second snake species are pooled into a single antivenom composition. It is understood that the volume ratio of plasma from the first snake species to the plasma from the second snake species can vary. For example, the ratio of first snake species plasma to second snake species plasma can range from about 1:5 to about 5:1, about 1:4 to about 4:1, about 1:3 to about 3:1, about 1:1 to about 2:1, about 1:1 to about 3:1, about 1:1 to about 4:1, or about 1:1 to about 5:1. Likewise, the plasma from a first snake species, the plasma from a second snake species, and the plasma from a third snake species can be pooled together into a single antivenom composition, and the volume ratio of the three plasma components can vary.

The first and second snake species can be selected from Kingsnakes (*Lampropeltis* sp), Pythons (*Python* sp.), Indigo snakes (*Drymarchon* sp), Mussuranas (*Boiruna* sp), Rat snakes (*Elaphe*) and File snakes (*Gonionotophis* sp). In a preferred embodiment, the antivenom composition is a mixture of Kingsnake and *Python* venom. The first and second snake species can also be selected from a hybrid species as described herein below and exemplified in Table 1. Other therapeutically effective combinations of plasma, at ratios indicated above, include snake species pairs as exemplified in the Table of FIG. 1.

Also described are hybrid snakes for use as donor snakes wherein two snake species which have blood that is therapeutically effective in reducing symptoms of a venomous snakebite are bred. The two parent snakes are geographically isolated such that they would not breed in nature or without human intervention. Examples of such hybrids are presented in Table 1 below. In Table 1, hybrids with 4 "parents" are bred from two snakes that are hybrids themselves. Three parents denotes a hybrid bred with a non-hybrid to produce the resultant hybrid.

TABLE 1

| Parent 1 species | Parent 2 species | Parent 3 Species | Parent 4 Species |
|---|---|---|---|
| *Asphidites ramsayi* | *Python regius* | | |
| *Lampropeltis californiae* | *L.t. campbelli* | | |
| *L. californiae* | *Pantherophis guttatus* | | |
| *L. californiae* | *L.t. hondurensis* | | |
| *L. californiae* | *P. guttatus* | *L.m. thayeri* | |
| *P. guttatus* | *L. californiae* | *L. floridana* | *P. alleghaniensis* |
| *L.t. hondurensis* | *L.t. campbelli* | | |
| *Morelia spilota variegata* | *M. spilota* | *M. boeleni* | |
| *L. californiae* | *L.t. campbelli* | *L.t. campbelli* | *L.t. hondurensis* |

Alternatively, an antivenom composition is obtained from the eggs of donor venomous snakes. In some embodiments, the yolk is treated with caprylic acid to generate a first egg-derived solution containing a therapeutic dose of the antivenom component. The first egg-derived solution can be administered to the snakebite victim or can be further processed to obtain a second egg-derived solution for use in treatment or for further processing. The method for preparing a pharmaceutically effective antivenom composition from snake eggs as described herein provides significant advantages over current methods for preparing antivenom compositions for at least the reason that few reagents and minimal equipment are need for preparation in the field or in the laboratory and can be performed with or without refrigeration.

The antivenom composition is tested for its neutralizing activity prior to packaging for clinical use. The testing is done by mixing the antivenom with venom of the snake for which the antivenom will be labeled. For example, neutralizing activity tests for labeling the product for use in treating a subject bitten by Southern Pacific rattlesnake (*Crotalus oreganus helleri*) can involve mixing the antivenom with varying amounts of venom isolated from a Southern Pacific rattlesnake (see Example 3), then injecting the mixture into a mouse. The antivenom composition is packaged into a therapeutic dose based on the neutralization activity.

Current antivenoms in the United States for pit vipers and black widow spiders are preserved with mercury, a neurotoxin. The processes and compositions described herein have the added advantage in that use of mercury can be eliminated as it is unnecessary for preservation of the composition which is prepared for clinical use.

The antivenom composition prepared from the host snakes listed above can be therapeutically effective in reducing or eliminating the clinical deterioration and the occurrence of systemic cytotoxicity, neurotoxicity, myotoxicity and hemotoxicity associated with the snakebite. In a preferred embodiment, the victim is treated with the antivenom within 12 hours, 10 hours, 8 hours, 6 hours, 5 hours, 4 hours, 3 hours, 2 hours, or 1 hour of the bite occurrence. In some embodiments, administration via intravenous infusion to the snakebite victim reduces the SSS to below 3 after infusion of the composition for a period of between about 1-24 hours, between about 1-12 hours, between about 1-10 hours, between about 1-8 hours, between about 2-8 hours, between about 2-5 hours, between about 1-3 hours, between about 0.25-2 hours, between about 15-90 minutes, between about 15-60 minutes, between about 15-30 minutes, between about 15-45 minutes, or over about 15 minutes, about 30 minutes, about 45 minutes, about 60 minutes, about 1.5 hours, about 2 hours, about 4 hours, about 6 hours, about 8 hours, about 10 hours, or about 12 hours.

The snakebite victim may also be treated with one or more additional therapeutic agents. For example, the victim may be treated with a pain medication such as tramadol, fentanyl, and/or methadone. The victim may also be treated with an antiemetic such as maropitant citrate. The additional therapeutic agents can also include neostigmine nasal spray. Treatment with additional therapeutic agents can be before, during and/or after administration of an antivenom as described herein.

Prior to treatment, the victim can be assessed and assigned a SSS using the Snake Severity Score method developed by Dart et al. (1996, Ann Emerg Med, 27:321-326). The SSS correlates well with the clinical condition of snakebite victims and provides an objective means for evaluating the severity and progression of envenomation in the victims. Accordingly, a snakebite victim is first evaluated and assigned a SSS. Specifically, the victim is assessed for adverse symptoms of the pulmonary system (e.g., dyspnea, respiratory distress, cyanosis), cardiovascular system (e.g., tachycardia or hypotension), gastrointestinal system (e.g., pain, tenesmus, nausea, vomiting or diarrhea), hematological system (e.g., coagulation) and the central nervous system (e.g., apprehension, headache, weakness, dizziness, chills, confusion, lethargy). The wound site is also assessed for, e.g., pain, swelling or ecchymosis.

The victim can be monitored during and after administration of the antivenom composition with continual reassessment of the SSS to ensure the SSS is decreasing over time and that the victim is not experiencing any new adverse effects which may be due to the antivenom concentration. A therapeutically effective dose of the antivenom composition is one which results in a decrease in the SSS to a score of less than 2 within 1 hour, 2 hours, 3 hours, 4 hours, 5 hours, 6 hours, 7 hours, or 8 hours after the start of the administration. In some embodiments, a therapeutically effective dose of the antivenom composition is one which results in a decrease in the SSS to a score of less than 1 within 1 hour, 2 hours, 3 hours, 4 hours, 5 hours, 6 hours, 7 hours, or 8 hours after the start of the administration.

Pain experienced by a snakebite may also be assessed or measured using the Glasgow Composite Measure Pain Scale as is known in the art (Holton et al., 2001, Vet Rec., 148:525-531; Reid et al., 2007, Animal Welfare, 16(S):97-104). This pain scale measures pain on a scale of 0-4 based in part on animal behavior such as looking at the wound, licking rubbing and/or chewing the wound or painful area. Accordingly, therapeutically effective treatment of a canine snakebite victim with an antivenom as described herein results in a decrease in pain. For example, a pain score is reduced from 4 to 3, 4 to 2, 4 to 1, or 4 to 0. The period of pain reduction can be about 1 day to 7 days, about 1 day to 5 days, or about 1 day to 3 days.

Other pain scales or assessment means can be used to measure pain reduction upon treatment with an antivenom. Accordingly, therapeutically effective treatment of a snakebite can be one in which pain is reduced by at least about 10%, about 20%, about 30%, about 40%, about 50%, about 60%, about 70%, about 80%, or about 90% when assessed and compared from the time of antivenom administration to the time of assessment. Assessment may be done at 1 day, 2 days, 3 days, 4 days, 5 days, 6 days, or 7 days after treatment.

The foregoing examples of the related art and limitations related therewith are intended to be illustrative and not exclusive. Other limitations of the related art will become apparent to those of skill in the art upon a reading of the specification and a study of the drawings.

EXAMPLES

The following examples are illustrative in nature and are in no way intended to be limiting.

Example 1

Preparation of an Antivenom Composition from Snake Blood

To obtain a pharmaceutical composition, quarantined Snake-eating snakes Kingsnakes (*Lampropeltis* sp), Indigo snakes (*Drymarchon* sp), Mussuranas (*Boiruna* sp) or File snakes (*Gonionotophis* sp) are bled to obtain about 15% of total blood volume or about 1% of total body weight. Snakes are bled using a closed, sterile vacuum blood collection set.

Blood is collected from each animal every 5 weeks. Whole blood is separated into plasma and red blood cells by first treating the blood with anticoagulant solution which is composed of an AB16 (35.6 g sodium citrate, 12.6 g citric acid monohydrate and 51.0 g glucose monohydrate) and anticoagulant citrate dextrose (22.0 g sodium citrate, 8.0 g citric acid, 24.5 g dextrose monohydrate) per 1 L water for injection. The blood and anticoagulant solution are incubated at room temperature for 30 minutes, and then centrifuged at 4500 rpm for 10 minutes at 4° C. The collected plasma is stored in sterile containers at 2° C. to 8° C. until it is pooled for further processing.

Example 2

Preparation of a Combined Antivenom Composition

An antivenom composition was prepared in which plasma from two snakes was obtained and pooled prior to administration to a snakebite victim. First, blood was drawn from the heart of *Python* snakes and *Lampropeltis* snakes, placed into a separate tube which was then centrifuged at high speed for 3 minutes. Plasma was drawn off and stored at 4° C. until later use. For each sample from the snakes, a 3 cc syringe and a 1½ inch needle was used to carefully draw plasma away from the hematocrit portion of the blood that has settled to the bottom of the tube, ensuring that the plasma sample did not become contaminated with any hematocrit. The plasma was placed into a vial. Plasma collected from each species was pooled together so that *Python* plasma was in a first collection vial and *Lampropeltis* plasma was in a second vial.

The final antivenom composition was prepared to maintain a 3:1 ratio of *Python* plasma to *Lampropeltis* plasma. Isoproyl alcohol (91%) was placed on the cap top of each collection vial for sterilization then removed after at least 5 minutes. A syringe and needle were then used to transfer *Python* plasma into the syringe, and then the same syringe and needle were used to transfer a volume of *Lampropeltis* plasma into the syringe to produce a 3:1 volume ratio of *Python* plasma to *Lampropeltis* plasma. At this point, the syringe was aspirated a bit more to draw a pocket of air into the syringe. The syringe was then inverted repeatedly, allowing the air bubble to move through the syringe from top to bottom, homogenizing the sample and generating the final antivenom ready for administration to a subject.

Example 3

Preparation of an Antivenom Composition from Eggs

An antivenom composition from snake eggs is produced as follows. Yolks are separated from snake eggs are put into a glass beaker. The beaker is placed on a magnetic stirrer with a stir bar and mixed for about 2 minutes to obtain a homogenous suspension. Nine volumes of distilled $H_2O$ is slowly added while stirring is continued over a period of about 5 minutes. The pH of the solution is adjusted to about 5.5 using 1M HCl. Three mL of a solution of caprylic acid is added with vigorous stirring of the solution for about 10 minutes at which time the pH is adjusted to about 4.9 using 1M NaOH. Stirring is continued for approximately 50 min. The mixed solution is filtered using standard Whatman filter paper into a clean 250 mL glass beaker and the pH is adjusted to 7.2±0.2 using 1M NaOH. The protein concentration of the solution is determined using a standard Bradford assay and is stored at −20° C.

Further purification and concentration is achieved by ammonium sulfate precipitation. Under vigorous stirring 22 g solid $(NH_4)_2SO_4$ per 100 mL of filtrate is slowly added to the filtrate of the caprylic acid precipitation to a final concentration of 20%. Stirring is continued for about 15 min at room temperature. The solution is then transferred to a stirrer at 4° C. and stirring is continued for a minimum of 60 min at 4° C. The solution containing precipitate is then transferred to 50 mL centrifuge tubes and centrifuged for 10 min using a rate of 10000 rpm/8000 g. Centrifugation is conducted at 4° C. The supernatant is discarded and the pellet is dissolved in a minimum volume of Tris Buffered Saline (TBS) (about 2-3 mL). The resultant solution is then dialyzed overnight at 4° C. against 50 volumes of TBS, then filtered through a 0.2 μm filter. The protein concentration of the filtered solution is determined using a standard Bradford assay and purity is assessed using a non-reduced SDS-PAGE (sodium dodecyl sulfate polyacrylamide gel electrophoresis) and coomassie blue staining. Aliquots of the dialyzed solution are stored at −20° C. or −75° C.

Example 4

Neutralizing Activity of the Antivenom Composition

Neutralizing activity of the antivenom activity prepared from *L. getulus* according to Example 1 or Example 2 is assessed by mixing the antivenom composition with snake venom then injecting the mixture into mice to test lethality of the mixture. Venom is obtained from *Crotalus oreganus helleri* (*C. o. helleri*). A venom dose that contains 4.0 to 21.0 $LD_{50}$ is mixed with a volume of *C. o. helleri* antivenom composition as prepared in Example 1 or 2. The plasma-venom mixture is incubated at 37° C. for 45 min, then injected i.p. into mice. Control animals are injected with plasma alone or venom mixed with normal rabbit plasma. Injected animals are observed for 24 hours and mortalities recorded and necropsied. Values representing neutralization potential of a given plasma sample are expressed as the number of $LD_{50}$ completely neutralized (resulting in 100% survival) by the dose of plasma.

Example 5

Method for Treating a Snakebite Victim

The antivenom composition prepared and characterized according to the foregoing Examples is used to treat a mammal which has been bitten by a venomous snake. A dog which has been bitten by a South Western Rattlesnake is evaluated and assigned a snake severity score. An animal with a score of 3 or greater is administered 10 ml of antivenom by intravenous administration. The animal is monitored throughout the time of infusion. Every hour, the SSS is reevaluated and a thromboelastography test is performed. Infusion is continued until the SSS is less than 3.

Example 6

Treatment of a Snakebite Victim

A canine (Vizsla mix) that was bitten by a snake was treated with antivenom prepared according to Example 2 above. An assessment of the bite and symptoms suggested a rattlesnake bite. The canine was a neutered male, 4 years, 6 months of age, weighing 30.5 kg. Two puncture wounds were located on the medial aspect of the left pelvic limb at the level of the hock. The canine had significant swelling and bruising around the puncture wounds and walked with a notable limp on the left pelvic limb. The canine was treated with 10 mL of antivenom, methadone (0.2 mg/kg IV, q6h), fentanyl (2 mcg/kg/hr CRI), and Cerenia 1 mg/kg IV SID. Within 24 hours of administration of the antivenom, the canine was weight bearing. Within 48 hours the bruising at the site of the wound showed significant improvement. Prior to treatment with the antivenom, the canine had a SSS of 5. Within 24 hours of the treatment with the antivenom, the SSS had decreased to 2.

Further, in another example, a second canine that was bitten by a snake and was treated with antivenom prepared according to Example 2 above. The second canine was a female, 7 years of age, weighing 11.8 kg. An assessment of the bite and symptoms suggested a single rattlesnake bite. A SSS score of 3 was assigned to the second canine. The second canine was treated with 10 mL of antivenom prepared according to Example 2 above, methadone (0.3 mg/kg IV), and tramadol (2 mg/kg Oral, 2-3 times/day as needed). After only 2 hours, the second canine went from having a SSS of 3 to a SSS of 0.

While a number of exemplary aspects and embodiments have been discussed above, those of skill in the art will recognize certain modifications, permutations, additions and sub-combinations thereof. It is therefore intended that the following appended clauses and clauses or claims hereafter introduced are interpreted to include all such modifications, permutations, additions and sub-combinations as are within their true spirit and scope.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A method for treating a subject suffering from a venomous snakebite, comprising administering to the subject an antivenom composition comprising plasma components obtained from two or more donor snake species, wherein each donor snake species is a different species and each donor snake species is venomous.

Clause 2. The method of Clause 1, wherein one of the donor snake species is an Eastern Kingsnake (*L. g. getulus*) or a *Python* (*Python* sp).

Clause 3. The method of Clause 1 or 2, wherein the antivenom composition comprises a volume ratio of plasma from a first donor snake species to plasma from a second donor snake species ranging from about 1:1 to 10:1.

Clause 4. The method of Clause 3, wherein the first donor snake species is a *Python* species and the second donor snake species is a *Lampropeltis* species and the volume ratio of plasma from the first donor snake species to plasma from the second donor snake species is 3:1.

Clause 5. The method of any one of the preceding Clauses, wherein the method comprises administering a dose of 0.1 mL/kg to 5 mL/kg of the antivenom composition to the subject.

Clause 6. The method of any one of the preceding Clauses, wherein the subject was bitten by a rattlesnake.

Clause 7. The method of Clause 6, wherein the rattlesnake is a Southern Pacific Rattlesnake (*Crotalus oreganus helleri*).

Clause 8. The method of any one of the preceding Clauses, wherein the subject is a mammal.

Clause 9. The method of any one of the preceding Clauses, wherein the subject is a canine.

Clause 10. The method of any one of Clauses 1-8, wherein the subject is a human.

Clause 11. The method of any one of the preceding Clauses, wherein the administering to the subject comprises intravenous infusion of the antivenom composition.

Clause 12. The method of Clause 11, wherein the administering comprises infusing the composition over a time period of 15 minutes to 3 hours.

Clause 13. The method of any one of the preceding Clauses, wherein prior to the administering the victim has a snakebite severity score (SSS) greater than 3 and wherein the administering comprises infusing the composition into the victim until the SSS is less than 2.

Clause 14. A composition comprising a combination of plasma from two or more snake species, wherein each snake species is different and each snake species is a venomous snake species.

Clause 15 The composition of Clause 14, wherein the combination of plasma is from a first and a second snake species.

Clause 16. The composition of Clause 14, wherein the combination of plasma is from a first and a second and a third snake species.

Clause 17. The composition of Clause 15, wherein the combination of plasma is in a ratio of the volume of plasma from the first snake species to the volume of plasma from the second snake species ranging from about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 5:1 to about 10:1, about 2:1 to about 5:1, about 2:1 to about 2:4, or about 2:1 to about 3:1.

Clause 18. The composition of Clause 17, wherein the ratio of the volume of plasma from the first snake species to the volume of plasma from the second snake species is about 1:1, about 2:1, about 3:1, about 4:1, about 5:1, about 6:1, about 7:1, about 8:1, about 9:1, or about 10:1.

Clause 19. The composition of Clause 18, wherein the ratio of the volume of plasma from the first snake species to the volume of plasma from the second snake species is about 3:1.

Clause 20. The composition of any one of Clauses 14 to 19, wherein at least one of the venomous snake species is a member of the genus *Lampropeltis* sp, *Drymarchon* sp, *Boiruna* sp or *Gonionotophis* sp.

Clause 21. The composition of Clause 19 wherein the first snake species is a *Python* species and the second snake species is a *Lampropeltis* species.

Clause 22. The composition of any one of Clauses 14 to 21, wherein the composition was obtained by Caprylic Acid Precipitation.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various FIGURES and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items, such as from less than one percent to 10 percent.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method for treating a human or canine subject suffering from a venomous snakebite, comprising administering to the subject an antivenom composition comprising plasma obtained from whole blood of two or more donor snake species, wherein one of the donor snake species is a Boa (*Boa* sp), and one of the donor snake species is a Kingsnake (*Lampropeltis* sp.) or a Python (*Python* sp).

2. The method of claim 1, wherein the composition comprises plasma obtained from whole blood of three or more donor snake species, and wherein one of the donor snake species is a Boa (*Boa* sp), one of the donor snake species is a Kingsnake (*Lampropeltis* sp.), and one of the donor snake species is a Python (*Python* sp).

3. The method of claim 1, wherein the antivenom composition comprises a volume ratio of plasma from a first donor snake species to plasma from a second donor snake species ranging from about 1:1 to about 10:1.

4. The method of claim 3, wherein the first donor snake species is a Python species and the second donor snake species is a Boa species and the volume ratio of plasma from the first donor snake species to plasma from the second donor snake species is from about 1:3 to about 3:1.

5. The method of claim 1, wherein the method comprises administering a dose of about 0.1 mL/kg to about 5 mL/kg of the antivenom composition to the subject.

6. The method of claim 1, wherein the subject was bitten by a rattlesnake.

7. The method of claim 6, wherein the rattlesnake is a Southern Pacific Rattlesnake (*Crotalus oreganus helleri*).

8. The method of claim 1, wherein the administering to the subject comprises intravenous infusion of the antivenom composition.

9. The method of claim 8, wherein the administering comprises infusing the composition over a time period of about 15 minutes to about 3 hours.

10. The method of claim 1, wherein prior to the administering the victim has a snakebite severity score (SSS) greater than 3 and wherein the administering comprises infusing the composition into the victim until the SSS is less than 2.

11. A method for treating a human or canine subject suffering from a venomous snakebite, comprising administering to the subject an antivenom composition comprising plasma obtained from whole blood of two or more donor snake species, wherein one of the donor snake species is a Boa (*Boa* sp).

* * * * *